(12) United States Patent
Cherney

(10) Patent No.: US 7,572,813 B2
(45) Date of Patent: Aug. 11, 2009

(54) CYCLIC DERIVATIVES AS MODULATORS OF CHEMOKINE RECEPTOR ACTIVITY

(75) Inventor: Robert Cherney, Newtown, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 573 days.

(21) Appl. No.: 11/315,385

(22) Filed: Dec. 22, 2005

(65) Prior Publication Data

US 2006/0135502 A1 Jun. 22, 2006

Related U.S. Application Data

(62) Division of application No. 10/706,448, filed on Nov. 12, 2003, now Pat. No. 7,045,521, which is a division of application No. 10/027,644, filed on Dec. 20, 2001, now Pat. No. 6,706,712.

(60) Provisional application No. 60/256,904, filed on Dec. 20, 2000.

(51) Int. Cl.
*A61K 31/445* (2006.01)
*C07D 211/56* (2006.01)
(52) U.S. Cl. ...................... 514/329; 546/224
(58) Field of Classification Search ................. 514/329; 546/224
See application file for complete search history.

(56) References Cited

U.S. PATENT DOCUMENTS

| | | | |
|---|---|---|---|
| 4,851,423 | A | 7/1989 | Girijavallabhan et al. |
| 5,272,167 | A | 12/1993 | Girijavallabhan et al. |
| 5,710,171 | A | 1/1998 | Dinsmore et al. |
| 5,770,620 | A | 6/1998 | Mjalli et al. |
| 5,968,965 | A | 10/1999 | Dinsmore et al. |
| 5,981,491 | A | 11/1999 | Baxter et al. |
| 6,011,052 | A | 1/2000 | Padia et al. |
| 6,028,087 | A | 2/2000 | Bondinell et al. |
| 6,030,946 | A | 2/2000 | Klaus et al. |
| 6,048,861 | A | 4/2000 | Askew et al. |
| 6,084,065 | A | 7/2000 | Cammaggi et al. |
| 6,100,423 | A | 8/2000 | Collins et al. |
| 6,162,790 | A | 12/2000 | Bemis et al. |
| 6,706,712 | B2 | 3/2004 | Cherney |
| 6,974,836 | B2 | 12/2005 | Cherney et al. |
| 2003/0216434 | A1 | 11/2003 | Cherney |
| 2004/0186140 | A1 | 9/2004 | Cherney et al. |
| 2004/0186143 | A1 | 9/2004 | Carter et al. |
| 2004/0235835 | A1 | 11/2004 | Carter |
| 2004/0235836 | A1 | 11/2004 | Cherney |
| 2005/0043392 | A1 | 2/2005 | Carter et al. |
| 2005/0054626 | A1 | 3/2005 | Carter et al. |
| 2005/0054627 | A1 | 3/2005 | Carter et al. |
| 2005/0065147 | A1 | 3/2005 | Carter et al. |
| 2005/0282882 | A1 | 12/2005 | Cherney et al. |

FOREIGN PATENT DOCUMENTS

| | | |
|---|---|---|
| EP | 0264795 | 10/1987 |
| EP | 0560407 | 12/1987 |
| EP | 0731107 | 2/1996 |
| JP | 377869 | 3/1991 |
| WO | 93/15047 | 8/1993 |
| WO | 94/03479 | 2/1994 |
| WO | 94/20062 | 9/1994 |
| WO | 96/22966 | 8/1996 |
| WO | 97/00894 | 1/1997 |
| WO | 98/06703 | 2/1998 |
| WO | 99/07351 | 2/1999 |
| WO | 99/07678 | 2/1999 |
| WO | 99/17790 | 4/1999 |
| WO | 99/25686 | 5/1999 |
| WO | 99/40913 | 8/1999 |
| WO | 99/40914 | 8/1999 |
| WO | 97/44329 | 11/1999 |
| WO | 00/42071 | 7/2000 |
| WO | 00/46196 | 8/2000 |
| WO | 00/69815 | 11/2000 |
| WO | 00/69820 | 11/2000 |
| WO | WO02/0250019 | 6/2002 |
| WO | WO02/060859 | 8/2002 |
| WO | WO03/075853 | 9/2003 |
| WO | WO2004/071449 | 8/2004 |
| WO | WO2004/071460 | 8/2004 |
| WO | WO2004/098512 | 11/2004 |
| WO | WO2004/098516 | 11/2004 |

OTHER PUBLICATIONS

Baba et al., A Small-Molecule, Nonpeptide CCR5 Antagonist With Hihgly Potent and Selective Anti-HIV-1 Activity, Proc. Natl. Acad. Sci., May 1999, vol. 96, pp. 6598-5703.

(Continued)

*Primary Examiner*—Taofiq A. Solola
(74) *Attorney, Agent, or Firm*—Terrence J. Bogie; Laurelee A. Duncan; Mary K. VanAtten

(57) ABSTRACT

The present application describes modulators of MCP-1 of formula (I):

$$R^1\underset{R^9}{\overset{R^{1a}\ R^{1b}}{N}}-(CHR^{13})_s\overset{R^{11}}{\underset{}{\overset{B}{\diagup}}}\overset{R^{12}}{\underset{}{}}(CHR^{13})_s-\overset{H}{N}\underset{}{\overset{O}{\diagdown}}(CR^{10}R^{10a})_n-N\underset{Z}{\diagdown}R^2 \quad (I)$$

or pharmaceutically acceptable salt forms thereof, useful for the prevention of rheumatoid arthritis, multiple sclerosis, atherosclerosis and asthma.

14 Claims, No Drawings

OTHER PUBLICATIONS

Forbes, et al., CCR2B Receptor Antagonists: Conversion of a Weak HTS it to a Potent Lead Compound, Bioorganic and Medicinal Chemistry Letters, 2000, vol. 10, pp. 1803-1806.

Mirzadegan, et al. Identification of the Binding Site for a Novel Class of CCR2b Chemokine Receptor Antagonists, The Journal of Biological Chemistry, 2000, vol. 275 No. 33, pp. 25562-25571.

Cutrufo, et al., Effect of MEN 11467, a newty tachykinin $NK_1$ receptor antagonist, in acute rectocolitis induced by acetic acid in guinea-pigs, Eu. J. Pharm., 1999, vol. 374, No. 2, pp. 277-283.

CYCLIC DERIVATIVES AS MODULATORS OF CHEMOKINE RECEPTOR ACTIVITY

CROSS REFERENCE TO RELATED APPLICATION

This application is a Divisional of U.S. Ser. No. 10/706,448 filed on Nov. 12, 2003, which is a Divisional of U.S. Ser. No. 10/027,644 filed on Dec. 20, 2001 which claims priority to U.S. Provisional Application Ser. No. 60/256,904 filed Dec. 20, 2000, the entirety of which is incorporated herein by reference.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, asthma, rheumatoid arthritis, atherosclerosis, and multiple sclerosis.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Luster, New Eng. J. Med. 1998, 338, 436-445 and Rollins, Blood 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in: Horuk, Trends Pharm. Sci. 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell 1993, 72, 415-425, and Luster, New Eng. J. Med. 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., Proc. Natl. Acad. Sci. USA 1994, 91, 2752-2756, and Luster, New Eng. J. Med. 1998, 338, 436-445); CCR-3 (or "CKR-3" or "CC-CKR-3") [eotaxin-1, eotaxin-2, RANTES, MCP-3, MCP-4] (Combadiere, et al., J. Biol. Chem. 1995, 270, 16491-16494, and Luster, New Eng. J. Med. 1998, 338, 436-445); CCR-4 (or "CKR-4" or "CC-CKR-4") [TARC, MIP-1α, RANTES, MCP-1] (Power, et al., J. Biol. Chem. 1995, 270, 19495-19500, and Luster, New Eng. J. Med. 1998, 338, 436-445); CCR-5 (or "CKR-5" OR "CC-CKR-5") [MIP-1α, RANTES, MIP-1β] (Sanson, et al., Biochemistry 1996, 35, 3362-3367); CCR-6 (or "CKR-6" or "CC-CKR-6") [LARC] (Baba, et al., J. Biol. Chem. 1997, 272, 14893-14898); CCR-7 (or "CKR-7" or "CC-CKR-7") [ELC] (Yoshie et al., J. Leukoc. Biol. 1997, 62, 634-644); CCR-8 (or "CKR-8" or "CC-CKR-8") [I-309, TARC, MIP-1] (Napolitano et al., J. Immunol., 1996, 157, 2759-2763, and Bernardini, et al., Eur. J. Immunol. 1998, 28, 582-588); CCR-10 (or "CKR-10" or "CC-CKR-10") [MCP-1, MCP-3] (Bonini, et al., DNA and Cell Biol. 1997, 16, 1249-1256); and CCR-11 [MCP-1, MCP-2, and MCP-4] (Schweickert, et al., J. Biol. Chem. 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, Curr. Opin. Biotech. 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: Bharat K. Trivedi, et al, Ann. Reports Med. Chem. 2000, 35, 191; John Saunders and Christine M. Tarby, Drug Disc. Today 1999, 4, 80; Brett A. Premack and Thomas J. Schall, Nature Medicine 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, cellular degranulation, and the promotion of leukocyte migration. Demonstration of the importance of the MCP-1/CCR-2 interaction has been provided by experiments with genetically modified mice. MCP-1-/- mice had normal numbers of leukocytes and macrophages, but were unable to recruit monocytes into sites of inflammation after several different types of immune challenge (Bao Lu, et al., J. Exp. Med. 1998, 187, 601). Likewise, CCR-2-/- mice were unable to recruit monocytes or produce interferon-γ when challenged with various exogenous agents; moreover, the leukocytes of CCR-2 null mice did not migrate in response to MCP-1 (Landin Boring, et al., J. Clin. Invest. 1997, 100, 2552), thereby demonstrating the specificity of the MCP-1/CCR-2 interaction. Two other groups have independently reported equivalent results with different strains of CCR-2-/- mice (William A. Kuziel, et al., Proc. Natl. Acad. Sci. USA 1997, 94, 12053, and Takao Kurihara, et al., J. Exp. Med. 1997, 186, 1757). The viability and generally normal health of the MCP-1-/- and CCR-2-/- animals is noteworthy, in that disruption of the MCP-1/CCR-2 interaction does not induce physiological crisis. Taken together, these data lead one to the conclusion that molecules that block the actions of MCP-1 would be useful in treating a number of inflammatory and autoimmune disorders. This hypothesis has now been validated in a number of different animal disease models, as described below.

Several studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats (Sawsan Youssef, et al., *J. Clin. Invest.* 2000, 106, 361). Likewise, inflammatory disease symptoms could be controlled via direct administration of antibodies for MCP-1 to rats with collagen-induced arthritis (Hiroomi Ogata, et al., *J. Pathol.* 1997, 182, 106), or streptococcal cell wall-induced arthritis (Ralph C. Schimmer, et al., *J. Immunol.* 1998, 160, 1466). Perhaps most significantly, a peptide antagonist of MCP-1, MCP-1(9-76), was shown both to prevent disease onset and to reduce disease symptoms (depending on the time of administration) in the MRL-1pr mouse model of arthritis (Jiang-Hong Gong, et al., *J. Exp. Med.* 1997, 186, 131).

Three key studies have demonstrated the potential therapeutic value of antagonism of the MCP-1/CCR2 interaction in treating atherosclerosis. For example, when MCP-1–/– mice are mated with LDL receptor-deficient mice, an 83% reduction in aortic lipid deposition was observed (Long Gu, et al., *Mol. Cell* 1998, 2, 275). Similarly, when MCP-1 was genetically ablated from mice which already overexpressed human apolipoprotein B, the resulting mice were protected from atherosclerotic lesion formation relative to the MCP-1+/+ apoB control mice (Jennifa Gosling, et al., *J. Clin. Invest.* 1999, 103, 773). Likewise, when CCR-2–/– mice are crossed with apolipoprotein E mice, a significant decrease in the incidence of atherosclerotic lesions was observed (Landin Boring, et al, *Nature* 1998, 394, 894).

Other studies have demonstrated the potential therapeutic value of antagonism of the MCP-1/CCR-2 interaction in treating multiple sclerosis; all of these studies have been demonstrated in experimental autoimmune encephalomyelitis (EAE), the standard animal model for multiple scelerosis. Administration of antibodies for MCP-1 to animals with EAE significantly diminished disease relapse (K. J. Kennedy, et al., *J. Neuroimmunol.* 1998, 92, 98). Furthermore, two recent reports have now shown that CCR-2–/– mice are resistant to EAE (Brian T. Fife, et al., *J. Exp. Med.* 2000, 192, 899; Leonid Izikson, et al., *J. Exp. Med.* 2000, 192, 1075).

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Jose-Angel Gonzalo, et al., *J. Exp. Med.* 1998, 188, 157). It proved possible to reduce allergic airway inflammation in *Schistosoma mansoni* egg-challenged mice through the administration of antibodies for MCP-1 (Nicholas W. Lukacs, et al., *J. Immunol.* 1997, 158, 4398). Consistent with this, MCP-1–/– mice displayed a reduced response to challenge with *Schistosoma mansoni egg* (Bao Lu, et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Clare M. Lloyd, et al., *J. Exp. Med.* 1997, 185, 1371). In addition, MCP-1–/– mice with induced nephrotoxic serum nephritis showed significantly less tubular damage than their MCP-1+/+ counterparts (Gregory H. Tesch, et al., *J. Clin. Invest.* 1999, 103, 73).

One study has demonstrated the potential therapeutic value of antagonism of the MCP-1/CCR2 interaction in treating systemic lupus erythematosus. Crossing of MCP-1–/– mice with MRL-FAS$^{lpr}$ mice—the latter of which have a fatal autoimmune disease that is analogous to human systemic lupus erythematosus—results mice that have less disease and longer survival than the wildtype MRL-FAS$^{lpr}$ mice (Gregory H. Tesch, et al., *J. Exp. Med.* 1999, 190, 1813).

One study has demonstrated the potential therapeutic value of antagonism of the MCP-1/CCR2 interaction in treating colitis. CCR-2–/– mice were protected from the effects of dextran sodium sulfate-induced colitis (Pietro G. Andres, et al., *J. Immunol.* 2000, 164, 6303).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Michael L. Jones, et al., *J. Immunol.* 1992, 149, 2147).

Other studies have provided evidence that MCP-1 is overexpressed in various disease states not mentioned above. These reports provide strong correlative evidence that MCP-1 antagonists could be useful therapeutics for such diseases. Two reports described the overexpression of MCP-1 in the intestinal epithelial cells and bowel mucosa of patients with inflammatory bowel disease (H. C. Reinecker, et al., *Gastroenterology* 1995, 108, 40, and Michael C. Grimm, et al., *J. Leukoc. Biol.* 1996, 59, 804). Two reports describe the overexpression of MCP-1 rats with induced brain trauma (J. S. King, et al., *J. Neuroimmunol.* 1994, 56, 127, and Joan W. Berman, et al., *J. Immunol.* 1996, 156, 3017). Another study has demonstrated the overexpression of MCP-1 in rodent cardiac allografts, suggesting a role for MCP-1 in the pathogenesis of transplant arteriosclerosis (Mary E. Russell, et al. *Proc. Natl. Acad. Sci. USA* 1993, 90, 6086). The overexpression of MCP-1 has been noted in the lung endothelial cells of patients with idiopathic pulmonary fibrosis (Harry N. Antoniades, et al., *Proc. Natl. Acad. Sci. USA* 1992, 89, 5371). Similarly, the overexpression of MCP-1 has been noted in the skin from patients with psoriasis (M. Deleuran, et al., *J. Dermatol. Sci.* 1996, 13, 228, and R. Gillitzer, et al., *J. Invest. Dermatol.* 1993, 101, 127). Finally, a recent report has shown that MCP-1 is overexpressed in the brains and cerebrospinal fluid of patients with HIV-1-associated dementia (Alfredo Garzino-Demo, WO 99/46991).

It should also be noted that CCR-2 has been implicated as a co-receptor for some strains of HIV (B. J. Doranz, et al., *Cell* 1996, 85, 1149). It has also been determined that the use of CCR-2 as an HIV co-receptor can be correlated with disease progression (Ruth I. Connor, et al., *J. Exp. Med.* 1997, 185, 621). This finding is consistent with the recent finding that the presence of a CCR-2 mutant, CCR2-64I, is positively correlated with delayed onset of HIV in the human population (Michael W. Smith, et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

Recently, a number of groups have described the development of small molecule antagonists of MCP-1 (reviewed in: Bharat K. Trivedi, et al, *Ann. Reports Med. Chem.* 2000, 35, 191). Workers at Teijen and Combichem reported the use of cyclic amines (A) as MCP-1 (Tatsuki Shiota, et al., WO 99/25686; Tatsuki Shiota, et al., WO 00/69815) and MIP-1α

(Christine Tarby and Wilna Moree, WO 00/69820) antagonists. These compounds are distinguished from those of the present invention (I) by the requirement for the central cyclic amine grouping.

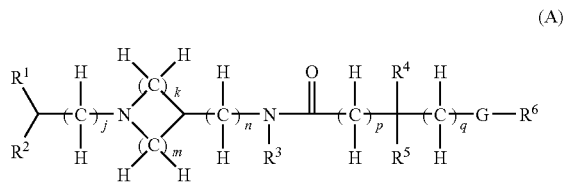

(A)

A number of other groups have also described the development of small molecule antagonists of the MCP-1/CCR-2 interaction. To date, indolopiperidines (Ian T. Forbes, et al., *Bioorg. Med. Chem. Lett.* 2000, 10, 1803), spiropiperidines (Tara Mirzadegan, et al., *J. Biol. Chem.* 2000, 275, 25562), quaternary amines (Masanori Baba, et al., *Proc. Natl. Acad. Sci.* 1999, 96, 5698), 2-substituted indoles (Alan Faull and Jason Kettle, WO 00/46196; Andrew John Barker, et al., WO 99/07351; Andrew John Barker, et al., WO 99/07678), pyrazolone derivatives (Janak Khimchand Padia, et al., U.S. Pat. No. 6,011,052, 2000), 2-substituted benzimidazoles (David Thomas Connor, et al., WO 98/06703), N,N-dialkylhomopiperazines (T. Shiota, et al., WO 97/44329), bicyclic pyrroles (Andrew J. Barker, et al., WO 99/40913 and Andrew J. Barker, et al., WO 99/40914), and 5-aryl pentadienamides (K. G. Carson, et al., Cambridge Health Tech Institute Chemokine Symposium, McLean, Va., USA, 1999) have all been reported as MCP-1 antagonists. The foregoing reference compounds are readily distinguished structurally from the present invention by virtue of substantial differences in the terminal functionality, the attachment functionality, or the core functionality. The prior art does not disclose nor suggest the unique combination of structural fragments that embody in the novel compounds described herein. Furthermore, the prior art does not disclose or suggest that the compounds of the present invention would be antagonists of MCP-1.

It should be noted that CCR-2 is also the receptor for the chemokines MCP-2, MCP-3, MCP-4, and MCP-5 (Luster, *New Eng. J. Med.* 1998, 338, 436-445). Since it is presumed that the new compounds of formula (I) described herein antagonize MCP-1 by binding to the CCR-2 receptor, it may be that these compounds of formula (I) are also effective antagonists of the actions of MCP-2, MCP-3, MCP-4, and MCP-5 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis, multiple sclerosis, and atherosclerosis, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclic derivatives for use in therapy.

The present invention provides the use of novel cyclic derivatives for the manufacture of a medicament for the treatment of inflammatory diseases.

These and other features of the invention, which will become apparent during the following detailed description, have been achieved by the inventors' discovery that compounds of formula (I):

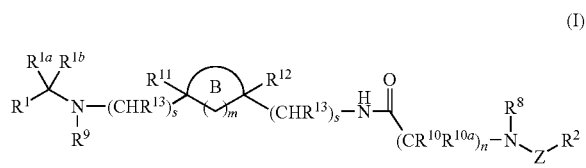

(I)

or stereoisomers or pharmaceutically acceptable salts thereof, wherein Z, m, n, s, $R^1$, $R^{1a}$, $R^{1b}$, $R^2$, $R^8$, $R^9$, $R^{10}$, $R^{10a}$, $R^{11}$, $R^{12}$, and $R^{13}$ are defined below, are effective modulators of chemokine activity.

DETAILED DESCRIPTION OF PREFERRED EMBODIMENTS

[1] Thus, in a first embodiment, the present invention provides novel compounds of formula (I):

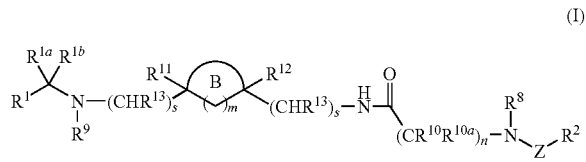

(I)

or a stereoisomer or a pharmaceutically acceptable salt thereof, wherein:

ring B is a cycloalkyl group of 3 to 8 carbon atoms wherein the cycloalkyl group is saturated or partially unsaturated; or a heterocycle of 3 to 7 atoms wherein the heterocycle is saturated or partially unsaturated, the heterocycle containing a heteroatom selected from —O—, —S—, —S(=O)—, —S(=O)$_2$—, and —N($R^4$)—, the heterocycle optionally containing a —C(O)—; ring B being substituted with 0-2 $R^5$;

Z is selected from a bond, —C(O)—, —C(O)NH—, —C(S)NH—, —SO$_2$—, and —SO$_2$NH—;

$R^{1a}$ and $R^{1b}$ are independently selected from H, $C_{1-4}$ alkyl, $C_{1-4}$ cycloalkyl, $CF_3$, or alternatively, $R^{1a}$ and $R^{1b}$ are taken together to from =O;

$R^1$ is selected from a $C_{6-10}$ aryl group substituted with 0-5 $R^6$ and a 5-10 membered heteroaryl system containing 1-4 heteroatoms selected from N, O, and S, substituted with 0-3 $R^6$;

R² is selected from a C$_{6-10}$ aryl group substituted with 0-5 R⁷ and a 5-10 membered heteroaryl system containing 1-4 heteroatoms selected from N, O, and S, substituted with 0-3 R⁷;

R⁴ is selected from H, C$_{1-6}$ alkyl, C$_{3-8}$ alkenyl, C$_{3-8}$ alkynyl, (CRR)$_q$OH, (CRR)$_r$SH, (CRR)$_r$OR$^{4d}$, (CHR)$_r$SR$^{4d}$, (CRR)$_r$NR$^{4a}$R$^{4a}$, (CRR)$_q$C(O)OH, (CRR)$_r$C(O)R$^{4b}$, (CRR)$_t$C(O)NR$^{4a}$R$^{4a}$, (CRR)$_t$OC(O)NR$^{4a}$R$^{4a}$, (CRR)$_t$NR$^{4a}$C(O)OR$^{4d}$, (CRR)$_t$NR$^{4a}$C(O)R$^{4b}$, (CRR)$_t$C(O)OR$^{4b}$, (CRR)$_t$OC(O)R$^{4b}$, (CRR)$_t$S(O)$_p$R$^{4b}$, (CRR)$_t$S(O)$_2$NR$^{4a}$R$^{4a}$, (CRR)$_t$NR$^{4a}$S(O)$_2$R$^{4b}$, C$_{1-6}$ haloalkyl, a (CRR)$_r$—C$_{3-10}$ carbocyclic residue substituted with 0-3 R$^{4e}$, and a (CHR)$_r$-4-10 membered heterocyclic system containing 1-4 heteroatoms selected from N, O, and S, substituted with 0-2 R$^{4e}$;

R$^{4a}$, at each occurrence, is independently selected from H, methyl substituted with 0-1 R$^{4c}$, C$_{2-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, a (CH$_2$)$_r$—C$_{3-10}$ carbocyclic residue substituted with 0-4 R$^{4e}$, and a (CHR)$_r$-4-10 membered heterocyclic system containing 1-4 heteroatoms selected from N, O, and S, substituted with 0-2 R$^{4e}$;

R$^{4b}$, at each occurrence, is selected from H, C$_{1-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, a (CH$_2$)$_r$—C$_{3-6}$ carbocyclic residue substituted with 0-2 R$^{4e}$, and a (CHR)$_r$-4-10 membered heterocyclic system containing 1-4 heteroatoms selected from N, O, and S, substituted with 0-2 R$^{4e}$;

R$^{4c}$ is independently selected from —C(O)R$^{4b}$, —C(O)OR$^{4d}$, —C(O)NR$^{4f}$R$^{4f}$, and (CH$_2$)$_r$phenyl;

R$^{4d}$, at each occurrence, is selected from methyl, CF$_3$, C$_{1-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, and a C$_{3-10}$ carbocyclic residue substituted with 0-3 R$^{4e}$;

R$^{4e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, —C(O)R$^{4i}$, —C(O)OR$^{4j}$, —C(O)NR$^{4h}$R$^{4h}$, —OC(O)NR$^{4h}$R$^{4h}$, —NR$^{4h}$C(O)NR$^{4h}$R$^{4h}$, —NR$^{4h}$C(O)OR$^{4j}$, and (CH$_2$)$_r$phenyl;

R$^{4f}$, at each occurrence, is selected from H, C$_{1-6}$ alkyl, C$_{3-6}$ cycloalkyl, and phenyl;

R$^{4h}$, at each occurrence, is independently selected from H, C$_{1-6}$ alkyl, C$_{3-8}$ alkenyl, C$_{3-8}$ alkynyl, and a (CH$_2$)$_r$—C$_{3-10}$ carbocyclic;

R$^{4i}$, at each occurrence, is selected from H, C$_{1-6}$ alkyl, C$_{3-8}$ alkenyl, C$_{3-8}$ alkynyl, and a (CH$_2$)$_r$—C$_{3-6}$ carbocyclic residue;

R$^{4j}$, at each occurrence, is selected from CF$_3$, C$_{1-6}$ alkyl, C$_{3-8}$ alkenyl, C$_{3-8}$ alkynyl, and a C$_{3-10}$ carbocyclic residue;

R⁵, at each occurrence, is independently selected from H, C$_{1-6}$ alkyl, C$_{2-8}$ alkenyl, C$_{2-8}$ alkynyl, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$OC(O)NR$^{5a}$R$^{5a}$, (CRR)$_r$NR$^{5a}$C(O)OR$^{5d}$, (CRR)$_r$NR$^{5a}$C(O)NR$^{5a}$R$^{5a}$, (CRR)$_r$NR$^{5a}$C(O)H, (CRR)$_r$C(O)OR$^{5b}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, (CRR)$_r$NR$^{5a}$S(O)$_2$NR$^{5a}$R$^{5a}$, C$_{1-6}$ haloalkyl, a (CRR)$_r$—C$_{3-10}$ carbocyclic residue substituted with 0-3 R$^{5c}$, and a (CRR)$_r$-5-10 membered heterocyclic system containing 1-4 heteroatoms selected from N, O, and S, substituted with 0-2 R$^{5c}$;

R$^{5a}$, at each occurrence, is independently selected from H, methyl substituted with 0-1 R$^{5g}$, C$_{2-6}$ alkyl substituted with 0-2 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-10}$ carbocyclic residue substituted with 0-5 R$^{5e}$, and a (CH$_2$)$_r$-5-10 membered heterocyclic system containing 1-4 heteroatoms selected from N, O, and S, substituted with 0-3 R$^{5e}$;

R$^{5b}$, at each occurrence, is selected from C$_{1-6}$ alkyl substituted with 0-3 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-6}$ carbocyclic residue substituted with 0-2 R$^{5e}$, and a (CH$_2$)$_r$-5-6 membered heterocyclic system containing 1-4 heteroatoms selected from N, O, and S, substituted with 0-3 R$^{5e}$;

R$^{5c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{5f}$R$^{5f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{5b}$, (CH$_2$)$_r$C(O)NR$^{5f}$R$^{5f}$, (CH$_2$)$_r$NR$^{5f}$C(O)R$^{5b}$, (CH$_2$)$_r$C(O)OC$_{1-4}$ alkyl, (CH$_2$)$_r$OC(O)R$^{5b}$, (CH$_2$)$_r$C(=NR$^{5f}$)NR$^{5f}$R$^{5f}$, (CH$_2$)$_r$S(O)$_p$R$^{5b}$, (CH$_2$)$_r$NHC(=NR$^{5f}$)NR$^{5f}$R$^{5f}$, (CH$_2$)$_r$S(O)$_2$NR$^{5f}$R$^{5f}$, (CH$_2$)$_r$NR$^{5f}$S(O)$_2$R$^{5b}$, and (CH$_2$)$_r$phenyl substituted with 0-3 R$^{5e}$;

R$^{5d}$, at each occurrence, is selected from methyl, CF$_3$, C$_{2-6}$ alkyl substituted with 0-2 R$^{5e}$, C$_{3-8}$ alkenyl substituted with 0-2 R$^{5e}$, C$_{3-8}$ alkynyl substituted with 0-2 R$^{5e}$, and a C$_{3-10}$ carbocyclic residue substituted with 0-3 R$^{5e}$;

R$^{5e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{5f}$R$^{5f}$, and (CH$_2$)$_r$phenyl;

R$^{5f}$, at each occurrence, is selected from H, C$_{1-6}$ alkyl, and C$_{3-6}$ cycloalkyl; R$^{5g}$ is independently selected from —C(O)R$^{5b}$, —C(O)OR$^{5d}$, —C(O)NR$^{5f}$R$^{5f}$, and (CH$_2$)$_r$phenyl;

R, at each occurrence, is selected from H, C$_{1-6}$ alkyl substituted with R$^{5e}$, C$_{2-8}$ alkenyl, C$_{2-8}$ alkynyl, (CH$_2$)$_r$C$_{3-6}$ cycloalkyl, and (CH$_2$)$_r$phenyl substituted with R$^{5e}$;

R⁶, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{6a}$R$^{6a}$, (CR'R')$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$SC(O)(CR'R')$_r$R$^{6b}$, (CR'R')$_r$C(O)OH, (CR'R')$_r$C(O)(CR'R')$_r$R$^{6b}$, (CR'R')$_r$NR$^{6a}$R$^{6a}$, (CR'R')$_r$C(O)NR$^{6a}$R$^{6a}$, (CR'R')$_r$NR$^{6f}$C(O)(CR'R')$_r$R$^{6b}$, (CR'R')$_r$C(O)O(CR'R')$_r$R$^{6d}$, (CR'R')$_r$OC(O)(CR'R')$_r$R$^{6b}$, (CR'R')$_r$OC(O)NR$^{6a}$(CR'R')$_r$R$^{6d}$, (CR'R')$_r$NR$^{6a}$C(O)NR$^{6a}$(CR'R')$_r$R$^{6d}$, (CR'R')$_r$NR$^{6a}$C(S)NR$^{6a}$(CR'R')$_r$R$^{6d}$, (CR'R')$_r$NR$^{6f}$C(O)O(CR'R')$_r$R$^{6b}$, (CR'R')$_r$C(=NR$^{6f}$)NR$^{6a}$R$^{6a}$, (CR'R')$_r$NHC(=NR$^{6f}$)NR$^{6f}$R$^{6f}$, (CR'R')$_r$S(O)$_p$(CR'R')$_r$R$^{6b}$, (CR'R')$_r$S(O)$_2$NR$^{6a}$R$^{6a}$, (CR'R')$_r$NR$^{6f}$S(O)$_2$NR$^{6a}$R$^{6a}$, (CR'R')$_r$NR$^{6f}$S(O)$_2$(CR'R')$_r$R$^{6b}$, C$_{1-6}$ haloalkyl, C$_{2-8}$ alkenyl substituted with 0-3 R', C$_{2-8}$ alkynyl substituted with 0-3 R', and (CR'R')$_r$phenyl substituted with 0-3 R$^{6e}$;

alternatively, two R⁶ on adjacent atoms on R¹ may join to form a cyclic acetal;

R$^{6a}$, at each occurrence, is selected from H, methyl substituted with 0-1 R$^{6g}$, C$_{2-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CH$_2$)$_r$-C$_{3-10}$ carbocyclic residue substituted with 0-5 R$^{6e}$, and a (CH$_2$)$_r$-5-10 membered heterocyclic system containing 1-4 heteroatoms selected from N, O, and S, substituted with 0-2 R$^{6e}$;

R$^{6b}$, at each occurrence, is selected from H, C$_{1-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CH$_2$)$_r$C$_{3-6}$ carbocyclic residue substituted with 0-3 R$^{6e}$, and a (CH$_2$)$_r$-5-6 membered heterocyclic system containing 1-4 heteroatoms selected from N, O, and S, substituted with 0-2 R$^{6e}$;

R$^{6d}$, at each occurrence, is selected from C$_{3-8}$ alkenyl substituted with 0-2 R$^{6e}$, C$_{3-8}$ alkynyl substituted with 0-2 R$^{6e}$, methyl, CF$_3$, C$_{2-6}$ alkyl substituted with 0-3 R$^{6e}$, a (CH$_2$)$_r$-C$_{3-10}$ carbocyclic residue substituted with 0-3 R$^{6e}$, and a (CH$_2$)$_r$-5-6 membered heterocyclic system containing 1-4 heteroatoms selected from N, O, and S, substituted with 0-3 R$^{6e}$;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is selected from H, C$_{1-5}$ alkyl, and C$_{3-6}$ cycloalkyl, and phenyl;

R$^{6g}$ is independently selected from —C(O)R$^{6b}$, —C(O)OR$^{6d}$, —C(O)NR$^{6f}$R$^{6f}$, and (CH$_2$)$_r$phenyl;

R$^7$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O(CR'R')$_r$R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O) (CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$C(O)O(CR'R')$_r$R$^{7d}$, (CR'R')$_r$OC(O)(CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7b}$, (CR'R')$_r$C(=NR$^{7f}$)NR$^{7a}$R$^{7a}$, (CR'R')$_r$NHC(=NR$^{7f}$)NR$^{7f}$R$^{7f}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$R$^{7b}$, C$_{1-6}$ haloalkyl, C$_{2-8}$ alkenyl substituted with 0-3 R', C$_{2-8}$ alkynyl substituted with 0-3 R', and (CR'R')$_r$phenyl substituted with 0-3 R$^{7e}$;

alternatively, two R$^7$ on adjacent atoms on R$^2$ may join to form a cyclic acetal;

R$^{7a}$, at each occurrence, is independently selected from H, methyl substituted with 0-1 R$^{7g}$, C$_{2-6}$ alkyl substituted with 0-2 R$^{7e}$, C$_{3-8}$ alkenyl substituted with 0-2 R$^{7e}$, C$_{3-8}$ alkynyl substituted with 0-2 R$^{7e}$, a (CH$_2$)$_r$—C$_{3-10}$ carbocyclic residue substituted with 0-5 R$^{7e}$, and a (CH$_2$)$_r$-5-10 membered heterocyclic system containing 1-4 heteroatoms selected from N, O, and S, substituted with 0-2 R$^{7e}$;

R$^{7b}$, at each occurrence, is selected from C$_{1-6}$ alkyl substituted with 0-2 R$^{7e}$, C$_{3-8}$ alkenyl substituted with 0-2 R$^{7e}$, C$_{3-8}$ alkynyl substituted with 0-2 R$^{7e}$, a (CH$_2$)$_r$C$_{3-6}$ carbocyclic residue substituted with 0-3 R$^{7e}$, and a (CH$_2$)$_r$-5-6 membered heterocyclic system containing 1-4 heteroatoms selected from N, O, and S, substituted with 0-2 R$^{7e}$;

R$^{7d}$, at each occurrence, is selected from C$_{3-8}$ alkenyl substituted with 0-2 R$^{7e}$, C$_{3-8}$ alkynyl substituted with 0-2 R$^{7e}$, methyl, CF$_3$, C$_{2-6}$ alkyl substituted with 0-3 R$^{7e}$, a (CH$_2$)$_r$—C$_{3-10}$ carbocyclic residue substituted with 0-3 R$^{7e}$, and a (CH$_2$)$_r$-5-6 membered heterocyclic system containing 1-4 heteroatoms selected from N, O, and S, substituted with 0-3 R$^{7e}$;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, C$_{1-5}$ alkyl, and C$_{3-6}$ cycloalkyl, and phenyl;

R$^{7g}$ is independently selected from —C(O)R$^{7b}$, —C(O)OR$^{7d}$, —C(O)NR$^{7f}$R$^{7f}$, and (CH$_2$)$_r$phenyl;

R', at each occurrence, is selected from H, C$_{1-6}$ alkyl substituted with R$^{6e}$, C$_{2-8}$ alkenyl, C$_{2-8}$ alkynyl, (CH$_2$)$_r$C$_{3-6}$ cycloalkyl, and (CH$_2$)$_r$phenyl substituted with R$^{6e}$;

R$^8$ is selected from H, C$_{1-4}$ alkyl, and C$_{3-4}$ cycloalkyl;

R$^9$ is selected from H, C$_{1-4}$ alkyl, C$_{3-4}$ cycloalkyl, and (CH$_2$)—R$^1$;

R$^{10}$ and R$^{10a}$ are independently selected from H, and C$_{1-4}$alkyl substituted with 0-1 R$^{10b}$, alternatively, R$^{10}$ and R$^{10a}$ can join to form a C$_{3-6}$ cycloalkyl;

R$^{10b}$, at each occurrence, is independently selected from —OH, —SH, NR$^{10c}$R$^{10c}$, —C(O)NR$^{10c}$R$^{10c}$, and —NHC(O)R$^{10c}$;

R$^{10c}$ is selected from H, C$_{1-4}$ alkyl and C$_{3-6}$ cycloalkyl;

R$^{11}$ is selected from H, C$_{1-4}$ alkyl, (CHR)$_q$OH, (CHR)$_q$SH, (CHR)$_q$OR$^{11d}$, (CHR)$_q$S(O)$_p$R$^{11d}$, (CHR)$_r$C(O)R$^{11b}$, (CHR)$_r$NR$^{11a}$R$^{11a}$, (CHR)$_r$C(O)NR$^{11a}$R$^{11a}$, (CHR)$_r$C(O)NR$^{11a}$OR$^{11d}$, (CHR)$_q$NR$^{11a}$C(O)R$^{11b}$, (CHR)$_q$NR$^{11a}$C(O)OR$^{11d}$, (CHR)$_q$OC(O)NR$^{11a}$R$^{11a}$, (CHR)$_r$C(O)OR$^{11d}$, a (CHR)$_r$—C$_{3-6}$ carbocyclic residue substituted with 0-5 R$^{11e}$, and a (CHR)$_r$-5-10 membered heterocyclic system containing 1-4 heteroatoms selected from N, O, and S, substituted with 0-3 R$^{11e}$;

R$^{11a}$, at each occurrence, is independently selected from H, C$_{1-4}$ alkyl, C$_{3-4}$ alkenyl, C$_{3-4}$ alkynyl, (CH$_2$)$_r$C$_{3-6}$ cycloalkyl, a (CH$_2$)$_r$—C$_{3-6}$ carbocyclic residue substituted with 0-5 R$^{11e}$, and a (CH$_2$)$_r$-5-6 membered heterocyclic system containing 1-4 heteroatoms selected from N, O, and S, substituted with 0-3 R$^{11e}$;

R$^{11b}$, at each occurrence, is independently selected from C$_{1-4}$ alkyl, C$_{2-4}$ alkenyl, C$_{2-4}$ alkynyl, a (CH$_2$)$_r$—C$_{3-6}$ carbocyclic residue substituted with 0-2 R$^{11e}$, and a (CH$_2$)$_r$-5-6 membered heterocyclic system containing 1-4 heteroatoms selected from N, O, and S, substituted with 0-3 R$^{11e}$;

R$^{11d}$, at each occurrence, is independently selected from H, methyl, —CF$_3$, C$_{2-4}$ alkyl, C$_{3-6}$ alkenyl, C$_{3-6}$ alkynyl, a C$_{3-6}$ carbocyclic residue substituted with 0-3 R$^{11e}$, and a (CH$_2$)$_r$-5-6 membered heterocyclic system containing 1-4 heteroatoms selected from N, O, and S, substituted with 0-3 R$^{11e}$;

R$^{11e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-6}$ alkyl, SH, (CH$_2$)$_r$SC$_{1-5}$ alkyl, (CH$_2$)$_r$NR$^{11f}$R$^{11f}$, and (CH$_2$)$_r$ phenyl;

R$^{11f}$, at each occurrence, is selected from H, C$_{1-6}$ alkyl, and C$_{3-6}$ cycloalkyl;

R$^{12}$ is selected from H, C$_{1-4}$ alkyl, (CHR)$_q$OH, (CHR)$_q$SH, (CHR)$_q$OR$^{12d}$, (CHR)$_q$S(O)$_p$R$^{12d}$, (CHR)$_r$C(O)R$^{12b}$, (CHR)$_r$NR$^{12a}$R$^{12a}$, (CHR)$_r$C(O)NR$^{12a}$R$^{12a}$, (CHR)$_r$C(O)NR$^{12a}$OR$^{12d}$, (CHR)$_q$NR$^{12a}$C(O)R$^{12b}$, (CHR)$_q$NR$^{12a}$C(O)OR$^{12d}$, (CHR)$_q$OC(O)NR$^{12a}$R$^{12a}$, (CHR)$_r$C(O)OR$^{12d}$, a (CHR)$_r$—C$_{3-6}$ carbocyclic residue substituted with 0-5 R$^{12e}$, and a (CHR)$_r$-5-10 membered heterocyclic system containing 1-4 heteroatoms selected from N, O, and S, substituted with 0-3 R$^{12e}$;

R$^{12a}$, at each occurrence, is independently selected from H, C$_{1-4}$ alkyl, C$_{3-4}$ alkenyl, C$_{3-4}$ alkynyl, (CH$_2$)$_r$C$_{3-6}$ cycloalkyl, a (CH$_2$)$_r$—C$_{3-6}$ carbocyclic residue substituted with 0-5 R$^{12e}$, and a (CH$_2$)$_r$-5-6 membered heterocyclic system containing 1-4 heteroatoms selected from N, O, and S, substituted with 0-3 R$^{12e}$;

R$^{12b}$, at each occurrence, is independently selected from C$_{1-4}$ alkyl, C$_{2-4}$ alkenyl, C$_{2-4}$ alkynyl, a (CH$_2$)$_r$—C$_{3-6}$ carbocyclic residue substituted with 0-2 R$^{12e}$, and a (CH$_2$)$_r$-5-6 membered heterocyclic system containing 1-4 heteroatoms selected from N, O, and S, substituted with 0-3 R$^{12e}$;

R$^{12d}$, at each occurrence, is independently selected from H, methyl, —CF$_3$, C$_{2-4}$ alkyl, C$_{3-6}$ alkenyl, C$_{3-6}$ alkynyl, a C$_{3-6}$ carbocyclic residue substituted with 0-3 R$^{12e}$, and a (CH$_2$)$_r$-5-6 membered heterocyclic system containing 1-4 heteroatoms selected from N, O, and S, substituted with 0-3 R$^{12e}$;

R$^{12e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-6}$ alkyl, SH, (CH$_2$)$_r$SC$_{1-5}$ alkyl, (CH$_2$)$_r$NR$^{12f}$R$^{12f}$, and (CH$_2$)$_r$ phenyl;

R$^{12f}$, at each occurrence, is selected from H, C$_{1-6}$ alkyl, and C$_{3-6}$ cycloalkyl;

R$^{13}$, at each occurrence, is independently selected from methyl, C$_{2-4}$ alkyl substituted with 0-1 R$^{13b}$;

R$^{13b}$ is selected from —OH, —SH, —NR$^{13c}$R$^{13c}$, —C(O)NR$^{13c}$R$^{13c}$, and —NHC(O) R$^{13c}$;

R$^{13c}$ is selected from H, C$_{1-4}$ alkyl and C$_{3-6}$ cycloalkyl;

n is selected from 1 and 2;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

s, at each occurrence, is independently selected from 0 and 1; and t, at each occurrence, is independently selected from 2, 3, and 4.

[2] Thus, in a another embodiment, the present invention provides novel compounds of formula (I):

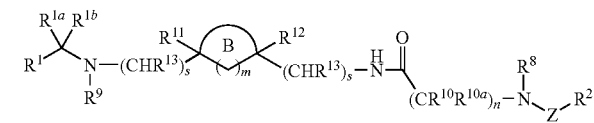

(I)

or a stereoisomer or a pharmaceutically acceptable salt thereof, wherein:

ring B is a cycloalkyl group of 3 to 8 carbon atoms wherein the cycloalkyl group is saturated or partially unsaturated; or a heterocycle of 3 to 7 atoms wherein the heterocycle is saturated or partially unsaturated, the heterocycle containing a heteroatom selected from —O—, —S—, —S(=O)—, —S(=O)$_2$—, and —N(R$^4$)—, the heterocycle optionally containing a —C(O)—; ring B being substituted with 0-2 R$^5$;

Z is selected from a bond, —C(O)—, —C(O)NH—, —C(S)NH—, —SO$_2$—, and —SO$_2$NH—;

R$^{1a}$ and R$^{1b}$ are independently selected from H, C$_{1-4}$ alkyl, C$_{1-4}$ cycloalkyl, CF$_3$, or alternatively, R$^{1a}$ and R$^{1b}$ are taken together to from =O;

R$^1$ is selected from a C$_{6-10}$ aryl group substituted with 0-5 R$^6$ and a 5-10 membered heteroaryl system containing 1-4 heteroatoms selected from N, O, and S, substituted with 0-3 R$^6$;

R$^2$ is selected from a C$_{6-10}$ aryl group substituted with 0-5 R$^7$ and a 5-10 membered heteroaryl system containing 1-4 heteroatoms selected from N, O, and S, substituted with 0-3 R$^7$;

R$^4$ is selected from H, C$_{1-6}$ alkyl, C$_{3-8}$ alkenyl, C$_{3-8}$ alkynyl, (CRR)$_q$OH, (CRR)$_t$SH, (CRR)$_t$OR$^{4d}$, (CHR)$_t$SR$^{4d}$, (CRR)$_t$ NR$^{4a}$R$^{4a}$, (CRR)$_q$C(O)OH, (CRR)$_r$C(O)R$^{4b}$, (CRR)$_r$C(O)NR$^{4a}$R$^{4a}$, (CRR)$_r$OC(O)NR$^{4a}$R$^{4a}$, (CRR)$_r$ NR$^{4a}$C(O)OR$^{4d}$, (CRR)$_r$NR$^{4a}$C(O)R$^{4b}$, (CRR)$_r$S(O)$_p$R$^{4b}$, (CRR)$_r$S(O)$_2$NR$^{4a}$R$^{4a}$, (CRR)$_r$NR$^{4a}$S(O)$_2$R$^{4b}$, C$_{1-6}$ haloalkyl, a (CRR)$_r$—C$_{3-10}$ carbocyclic residue substituted with 0-3 R$^{4e}$, and a (CHR)$_r$-4-10 membered heterocyclic system containing 1-4 heteroatoms selected from N, O, and S, substituted with 0-2 R$^{4e}$;

R$^{4a}$, at each occurrence, is independently selected from H, methyl substituted with 0-1 R$^{4c}$, C$_{2-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, and a (CH$_2$)$_r$—C$_{3-10}$ carbocyclic residue substituted with 0-4 R$^{4e}$;

R$^{4b}$, at each occurrence, is selected from H, C$_{1-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, and a (CH$_2$)$_r$—C$_{3-6}$ carbocyclic residue substituted with 0-2 R$^{4e}$;

R$^{4c}$ is independently selected from —C(O)R$^{4b}$, —C(O)OR$^{4d}$, —C(O)NR$^{4f}$R$^{4f}$, and (CH$_2$)$_r$phenyl;

R$^{4d}$, at each occurrence, is selected from methyl, CF$_3$, C$_{1-6}$ alkyl substituted with 0-3 R$^{4e}$, C$_{3-8}$ alkenyl substituted with 0-3 R$^{4e}$, C$_{3-8}$ alkynyl substituted with 0-3 R$^{4e}$, and a C$_{3-10}$ carbocyclic residue substituted with 0-3 R$^{4e}$;

R$^{4e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, —C(O)R$^{4i}$, —C(O)OR$^{4i}$, —C(O)NR$^{4h}$R$^{4h}$, —OC(O)NR$^{4h}$R$^{4h}$, —NR$^{4h}$C(O)NR$^{4h}$R$^{4h}$, —NR$^{4h}$C(O)OR$^{4i}$, and (CH$_2$)$_r$phenyl;

R$^{4f}$, at each occurrence, is selected from H, C$_{1-6}$ alkyl, C$_{3-6}$ cycloalkyl, and phenyl;

R$^{4h}$, at each occurrence, is independently selected from H, C$_{1-6}$ alkyl, C$_{3-8}$ alkenyl, C$_{3-8}$ alkynyl, and a (CH$_2$)$_r$—C$_{3-10}$ carbocyclic;

R$^{4i}$, at each occurrence, is selected from H, C$_{1-6}$ alkyl, C$_{3-8}$ alkenyl, C$_{3-8}$ alkynyl, and a (CH$_2$)$_r$—C$_{3-6}$ carbocyclic residue;

R$^{4j}$, at each occurrence, is selected from CF$_3$, C$_{1-6}$ alkyl, C$_{3-8}$ alkenyl, C$_{3-8}$ alkynyl, and a C$_{3-10}$ carbocyclic residue;

R$^5$, at each occurrence, is independently selected from H, C$_{1-6}$ alkyl, C$_{2-8}$ alkenyl, C$_{2-8}$ alkynyl, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$OC(O)NR$^{5a}$R$^{5a}$, (CRR)$_r$NR$^{5a}$C(O) OR$^{5d}$, (CRR)$_r$NR$^{5a}$C(O)NR$^{5a}$R$^{5a}$, (CRR)$_r$NR$^{5a}$C(O)H, (CRR)$_r$C(O)OR$^{5b}$, (CRR)$_r$OC(O)R$^{5b}$, (CRR)$_r$S(O)R$^{5b}$, (CRR)$_r$S(O)$_2$NR$^{5a}$R$^{5a}$, (CRR)$_r$NR$^{5a}$S(O)$_2$R$^{5b}$, (CRR)$_r$ NR$^{5a}$S(O)$_2$NR$^{5a}$R$^{5a}$, C$_{1-6}$ haloalkyl, a (CRR)$_r$—C$_{3-10}$ carbocyclic residue substituted with 0-3 R$^{5c}$, and a (CRR)$_r$-5-10 membered heterocyclic system containing 1-4 heteroatoms selected from N, O, and S, substituted with 0-2 R$^{5c}$;

R$^{5a}$, at each occurrence, is independently selected from H, methyl substituted with 0-1 R$^{5g}$, C$_{2-6}$ alkyl substituted with 0-2 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-10}$ carbocyclic residue substituted with 0-5 R$^{5e}$, and a (CH$_2$)$_r$-5-10 membered heterocyclic system containing 1-4 heteroatoms selected from N, O, and S, substituted with 0-3 R$^{5e}$;

R$^{5b}$, at each occurrence, is selected from C$_{1-6}$ alkyl substituted with 0-3 R$^{5e}$, C$_{3-8}$ alkenyl substituted with 0-2 R$^{5e}$, C$_{3-8}$ alkynyl substituted with 0-2 R$^{5e}$, a (CH$_2$)$_r$—C$_{3-6}$ carbocyclic residue substituted with 0-2 R$^{5e}$, and a (CH$_2$)$_r$-5-6 membered heterocyclic system containing 1-4 heteroatoms selected from N, O, and S, substituted with 0-3 R$^{5e}$;

R$^{5c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{5f}$R$^{5f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{5b}$, (CH$_2$)$_r$C(O)NR$^{5f}$R$^{5f}$, (CH$_2$)$_r$NR$^{5f}$C(O)R$^{5b}$, (CH$_2$)$_r$ C(O)OC$_{1-4}$ alkyl, (CH$_2$)$_r$OC(O)R$^{5b}$, (CH$_2$)$_r$C(=NR$^{5f}$)NR$^{5f}$R$^{5f}$, (CH$_2$)$_r$S(O)$_p$R$^{5b}$, (CH$_2$)$_r$NHC(=NR$^{5f}$)

$NR^{5f}R^{5f}$, $(CH_2)_rS(O)_2NR^{5f}R^{5f}$, $(CH_2)_rNR^{5f}S(O)_2R^{5b}$, and $(CH_2)_r$phenyl substituted with 0-3 $R^{5e}$;

$R^{5d}$, at each occurrence, is selected from methyl, $CF_3$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, and a $C_{3-10}$ carbocyclic residue substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, and $(CH_2)_r$phenyl;

$R^{5f}$, at each occurrence, is selected from H, $C_{1-6}$ alkyl, and $C_{3-6}$ cycloalkyl;

$R^{5g}$ is independently selected from $-C(O)R^{5b}$, $-C(O)OR^{5d}$, $-C(O)NR^{5f}R^{5f}$, and $(CH_2)_r$phenyl;

R, at each occurrence, is selected from H, $C_{1-6}$ alkyl substituted with $R^{5e}$, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{6a}R^{6a}$, $(CR'R')_rOH$, $(CR'R')_rO(CR'R')_rR^{6d}$, $(CR'R')_rSH$, $(CR'R')_rC(O)H$, $(CR'R')_rS(CR'R')_rR^{6d}$, $(CR'R')_rC(O)OH$, $(CR'R')_rC(O)(CR'R')_rR^{6b}$, $(CR'R')_rNR^{6a}R^{6a}$, $(CR'R')_rC(O)NR^{6a}R^{6a}$, $(CR'R')_rNR^{6f}C(O)(CR'R')_rR^{6b}$, $(CR'R')_rC(O)O(CR'R')_rR^{6d}$, $(CR'R')_rOC(O)(CR'R')_rR^{6b}$, $(CR'R')_rOC(O)NR^{6a}(CR'R')_rR^{6d}$, $(CR'R')_rNR^{6a}C(O)NR^{6a}(CR'R')_rR^{6d}$, $(CR'R')_rNR^{6a}C(S)NR^{6a}(CR'R')_rR^{6d}$, $(CR'R')_rNR^{6f}C(O)O(CR'R')_rR^{6b}$, $(CR'R')_rC(=NR^{6f})NR^{6a}R^{6a}$, $(CR'R')_rNHC(=NR^{6f})NR^{6f}R^{6f}$, $(CR'R')_rS(O)_p(CR'R')_rR^{6b}$, $(CR'R')_rS(O)_2NR^{6a}R^{6a}$, $(CR'R')_rNR^{6f}S(O)_2NR^{6a}R^{6a}$, $(CR'R')_rNR^{6f}S(O)_2(CR'R')_rR^{6b}$, $C_{1-6}$ haloalkyl, $C_{2-8}$ alkenyl substituted with 0-3 R', $C_{2-8}$ alkynyl substituted with 0-3 R', and $(CR'R')_r$phenyl substituted with 0-3 $R^{6e}$;

alternatively, two $R^6$ on adjacent atoms on $R^1$ may join to form a cyclic acetal;

$R^{6a}$, at each occurrence, is selected from H, methyl substituted with 0-1 $R^{6g}$, $C_{2-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CH_2)_r-C_{3-10}$ carbocyclic residue substituted with 0-5 $R^{6e}$, and a $(CH_2)_r$-5-10 membered heterocyclic system containing 1-4 heteroatoms selected from N, O, and S, substituted with 0-2 $R^{6e}$;

$R^{6b}$, at each occurrence, is selected from H, $C_{1-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CH_2)_rC_{3-6}$ carbocyclic residue substituted with 0-3 $R^{6e}$, and a $(CH_2)_r$-5-6 membered heterocyclic system containing 1-4 heteroatoms selected from N, O, and S, substituted with 0-2 $R^{6e}$;

$R^{6d}$, at each occurrence, is selected from $C_{3-8}$ alkenyl substituted with 0-2 $R^{6e}$, $C_{3-8}$ alkynyl substituted with 0-2 $R^{6e}$, methyl, $CF_3$, $C_{2-6}$ alkyl substituted with 0-3 $R^{6e}$, a $(CH_2)_r-C_{3-10}$ carbocyclic residue substituted with 0-3 $R^{6e}$, and a $(CH_2)_r$-5-6 membered heterocyclic system containing 1-4 heteroatoms selected from N, O, and S, substituted with 0-3 $R^{6e}$;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl;

$R^{6f}$, at each occurrence, is selected from H, $C_{1-5}$ alkyl, and $C_{3-6}$ cycloalkyl, and phenyl;

$R^{6g}$ is independently selected from $-C(O)R^{6b}$, $-C(O)OR^{6d}$, $-C(O)NR^{6f}R^{6f}$, and $(CH_2)_r$phenyl;

$R^7$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{7a}R^{7a}$, $(CR'R')_rOH$, $(CR'R')_rO(CR'R')_rR^{7d}$, $(CR'R')_rSH$, $(CR'R')_rC(O)H$, $(CR'R')_rS(CR'R')_rR^{7d}$, $(CR'R')_rC(O)OH$, $(CR'R')_rC(O)(CR'R')_rR^{7b}$, $(CR'R')_rC(O)NR^{7a}R^{7a}$, $(CR'R')_rNR^{7f}C(O)(CR'R')_rR^{7b}$, $(CR'R')_rC(O)O(CR'R')_rR^{7d}$, $(CR'R')_rOC(O)(CR'R')_rR^{7b}$, $(CR'R')_rOC(O)NR^{7a}(CR'R')_rR^{7a}$, $(CR'R')_rNR^{7a}C(O)NR^{7a}(CR'R')_rR^{7a}$, $(CR'R')_rNR^{7f}C(O)(CR'R')_rR^{7b}$, $(CR'R')_rC(=NR^{7f})NR^{7a}R^{7a}$, $(CR'R')_rNHC(=NR^{7f})NR^{7f}R^{7f}$, $(CR'R')_rS(O)_p(CR'R')_rR^{7b}$, $(CR'R')_rS(O)_2NR^{7a}R^{7a}$, $(CR'R')_rNR^{7f}S(O)_2NR^{7a}R^{7a}$, $(CR'R')_rNR^{7f}S(O)_2(CR'R')_rR^{7b}$, $C_{1-6}$ haloalkyl, $C_{2-8}$ alkenyl substituted with 0-3 R', $C_{2-8}$ alkynyl substituted with 0-3 R', and $(CR'R')_r$phenyl substituted with 0-3 $R^{7e}$;

alternatively, two $R^7$ on adjacent atoms on $R^2$ may join to form a cyclic acetal;

$R^{7a}$, at each occurrence, is independently selected from H, methyl substituted with 0-1 $R^{7g}$, $C_{2-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CH_2)_r-C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-2 $R^{7e}$;

$R^{7b}$, at each occurrence, is selected from $C_{1-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CH_2)_rC_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;

$R^{7d}$, at each occurrence, is selected from $C_{3-8}$ alkenyl substituted with 0-2 $R^{7e}$, $C_{3-8}$ alkynyl substituted with 0-2 $R^{7e}$, methyl, $CF_3$, $C_{2-6}$ alkyl substituted with 0-3 $R^{7e}$, a $(CH_2)_r-C_{3-10}$ carbocyclic residue substituted with 0-3 $R^{7e}$, and a $(CH_2)_r$-5-6 membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, and $C_{3-6}$ cycloalkyl, and phenyl;

$R^{7g}$ is independently selected from $-C(O)R^{7b}$, $-C(O)OR^{7d}$, $-C(O)NR^{7f}R^{7f}$, and $(CH_2)_r$phenyl;

R', at each occurrence, is selected from H, $C_{1-6}$ alkyl substituted with $R^{6e}$, $C_{2-8}$ alkenyl, $C_{2-8}$ alkynyl, $(CH_2)_rC_{3-6}$ cycloalkyl, and $(CH_2)_r$phenyl substituted with $R^{6e}$;

$R^8$ is selected from H, $C_{1-4}$ alkyl, and $C_{3-4}$ cycloalkyl;

$R^9$ is selected from, H, $C_{1-4}$ alkyl, $C_{3-4}$ cycloalkyl, and $(CH_2)-R^1$;

$R^{10}$ and $R^{10a}$ are independently selected from H, and $C_{1-4}$alkyl substituted with 0-1 $R^{10b}$, alternatively, $R^{10}$ and $R^{10a}$ can join to form a $C_{3-6}$ cycloalkyl;

$R^{10b}$, at each occurrence, is independently selected from $-OH$, $-SH$, $NR^{10c}R^{10c}$, $-C(O)NR^{10c}R^{10c}$, and $-NHC(O)R^{10c}$;

$R^{10c}$ is selected from H, $C_{1-4}$ alkyl and $C_{3-6}$ cycloalkyl;

$R^{11}$ is selected from H, $C_{1-4}$ alkyl, $(CHR)_qOH$, $(CHR)_qSH$, $(CHR)_qOR^{11d}$, $(CHR)_qS(O)_pR^{11d}$, $(CHR)_rC(O)R^{11b}$, $(CHR)_rNR^{11a}R^{11a}$, $(CHR)_rC(O)NR^{11a}R^{11a}$, $(CHR)_rC(O)NR^{11a}OR^{11d}$, $(CHR)_qNR^{11a}C(O)R^{11b}$, $(CHR)_qNR^{11a}C(O)OR^{11d}$, $(CHR)_qOC(O)NR^{11a}R^{11a}$, $(CHR)_rC(O)OR^{11d}$, a $(CHR)_r-C_{3-6}$ carbocyclic residue substituted with 0-5 $R^{11e}$, and a $(CHR)_r$-5-10 membered heterocyclic system containing 1-4 heteroatoms selected from N, O, and S, substituted with 0-3 $R^{11e}$;

$R^{11a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_r-C_{3-6}$ carbocyclic residue substituted with 0-5 $R^{11e}$, and a $(CH_2)_r$-5-6 membered heterocyclic system containing 1-4 heteroatoms selected from N, O, and S, substituted with 0-3 $R^{11e}$;

$R^{11b}$, at each occurrence, is independently selected from $C_{1-4}$ alkyl, $C_{2-4}$ alkenyl, $C_{2-4}$ alkynyl, a $(CH_2)_r$—$C_{3-6}$ carbocyclic residue substituted with 0-2 $R^{11e}$, and a $(CH_2)_r$-5-6 membered heterocyclic system containing 1-4 heteroatoms selected from N, O, and S, substituted with 0-3 $R^{11e}$;

$R^{11d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0-3 $R^{11e}$, and a $(CH_2)_r$-5-6 membered heterocyclic system containing 1-4 heteroatoms selected from N, O, and S, substituted with 0-3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{11f}R^{11f}$, and $(CH_2)_r$ phenyl;

$R^{11f}$, at each occurrence, is selected from H, $C_{1-6}$ alkyl, and $C_{3-6}$ cycloalkyl;

$R^{12}$ is selected from H, $C_{1-4}$ alkyl, $(CHR)_qOH$, $(CHR)_qSH$, $(CHR)_qOR^{12d}$, $(CHR)_qS(O)_pR^{12d}$, $(CHR)_qC(O)R^{12b}$, $(CHR)_rNR^{12a}R^{12a}$, $(CHR)_rC(O)NR^{12a}R^{12a}$, $(CHR)_rC(O)NR^{12a}OR^{12d}$, $(CHR)_qNR^{12a}C(O)R^{12b}$, $(CHR)_qNR^{12a}C(O)OR^{12d}$, $(CHR)_qOC(O)NR^{12a}R^{12a}$, $(CHR)_rC(O)OR^{12d}$, a $(CHR)_r$—$C_{3-6}$ carbocyclic residue substituted with 0-5 $R^{12e}$, and a $(CHR)_r$-5-10 membered heterocyclic system containing 1-4 heteroatoms selected from N, O, and S, substituted with 0-3 $R^{12e}$;

$R^{12a}$, at each occurrence, is independently selected from H, $C_{1-4}$ alkyl, $C_{3-4}$ alkenyl, $C_{3-4}$ alkynyl, $(CH_2)_rC_{3-6}$ cycloalkyl, a $(CH_2)_r$—$C_{3-6}$ carbocyclic residue substituted with 0-5 $R^{12e}$, and a $(CH_2)_r$-5-6 membered heterocyclic system containing 1-4 heteroatoms selected from N, O, and S, substituted with 0-3 $R^{12e}$;

$R^{12b}$, at each occurrence, is independently selected from $C_{1-4}$ alkyl, $C_{2-4}$ alkenyl, $C_{2-4}$ alkynyl, a $(CH_2)_r$—$C_{3-6}$ carbocyclic residue substituted with 0-2 $R^{12e}$, and a $(CH_2)_r$-5-6 membered heterocyclic system containing 1-4 heteroatoms selected from N, O, and S, substituted with 0-3 $R^{12e}$;

$R^{12d}$, at each occurrence, is independently selected from H, methyl, —$CF_3$, $C_{2-4}$ alkyl, $C_{3-6}$ alkenyl, $C_{3-6}$ alkynyl, a $C_{3-6}$ carbocyclic residue substituted with 0-3 $R^{12e}$, and a $(CH_2)_r$-5-6 membered heterocyclic system containing 1-4 heteroatoms selected from N, O, and S, substituted with 0-3 $R^{12e}$;

$R^{12e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$ phenyl;

$R^{12f}$, at each occurrence, is selected from H, $C_{1-6}$ alkyl, and $C_{3-6}$ cycloalkyl;

$R^{13}$, at each occurrence, is independently selected from methyl, $C_{2-4}$ alkyl substituted with 0-1 $R^{13b}$;

$R^{13b}$ is selected from —OH, —SH, —$NR^{13c}R^{13c}$, —$C(O)NR^{13c}R^{13c}$, and —$NHC(O)R^{13c}$;

$R^{13c}$ is selected from H, $C_{1-4}$ alkyl and $C_{3-6}$ cycloalkyl;

n is selected from 1 and 2;

m is selected from 0 and 1;

p, at each occurrence, is independently selected from 0, 1, and 2;

q, at each occurrence, is independently selected from 1, 2, 3, and 4;

r, at each occurrence, is independently selected from 0, 1, 2, 3, and 4;

s, at each occurrence, is independently selected from 0 and 1; and t, at each occurrence, is independently selected from 2, 3, and 4.

[3] In another embodiment, the present invention provides novel compounds of formula (I), wherein:

$R^{10}$ and $R^{10a}$ are H;

m is 0;

n is 1; and s is 0.

[4] In another embodiment, the present invention provides novel compounds of formula (I), wherein:

ring B is selected from

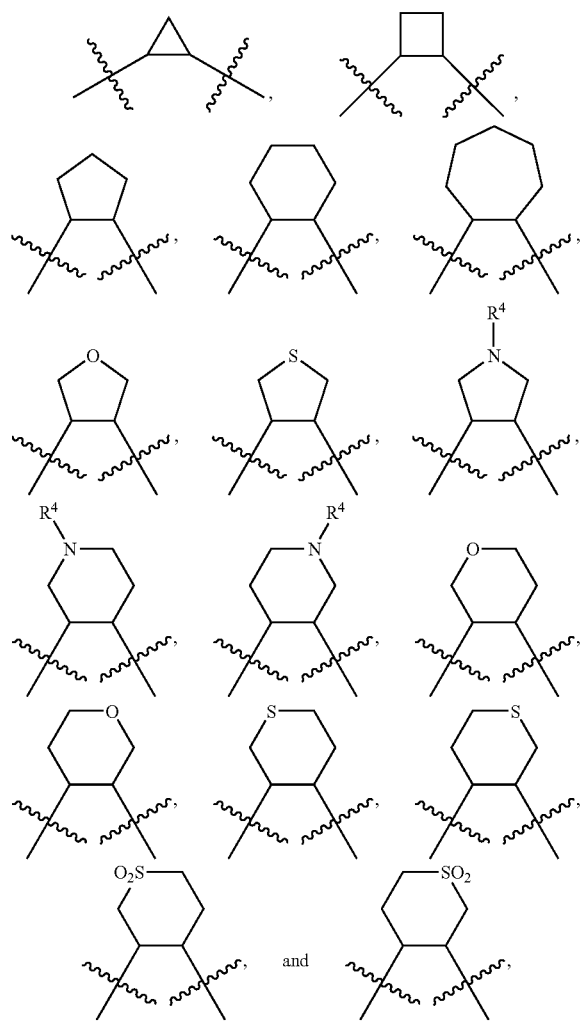

ring B being optionally substituted with 0-1 $R^5$ and $R^{11}$ and $R^{12}$ are H.

[5] In another embodiment, the present invention provides novel compounds of formula (I), wherein:

$R^5$, at each occurrence, is independently selected from H, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rNR^{5a}C(O)OR^{5d}$, $(CRR)_rOC(O)NR^{5a}R^{5a}$, $(CHR)_rNR^{5a}C(O)NR^{5a}R^{5a}$, $CRR(CRR)_r$ $NR^{5a}C(O)H$, $(CRR)_rC(O)OR^{5b}$, $(CRR)_rOC(O)R^{5b}$, $(CRR)_rS(O)_pR^{5b}$, $(CRR)_rS(O)_2NR^{5a}R^{5a}$, $(CRR)_rNR^{5a}S(O)_2R^{5b}$, and $C_{1-6}$ haloalkyl;

$R^{5a}$, at each occurrence, is independently selected from H, methyl, $C_{1-6}$ alkyl substituted with 0-2 $R^{5e}$ wherein the alkyl is selected from ethyl, propyl, i-propyl, butyl, i-butyl, pentyl, hexyl, $C_3$ alkenyl substituted with 0-1 $R^{5e}$, wherein the alkenyl is selected from allyl, $C_3$ alkynyl substituted with 0-1 $R^{5e}$ wherein the alkynyl is selected from propynyl, and a $(CH_2)_r$—$C_{3-4}$ carbocyclic residue substituted with 0-5 $R^{5e}$, wherein the carbocyclic residue is selected from cyclopropyl, and cyclobutyl;

$R^{5b}$, at each occurrence, is selected from $C_{1-6}$ alkyl substituted with 0-2 $R^{5e}$, wherein the alkyl is selected from methyl, ethyl, propyl, i-propyl, butyl, i-butyl, pentyl, and hexyl, a $(CH_2)_r$—$C_{3-4}$ carbocyclic residue substituted with 0-2 $R^{5e}$, wherein the carbocyclic residue is selected from cyclopropyl, and cyclobutyl; and $R^{5d}$, at each occurrence, is selected from methyl, $CF_3$, $C_{2-6}$ alkyl substituted with 0-2 $R^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0-3 $R^{5e}$.

[6] In another embodiment, the present invention provides novel compounds of formula (I), wherein:

$R^4$ is selected from H, $C_{1-6}$ alkyl, $C_{3-8}$ alkenyl, $C_{3-8}$ alkynyl, $(CRR)_qOH$, $(CRR)_tSH$, $(CRR)_tOR^{4d}$, $(CRR)_tSR^{4d}$, $(CRR)_t$ $NR^{4a}R^{4a}$, $(CRR)_qC(O)OH$, $(CRR)_tC(O)R^{4b}$, $(CRR)_tC(O)NR^{4a}R^{4a}$, $(CRR)_tNR^{4a}C(O)R^{4b}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_tC(O)OR^{4b}$, $(CRR)_tOC(O)R^{4b}$, $(CRR)_tS(O)_pR^{4b}$, $(CRR)_tS(O)_2NR^{4a}R^{4a}$, $(CRR)_tNR^{4a}S(O)_2R^{4b}$;

R, at each occurrence, is independently selected from H, methyl, ethyl, propyl, allyl, propynyl, $(CH_2)_rC_{3-6}$ cycloalkyl, and $(CH_2)_r$phenyl substituted with $R^{6e}$;

$R^5$, at each occurrence, is independently selected from H, methyl, ethyl, propyl, i-propyl, butyl, i-butyl, allyl, propynyl, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl;

$R^{5a}$, at each occurrence, is independently selected from H, methyl, ethyl, propyl, i-propyl, butyl, i-butyl, pentyl, hexyl, cyclopropyl, and cyclobutyl; and r, at each occurrence, is selected from 0, 1, and 2.

[7] In another embodiment, the present invention provides novel compounds of formula (I), wherein:

$R^1$ is selected from phenyl substituted with 0-2 $R^6$, and a 5-10 membered heteroaryl system containing 1-4 heteroatoms selected from N, O, and S, substituted with 0-3 $R^6$ wherein the heteroaryl is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

$R^4$ is selected from H, methyl, ethyl, propyl, i-propyl, butyl, i-butyl, allyl, propynyl, $(CRR)_qOH$, $(CRR)_sSH$, $(CRR)_sOR^{4d}$, $(CRR)_sSR^{4d}$, $(CRR)_sNR^{4a}R^{4a}$, $(CRR)_qC(O)OH$, $(CRR)_sC(O)R^{4b}$, $(CRR)_sC(O)NR^{4a}R^{4a}$, $(CRR)_sNR^{4a}C(O)R^{4b}$, $(CRR)_sOC(O)NR^{4a}R^{4a}$, $(CRR)_sNR^{4a}C(O)OR^{4d}$, $(CRR)_sNR^{4a}C(O)R^{4b}$, $(CRR)_sC(O)OR^{4b}$, $(CRR)_sOC(O)R^{4b}$, $(CRR)_sS(O)_pR^{4b}$, $(CRR)_sS(O)_2NR^{4a}R^{4a}$, $(CRR)_rNR^{4a}S(O)_2R^{4b}$;

$R^{4b}$ is selected from H, methyl, ethyl, propyl, i-propyl, butyl, i-butyl, t-butyl, pentyl, and cyclopropyl;

$R^{4d}$ is selected from methyl, ethyl, propyl, i-propyl, butyl, i-butyl, t-butyl, pentyl, and cyclopropyl; and $R^8$ and $R^9$ are independently selected from methyl, ethyl, propyl, i-propyl, and cyclopropyl.

[8] In another embodiment, the present invention provides novel compounds of formula (I), wherein:

$R^6$, at each occurrence, is selected from $C_{1-8}$ alkyl, $C_{2-8}$ alkenyl, $C_{2-8}$ alkynyl, $(CRR)_rC_{3-6}$ cycloalkyl, Cl, Br, I, F, $NO_2$, CN, $(CRR)_rNR^{6a}R^{6a}$, $(CRR)_rOH$, $(CRR)_rO(CRR)_rR^{6d}$, $(CRR)_rSH$, $(CRR)_rC(O)H$, $(CRR)_rS(CRR)_rR^{6d}$, $(CRR)_rC(O)OH$, $(CRR)_rC(O)(CRR)_rR^{6b}$, $(CRR)_rC(O)NR^{6a}R^{6a}$, $(CRR)_rNR^{6f}C(O)(CRR)_rR^{6b}$, $(CRR)_rC(O)O(CRR)_rR^{6d}$, $(CRR)_rNR^{6a}C(O)NR^{6a}R^{6a}$, $(CRR)_rNR^{6a}C(S)NR^{6a}R^{6a}$, $(CRR)_rOC(O)(CRR)_rR^{6b}$, $(CRR)_rS(O)_p(CRR)_rR^{6b}$, $(CRR)_rS(O)_2NR^{6a}R^{6a}$, $(CRR)_rNR^{6f}S(O)_2(CRR)_rR^{6b}$, $(CRR)_rNR^{6f}S(O)_2NR^{6a}R^{6a}$, $C_{1-6}$ haloalkyl, and $(CRR)_r$phenyl substituted with 0-3 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, $CF_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{6f}R^{6f}$, and $(CH_2)_r$phenyl;

$R^{6f}$, at each occurrence, is selected from H, methyl, ethyl, propyl, i-propyl, butyl, i-butyl, t-butyl, pentyl, hexyl, cyclopropyl, and phenyl;

$R^7$ is selected from methyl, ethyl, propyl, i-propyl, butyl, i-butyl, s-butyl, t-butyl, pentyl, hexyl, $(CRR)_rC_{3-6}$ cycloalkyl, Cl, Br, I, F, $NO_2$, CN, $(CRR)_rNR^{7a}R^{7a}$, $(CRR)_r$ OH, $(CRR)_rO(CH)_rR^{7d}$, $(CRR)_rSH$, $(CRR)_rC(O)H$, $(CRR)_rS(CRR)_rR^{7d}$, $(CRR)_rC(O)OH$, $(CRR)_rC(O)(CRR)_r$ $R^{7b}$, $(CRR)_rC(O)NR^{7a}R^{7a}$, $(CRR)_rNR^{7f}C(O)(CRR)_rR^{7b}$, $(CRR)_rC(O)O(CRR)_rR^{7d}$, $(CRR)_rOC(O)(CRR)_rR^{7b}$, $(CRR)_rNR^{7a}C(O)NR^{7a}R^{7a}$, $(CRR)_rNR^{7a}C(O)O(CRR)_r$ $R^{7d}$, $(CRR)_rS(O)_p(CRR)_rR^{7b}$, $(CRR)_rS(O)_2$ $NR^{7a}R^{7a}$, $(CRR)_rNR^{7f}S(O)_2(CRR)_rR^{7b}$, $C_{1-6}$ haloalkyl, and $(CRR)_r$henyl substituted with 0-3 $R^{7e}$;

$R^{7a}$, at each occurrence, is selected from H, methyl, ethyl, propyl, i-propyl, butyl, i-butyl, t-butyl, pentyl, hexyl, prop-2-enyl, 2-methyl-2-propenyl, cyclopropyl, cyclobutyl, cyclopentyl, cyclohexyl, $CH_2$cyclopropyl, and benzyl;

$R^{7b}$, at each occurrence, is selected from methyl, ethyl, propyl, i-propyl, butyl, i-butyl, t-butyl, pentyl, hexyl, cyclopropyl, cyclopentyl, $CH_2$-cyclopentyl, cyclohexyl, $CH_2$-cyclohexyl, $CF_3$, pyrrolidinyl, morpholinyl, and azetidinyl;

$R^{7d}$, at each occurrence, is selected from methyl, $CF_3$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{7f}R^{7f}$, and $(CH_2)_r$phenyl;

$R^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

[9] In another embodiment, the present invention provides novel compounds of formula (I), wherein:

$R^7$ is selected from methyl, ethyl, propyl, i-propyl, butyl, i-butyl, s-butyl, pentyl, hexyl, Cl, Br, I, F, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $OCF_3$, $C(O)R^{7b}$, $NR^{7f}C(O)NR^{7a}R^{7a}$, $NHS(O)_2R^{7b}$,

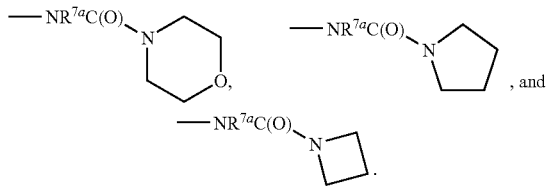

[10] In another embodiment, the present invention provides novel compounds of formula (I), wherein:

ring B is selected from

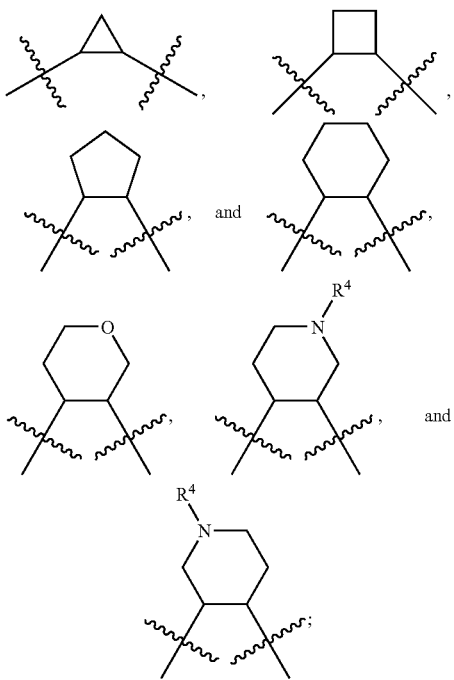

Z is —C(O)—;

$R^{1a}$ and $R^{1b}$ are selected from H and methyl, or alternatively, $R^{1a}$ and $R^{1b}$ are taken together to form =O;

$R^1$ is selected from a $C_{6-10}$ aryl group substituted with 0-3 $R^6$ wherein the aryl group is selected from phenyl and naphthyl, and a 5-10 membered heteroaryl system containing 1-4 heteroatoms selected from N and O, substituted with 0-3 $R^6$ wherein the heteroaryl system is selected from furyl, indolyl, and benzotriazolyl;

$R^2$ is phenyl substituted with 0-1 $R^7$;

$R^4$ is selected from H, methyl, ethyl, propyl, i-propyl, butyl, I-butyl, t-butyl, pentyl, hexyl, and $(CH_2)_rC(O) R^{4b}$;

$R^6$ is selected from methyl, ethyl, propyl, i-propyl, butyl, F, Cl, Br, I, $NO_2$, CN, $O(CH_2)_rR^{6d}$, $C(O)H$, $SR^{6d}$, $NR^{6a}R^{6a}$, $OC(O)R^{6b}$, $S(O)_pR^{6b}$, $(CHR')_rS(O)_2NR^{6a}R^{6a}$, $CF_3$;

$R^{6a}$ is H methyl, or ethyl;

$R^{6b}$ is H or methyl;

$R^{6d}$ is methyl, phenyl, $CF_3$, and $(CH_2)$-phenyl;

$R^9$ is selected from H, methyl, and $(CH_2)$—$R^1$; and r is 0 or 1.

[11] In another embodiment, the present invention provides novel compounds of formula (I), wherein the compound is selected from N-[2-[[(1S,2S)-2-[[(4-Chlorophenyl)methyl]amino]cyclohexyl]amino]-2-oxoethyl]-3-(trifluoromethyl)benzamide;

N-[2-[[(1S,2S)-2-[[(2,4-Dimethylphenyl)methyl]amino]cyclohexyl]amino]-2-oxoethyl]-3-(trifluoromethyl)benzamide, N-[2-[[(1S,2S)-2-[[(2,4,6-Trimethylphenyl)methyl]amino] cyclohexyl]amino]-2-oxoethyl]-3-(trifluoromethyl)benzamide;

N-[2-[[(1S,2S)-2-[[(4-Benzyloxyphenyl)methyl]amino]cyclohexyl]amino]-2-oxoethyl]-3-(trifluoromethyl)benzamide;

N-[2-[[(1S,2S)-2-[[(2,4-Difluorophenyl)methyl]amino]cyclohexyl]amino]-2-oxoethyl]-3-(trifluoromethyl)benzamide;

N-[2-[[(1S,2S)-2-[[(2-Chloro-4-fluorophenyl)methyl] amino]cyclohexyl]amino]-2-oxoethyl]-3-(trifluoromethyl)benzamide;

N-[2-[[(1S,2S)-2-[[(2-Trifluoromethyl-4-fluorophenyl)methyl]amino]cyclohexyl]amino]-2-oxoethyl]-3-(trifluoromethyl)benzamide;

N-[2-[[(1S,2S)-2-[[(2,4-Dichlorophenyl)methyl]amino]cyclohexyl]amino]-2-oxoethyl]-3-(trifluoromethyl)benzamide;

N-[2-[[(1S,2S)-2-[[(2-Fluoro-6-trifluoromethylphenyl)methyl]amino]cyclohexyl]amino]-2-oxoethyl]-3-(trifluoromethyl)benzamide;

N-[2-[[(1S,2S)-2-[[(2-Chloro-5-trifluoromethylphenyl)methyl]amino]cyclohexyl]amino]-2-oxoethyl]-3-(trifluoromethyl)benzamide;

N-[2-[[(1S,2S)-2-[[(1-Naphthyl)methyl]amino]cyclohexyl] amino]-2-oxoethyl]-3-(trifluoromethyl)benzamide;

N-[2-[[(1S,2S)-2-[bis(3-furylmethyl)amino]cyclohexyl] amino]-2-oxoethyl]-3-(trifluoromethyl)benzamide;

N-[2-[[(1S,2S)-2-[(2,4-Dimethylbenzyl)(methyl)amino]cyclohexyl]amino]-2-oxoethyl]-3-(trifluoromethyl)benzamide;

N-[2-[[(1S,2S)-2-[(4-Chlorobenzyl)(methyl)amino]cyclohexyl]amino]-2-oxoethyl]-3-(trifluoromethyl)benzamide;

N-[2-[[(cis)-2-[[(2,4-Dimethylphenyl)methyl]amino]cyclohexyl]amino]-2-oxoethyl]-3-(trifluoromethyl)benzamide;

N-[2-[[(cis)-2-[[(4-Chlorophenyl)methyl]amino]cyclohexyl]amino]-2-oxoethyl]-3-(trifluoromethyl)benzamide;

N-[2-[[(cis)-2-[[(4-Nitrophenyl)methyl]amino]cyclohexyl] amino]-2-oxoethyl]-3-(trifluoromethyl)benzamide;

N-[2-[[(cis)-2-[[(4-Isopropylphenyl)methyl]amino]cyclohexyl]amino]-2-oxoethyl]-3-(trifluoromethyl)benzamide;

N-[2-[[(cis)-2-[[(4-Trifluorophenyl)methyl]amino]cyclohexyl]amino]-2-oxoethyl]-3-(trifluoromethyl)benzamide;

N-[2-[[(cis)-2-[[(4-Trifluoromethoxyphenyl)methyl]amino]cyclohexyl]amino]-2-oxoethyl]-3-(trifluoromethyl)benzamide;
N-[2-[[(cis)-2-[[(4-Phenoxyphenyl)methyl]amino]cyclohexyl]amino]-2-oxoethyl]-3-(trifluoromethyl)benzamide;
N-[2-[[(cis)-2-[[(1-Naphthyl)methyl]amino]cyclohexyl]amino]-2-oxoethyl]-3-(trifluoromethyl)benzamide;
N-[2-[[(cis)-2-[[(2-Naphthyl)methyl]amino]cyclohexyl]amino]-2-oxoethyl]-3-(trifluoromethyl)benzamide;
N-[2-[[(cis)-2-[[(3-Indolyl)methyl]amino]cyclohexyl]amino]-2-oxoethyl]-3-(trifluoromethyl)benzamide;
N-[2-[[(cis)-2-[[1-(4-Chlorophenyl)ethyl]amino]cyclohexyl]amino]-2-oxoethyl]-3-(trifluoromethyl)benzamide;
N-[2-[[(cis)-2-[Bis(3-furylmethyl)amino]cyclohexyl]amino]-2-oxoethyl]-3-(trifluoromethyl)benzamide;
N-[2-[[(1S,2R)-2-[(4-Chlorobenzoyl)amino]cyclopentyl]amino]-2-oxoethyl]-3-(trifluoromethyl)benzamide;
N-[2-[[(1S,2R)-2-[(4-(Methylthio)benzoyl)amino]cyclopentyl]amino]-2-oxoethyl]-3-(trifluoromethyl)benzamide;
N-[2-[[(1S,2R)-2-[(4-(Methylsulfonyl)benzoyl)amino]cyclopentyl]amino]-2-oxoethyl]-3-(trifluoromethyl)benzamide;
N-[2-[[(1S,2R)-2-[(4-Iodobenzoyl)amino]cyclopentyl]amino]-2-oxoethyl]-3-(trifluoromethyl)benzamide;
N-[2-[[(1S,2R)-2-[(4-(Aminosulfonyl)benzoyl)amino]cyclopentyl]amino]-2-oxoethyl]-3-(trifluoromethyl)benzamide;
N-[2-[[(1S,2R)-2-[[(4-Chlorophenyl)methyl]amino]cyclopentyl]amino]-2-oxoethyl]-3-(trifluoromethyl)benzamide;
N-[2-[[(1S,2R)-2-[[(2,4-Dimethylphenyl)methyl]amino]cyclopentyl]amino]-2-oxoethyl]-3-(trifluoromethyl)benzamide;
N-[2-[[(1S,2R)-2-[[(4-Methylphenyl)methyl]amino]cyclopentyl]amino]-2-oxoethyl]-3-(trifluoromethyl)benzamide;
N-[2-[[(cis)-2-[(4-Chlorobenzoyl)amino]cyclohexyl]amino]-2-oxoethyl]-3-(trifluoromethyl)benzamide;
N-[2-[[(cis)-2-[(4-Methylbenzoyl)amino]cyclohexyl]amino]-2-oxoethyl]-3-(trifluoromethyl)benzamide;
N-[2-[[(cis)-2-[(4-Fluorobenzoyl)amino]cyclohexyl]amino]-2-oxoethyl]-3-(trifluoromethyl)benzamide;
N-[2-[[(cis)-2-[Benzoylamino]cyclohexyl]amino]-2-oxoethyl]-3-(trifluoromethyl)benzamide;
N-[2-[[(cis)-2-[(4-Bromobenzoyl)amino]cyclohexyl]amino]-2-oxoethyl]-3-(trifluoromethyl)benzamide;
N-[2-[[(cis)-2-[(4-Phenoxybenzoyl)amino]cyclohexyl]amino]-2-oxoethyl]-3-(trifluoromethyl)benzamide;
N-[2-[[(cis)-2-[(4-Trifluoromethylbenzoyl)amino]cyclohexyl]amino]-2-oxoethyl]-3-(trifluoromethyl)benzamide;
N-[2-[[(cis)-2-[(5-Benzotriazolecarbonyl)amino]cyclohexyl]amino]-2-oxoethyl]-3-(trifluoromethyl)benzamide;
N-[2-[[(cis)-2-[(4-Iodobenzoyl)amino]cyclohexyl]amino]-2-oxoethyl]-3-(trifluoromethyl)benzamide;
N-[2-[[(cis)-2-[(4-Cyanobenzoyl)amino]cyclohexyl]amino]-2-oxoethyl]-3-(trifluoromethyl)benzamide;
N-[2-[[(cis)-2-[(4-Trifluoromethoxybenzoyl)amino]cyclohexyl]amino]-2-oxoethyl]-3-(trifluoromethyl)benzamide;
N-[2-[[(cis)-2-[(4-Formylbenzoyl)amino]cyclohexyl]amino]-2-oxoethyl]-3-(trifluoromethyl)benzamide;
N-[2-[[(cis)-2-[(4-Carbomethoxybenzoyl)amino]cyclohexyl]amino]-2-oxoethyl]-3-(trifluoromethyl)benzamide;
N-[2-[[(cis)-2-[(4-Nitrobenzoyl)amino]cyclohexyl]amino]-2-oxoethyl]-3-(trifluoromethyl)benzamide;
N-[2-[[(cis)-2-[(4-Aminobenzoyl)amino]cyclohexyl]amino]-2-oxoethyl]-3-(trifluoromethyl)benzamide;
N-[2-[[(cis)-2-[(4-Methoxybenzoyl)amino]cyclohexyl]amino]-2-oxoethyl]-3-(trifluoromethyl)benzamide;
N-[2-[[(cis)-2-[(4-Methylthiobenzoyl)amino]cyclohexyl]amino]-2-oxoethyl]-3-(trifluoromethyl)benzamide;
N-[2-[[(cis)-2-[(4-Methylsulfonylbenzoyl)amino]cyclohexyl]amino]-2-oxoethyl]-3-(trifluoromethyl)benzamide;
N-[2-[[(cis)-2-[(4-Aminosulfonylbenzoyl)amino]cyclohexyl]amino]-2-oxoethyl]-3-(trifluoromethyl)benzamide;
N-[2-[[(cis)-2-[(4-Isopropylbenzoyl)amino]cyclohexyl]amino]-2-oxoethyl]-3-(trifluoromethyl)benzamide;
N-[2-[[(cis)-2-[(4-Phenylthiobenzoyl)amino]cyclohexyl]amino]-2-oxoethyl]-3-(trifluoromethyl)benzamide;
N-[2-[[(cis)-2-[(4-(N,N-diethylsulfamoyl)benzoyl)amino]cyclohexyl]amino]-2-oxoethyl]-3-(trifluoromethyl)benzamide;
N-[2-[[(cis)-2-[(4-Trifluoromethylthiobenzoyl)amino]cyclohexyl]amino]-2-oxoethyl]-3-(trifluoromethyl)benzamide;
N-[2-[[(cis)-2-[[(4-Chlorophenyl)methyl]amino]cyclopropyl]amino]-2-oxoethyl]-3-(trifluoromethyl)benzamide;
N-[2-[[(cis)-2-[[(3,4-Dimethylphenyl)methyl]amino]cyclopropyl]amino]-2-oxoethyl]-3-(trifluoromethyl)benzamide;
N-[2-[[(cis)-2-[[(4-Methylphenyl)methyl]amino]cyclopropyl]amino]-2-oxoethyl]-3-(trifluoromethyl)benzamide;
2-Amino-N-[2-[[(cis)-2-[[4-(aminosulfonyl)benzoyl]amino]cyclohexyl]amino]-2-oxoethyl]-5-iodobenzamide;
2-Amino-N-[2-[[(cis)-2-[[4-(aminosulfonyl)benzoyl]amino]cyclohexyl]amino]-2-oxoethyl]-5-chlorobenzamide;
N-[2-[[(cis)-2-[[4-(Aminosulfonyl)benzoyl]amino]cyclohexyl]amino]-2-oxoethyl]-3-chlorobenzamide;
N-[2-[[(cis)-2-[[4-(Aminosulfonyl)benzoyl]amino]cyclohexyl]amino]-2-oxoethyl]-3-trifluoromethoxybenzamide;
Tert-butyl 2-[({2-[((cis)-2-{[4-(aminosulfonyl)benzoyl]amino}cyclohexyl)amino]-2-oxoethyl}amino)carbonyl]-4-(trifluoromethyl)phenylcarbamate;
2-Amino-N-[2-[[(cis)-2-[[4-(aminosulfonyl)benzoyl]amino]cyclohexyl]amino]-2-oxoethyl]-5-trifluoromethylbenzamide trifluoroacetate;
4-(Aminosulfonyl)-N-((cis)-2-{[({2-(trifluoromethyl)anilino]carbonyl}amino)acetyl]amino}cyclohexyl)benzamide;
4-(Aminosulfonyl)-N-{(cis)-2-[({[(3-chlorophenyl)sulfonyl]amino}acetyl)amino]cyclohexyl}benzamide;
Ethyl 2-[({2-[((cis)-2-{[4-(aminosulfonyl)benzoyl]amino}cyclohexyl)amino]-2-oxoethyl}amino)carbonyl]-4-(iodo)phenylcarbamate;
Methyl 2-[({2-[((cis)-2-{[4-(aminosulfonyl)benzoyl]amino}cyclohexyl)amino]-2-oxoethyl}amino)carbonyl]-4-(iodo)phenylcarbamate;
Tert-butyl N-Methyl-2-[({2-[((cis)-2-{[4-(aminosulfonyl)benzoyl]amino}cyclohexyl)amino]-2-oxoethyl}amino)carbonyl]-4-(trifluoromethyl)phenylcarbamate;
Ethyl 2-[({2-[((cis)-2-{[4-(aminosulfonyl)benzoyl]amino}cyclohexyl)amino]-2-oxoethyl}amino)carbonyl]-4-(trifluoromethyl)phenylcarbamate;
2-(Benzylamino)-N-[2-[[(cis)-2-[[4-(aminosulfonyl)benzoyl]amino]cyclohexyl]amino]-2-oxoethyl]-5-trifluoromethyl benzamide;
2-(Ethylamino)-N-[2-[[(cis)-2-[[4-(aminosulfonyl)benzoyl]amino]cyclohexyl]amino]-2-oxoethyl]-5-trifluoromethyl benzamide;
2-(Methylamino)-N-[2-[[(cis)-2-[[4-(aminosulfonyl)benzoyl]amino]cyclohexyl]amino]-2-oxoethyl]-5-trifluoromethyl benzamide;

2-Amino-N-[2-[[(cis)-2-[[4-(aminosulfonyl)benzoyl]amino]cyclohexyl]amino]-2-oxoethyl]-5-bromo benzamide;

Tert-butyl 2-[({2-[((cis)-2-{[4-(aminosulfonyl)benzoyl]amino}cyclohexyl)amino]-2-oxoethyl}amino)carbonyl]-4-(trifluoromethoxy)phenylcarbamate;

2-Amino-N-[2-[[(cis)-2-[[4-(aminosulfonyl)benzoyl]amino]cyclohexyl]amino]-2-oxoethyl]-5-trifluoromethoxy benzamide;

2-(Allylamino)-N-[2-[[(cis)-2-[[4-(aminosulfonyl)benzoyl]amino]cyclohexyl]amino]-2-oxoethyl]-5-trifluoromethyl benzamide;

2-((2-methyl-2-propenyl)amino)-N-[2-[[(cis)-2-[[4-(aminosulfonyl)benzoyl]amino]cyclohexyl]amino]-2-oxoethyl]-5-trifluoromethyl benzamide, 2-(cyclopropylmethylene)amino-N-[2-[[(cis)-2-[[4-(aminosulfonyl)benzoyl]amino]cyclohexyl]amino]-2-oxoethyl]-5-trifluoromethyl benzamide;

2-(butyl)amino-N-[2-[[(cis)-2-[[4-(aminosulfonyl)benzoyl]amino]cyclohexyl]amino]-2-oxoethyl]-5-trifluoromethyl benzamide;

2-(propyl)amino-N-[2-[[(cis)-2-[[4-(aminosulfonyl)benzoyl]amino]cyclohexyl]amino]-2-oxoethyl]-5-trifluoromethyl benzamide;

2-(propyl)amino-N-[2-[[(cis)-2-[[4-(aminosulfonyl)benzoyl]amino]cyclohexyl]amino]-2-oxoethyl]-5-trifluoromethyl benzamide;

2-((2-methyl-2-propyl)amino)-N-[2-[[(cis)-2-[[4-(aminosulfonyl)benzoyl]amino]cyclohexyl]amino]-2-oxoethyl]-5-trifluoromethyl benzamide;

2-((aminocarbonyl)amino)-N-[2-[[(cis)-2-[[4-(aminosulfonyl)benzoyl]amino]cyclohexyl]amino]-2-oxoethyl]-5-trifluoromethyl benzamide;

2-(acetylamino)-N-[2-[[(cis)-2-[[4-(aminosulfonyl)benzoyl]amino]cyclohexyl]amino]-2-oxoethyl]-5-trifluoromethyl benzamide;

2-(Methylamino)-N-[2-[[(cis)-2-[[4-(aminosulfonyl)benzoyl]amino]cyclohexyl]amino]-2-oxoethyl]-5-iodomethyl benzamide;

2-(Ethylamino)-N-[2-[[(cis)-2-[[4-(aminosulfonyl)benzoyl]amino]cyclohexyl]amino]-2-oxoethyl]-5-iodomethyl benzamide;

2-(Trifluoroacetylamino)-N-[2-[[(cis)-2-[[4-(aminosulfonyl)benzoyl]amino]cyclohexyl]amino]-2-oxoethyl]-5-iodomethyl benzamide;

2-(amino)-N-[2-[[(cis)-2-[[4-(aminosulfonyl)benzoyl]amino]cyclohexyl]amino]-2-oxoethyl]-5-nitro benzamide;

Iso-propyl 2-[({2-[((cis)-2-{[4-(aminosulfonyl)benzoyl]amino}cyclohexyl)amino]-2-oxoethyl}amino)carbonyl]-4-(iodo)phenylcarbamate;

Tert butyl 2-[({2-[((cis)-2-{[4-(aminosulfonyl)benzoyl]amino}cyclohexyl)amino]-2-oxoethyl}amino)carbonyl]-4-(iodo)phenylcarbamate;

2-(amino)-N-[2-[[(cis)-2-[[4-(aminosulfonyl)benzoyl]amino]cyclohexyl]amino]-2-oxoethyl]-3,5-dinitro benzamide;

2-((Isopropylaminocarbonyl)amino)-N-[2-[[(cis)-2-[[4-(aminosulfonyl)benzoyl]amino]cyclohexyl]amino]-2-oxoethyl]-5-trifluoromethyl benzamide;

2-((cyclohexylcarbonyl)amino)-N-[2-[[(cis)-2-[[4-(aminosulfonyl)benzoyl]amino]cyclohexyl]amino]-2-oxoethyl]-5-trifluoromethyl benzamide;

2-((Cyclopentylmethylenecarbonyl)amino)-N-[2-[[(cis)-2-[[4-(aminosulfonyl)benzoyl]amino]cyclohexyl]amino]-2-oxoethyl]-5-trifluoromethyl benzamide;

2-((cyclohexylcarbonyl)amino)-N-[2-[[(cis)-2-[[4-(methylsulfonyl)benzoyl]amino]cyclohexyl]amino]-2-oxoethyl]-5-trifluoromethyl benzamide;

2-((cyclohexylcarbonyl)amino)-N-[2-[[(cis)-2-[[4-(methylthio)benzoyl]amino]cyclohexyl]amino]-2-oxoethyl]-5-trifluoromethyl benzamide;

2-((Isopropylaminocarbonyl)amino)-N-[2-[[(cis)-2-[[4-(methylthio)benzoyl]amino]cyclohexyl]amino]-2-oxoethyl]-5-trifluoromethyl benzamide;

2-((Isopropylaminocarbonyl)amino)-N-[2-[[(cis)-2-[[4-(methylsulfonyl)benzoyl]amino]cyclohexyl]amino]-2-oxoethyl]-5-trifluoromethyl benzamide;

2-((Methylsulfonyl)amino)-N-[2-[[(cis)-2-[[4-(aminosulfonyl)benzoyl]amino]cyclohexyl]amino]-2-oxoethyl]-5-trifluoromethyl benzamide;

2-((Aminocarbonyl)amino)-N-[2-[[(cis)-2-[[4-(aminosulfonyl)benzoyl]amino]cyclohexyl]amino]-2-oxoethyl]-5-trifluoromethyl benzamide;

2-((Allyl)amino)-N-[2-[[(cis)-2-[[4-(methylsulfonyl)benzoyl]amino]cyclohexyl]amino]-2-oxoethyl]-5-trifluoromethyl benzamide;

2-((Allyl)amino)-N-[2-[[(cis)-2-[[4-(methylthio)benzoyl]amino]cyclohexyl]amino]-2-oxoethyl]-5-trifluoromethyl benzamide;

2-((2-Methyl-2-propenyl)amino)-N-[2-[[(cis)-2-[[4-(methylsulfonyl)benzoyl]amino]cyclohexyl]amino]-2-oxoethyl]-5-trifluoromethyl benzamide;

2-((2-methyl-2-propenyl)amino)-N-[2-[[(cis)-2-[[4-(methylthio)benzoyl]amino]cyclohexyl]amino]-2-oxoethyl]-5-trifluoromethyl benzamide;

2-((Propyl)amino)-N-[2-[[(cis)-2-[[4-(methylsulfonyl)benzoyl]amino]cyclohexyl]amino]-2-oxoethyl]-5-trifluoromethyl benzamide;

2-((Propyl)amino)-N-[2-[[(cis)-2-[[4-(methylthio)benzoyl]amino]cyclohexyl]amino]-2-oxoethyl]-5-trifluoromethyl benzamide;

2-((2-Methylpropyl)amino)-N-[2-[[(cis)-2-[[4-(methylsulfonyl)benzoyl]amino]cyclohexyl]amino]-2-oxoethyl]-5-trifluoromethyl benzamide;

2-((2-Methylpropyl)amino)-N-[2-[[(cis)-2-[[4-(methylthio)benzoyl]amino]cyclohexyl]amino]-2-oxoethyl]-5-trifluoromethyl benzamide;

2-((Butyl)amino)-N-[2-[[(cis)-2-[[4-(methylsulfonyl)benzoyl]amino]cyclohexyl]amino]-2-oxoethyl]-5-trifluoromethyl benzamide;

2-((Butyl)amino)-N-[2-[[(cis)-2-[[4-(methylthio)benzoyl]amino]cyclohexyl]amino]-2-oxoethyl]-5-trifluoromethyl benzamide;

2-((Ethylaminocarbonyl)amino)-N-[2-[[(cis)-2-[[4-(methylthio)benzoyl]amino]cyclohexyl]amino]-2-oxoethyl]-5-trifluoromethyl benzamide;

2-((Allylaminocarbonyl)amino)-N-[2-[[(cis)-2-[[4-(methylthio)benzoyl]amino]cyclohexyl]amino]-2-oxoethyl]-5-trifluoromethyl benzamide;

2-((Iso-butylaminocarbonyl)amino)-N-[2-[[(cis)-2-[[4-(methylthio)benzoyl]amino]cyclohexyl]amino]-2-oxoethyl]-5-trifluoromethyl benzamide;

2-((Cyclopentylaminocarbonyl)amino)-N-[2-[[(cis)-2-[[4-(methylthio)benzoyl]amino]cyclohexyl]amino]-2-oxoethyl]-5-trifluoromethyl benzamide;

2-((Tert-butoxycarbonyl)amino)-N-[2-[[(cis)-2-[[4-(methylthio)benzoyl]amino]cyclohexyl]amino]-2-oxoethyl]-5-trifluoromethyl benzamide;

2-((Iso-propoxycarbonyl)amino)-N-[2-[[(cis)-2-[[4-(methylthio)benzoyl]amino]cyclohexyl]amino]-2-oxoethyl]-5-trifluoromethyl benzamide;

2-((Ethoxycarbonyl)amino)-N-[2-[[(cis)-2-[[4-(methylthio) benzoyl]amino]cyclohexyl]amino]-2-oxoethyl]-5-trifluoromethyl benzamide;

2-((Pyrrolidinylcarbonyl)amino)-N-[2-[[(cis)-2-[[4-(methylthio)benzoyl]amino]cyclohexyl]amino]-2-oxoethyl]-5-trifluoromethyl benzamide;

2-((Morpholinylcarbonyl)amino)-N-[2-[[(cis)-2-[[4-(methylthio)benzoyl]amino]cyclohexyl]amino]-2-oxoethyl]-5-trifluoromethyl benzamide;

2-((Azetidinylcarbonyl)amino)-N-[2-[[(cis)-2-[[4-(methylthio)benzoyl]amino]cyclohexyl]amino]-2-oxoethyl]-5-trifluoromethyl benzamide;

2-{[1-Pyrrolidinylcarbonyl]amino}-N-{2-[((cis)-4-{[4-(methylthio)benzyl]amino}tetrahydro-2H-pyran-3-yl) amino]-2-oxoethyl}-5-(trifluoromethyl)benzamide;

2-{[1-Azetidinylcarbonyl]amino}-N-{2-[((cis)-4-{[4-(methylthio)benzyl]amino}tetrahydro-2H-pyran-3-yl) amino]-2-oxoethyl}-5-(trifluoromethyl)benzamide;

2-{[1-Azetidinylcarbonyl]amino}-N-{2-[((cis)-4-{[4-(methoxy)benzyl]amino}tetrahydro-2H-pyran-3-yl) amino]-2-oxoethyl}-5-(trifluoromethyl)benzamide;

1-(4-Methylthiobenzoylamino)-2-[2-(2-amino-5-trifluoromethylbenzoylamino)-acetylamino]-4-aminocyclohexane;

[2-({[5-benzyloxycarbonylamino-2-(4-methylthiobenzoylamino)cyclohexylcarbamoyl]-methyl}carbamoyl)-4-trifluoromethylphenyl]carbamic acid tert-butyl ester;

{4-(4-Methylthiobenzoylamino)-3-[2-(3-trifluoromethylbenzoylamino)-acetylamino]-4-aminocyclohexane;

{4-(4-methylthiobenzoylamino)-3-[2-(3-trifluoromethylbenzoylamino)acetylamino]-cyclohexyl}carbamic acid benzyl ester;

1-(4-Methanesulfonylbenzoylamino)-2-[2-(3-trifluoromethylbenzoylamino)-acetylamino]cyclohexyl-4-aminocyclohexane;

1-(4-Methylthiobenzoylamino)-2-[2-(2-amino-5-trifluoromethylbenzoylamino)acetylamino]-4-(2-propylamino) cyclohexane;

1-(4-Methylthiobenzoylamino)-2-[2-(2-amino-5-trifluoromethylbenzoylamino)acetylamino]-4-(3-methylureido) cyclohexane;

1-(4-Methylthiobenzoylamino)-2-[2-(3-trifluoromethylbenzoylamino)acetylamino]6-aminocyclohexane;

1-(4-Methylthiobenzoylamino)-2-[2-(3-trifluoromethylbenzoylamino)acetylamino]6-(2-propylamino)cyclohexane;

1-(4-Methylthio-benzoylamino)-2-[2-(2-Amino-5-trifluoromethyl-benzoylamino)-acetylamino]-4-aminocyclohexane;

4-(4-Methylthiobenzoylamino)-3-[2-(3-trifluoromethylbenzoylamino)acetylamino]-4-(2-propylamino)-cyclohexane;

1-(4-Methylthiobenzoylamino)-2-[2-(3-trifluoromethylbenzoylamino)acetylamino]-5-aminocyclohexane;

2-Amino-N-({2-[(4-methylthiophenylamino)methyl]cyclohexylcarbamoyl}-methyl)-5-(trifluoromethyl)benzamide;

2-Isopropylamino-N-{[(cis)2-(4-methylthiobenzylamino)-cyclohexylcarbamoyl]-methyl}-5-trifluoromethylbenzamide;

2-(3-Isopropylureido)-N-{[2-(4-methylthiobenzylamino)cyclohexylcarbamoyl]-methyl}-5-trifluoromethylbenzamide;

2-(3-Morpholinylureido)-N-{[2-(4-methylthiobenzylamino)cyclohexylcarbamoyl]-methyl}-5-trifluoromethylbenzamide;

2-Amino-N-({2-(cis)-[3-(4-methylthiophenyl)ureido]cyclohexylcarbamoyl}methyl)-5-trifluoromethyl benzamide;

{2-[({2-(Cis)-[3-(4-methanesulfonylphenyl)ureido]cyclohexylcarbamoyl}methyl)carbamoyl]-4-trifluoromethylphenyl}carbamic acid tert-butyl ester;

2-amino-N-{2-[((3S,4R)-4-{[4-(methylthio)benzyl]amino}-1-propyl-3-piperidinyl)amino]-2-oxoethyl}-5-(trifluoromethyl)benzamide;

2-Amino-N-{2-[((3R,4S)-4-{[4-(methylthio)benzyl] amino}-1-propyl-3-piperidinyl)amino]-2-oxoethyl}-5-(trifluoromethyl)benzamide;

2-amino-N-{2-[((cis)-4-{[4-(methylthio)benzoyl]amino}-1-methyl-3-piperidinyl)amino]-2-oxoethyl}-5-(trifluoromethyl)benzamide;

N-{2-[((cis)-4-{[4-chlorobenzyl]amino}-3-piperidinyl) amino]-2-oxoethyl}-3-(trifluoromethyl)benzamide;

N-{2-[((cis)-4-{[4-(methylthio)benzyl]amino}-3-piperidinyl)amino]-2-oxoethyl}-3-(trifluoromethyl)benzamide;

2-Amino-N-{2-[((cis)-4-{[4-chlorobenzyl]amino}-3-piperidinyl)amino]-2-oxoethyl}-5-(trifluoromethyl)benzamide;

2-Amino-N-{2-[((cis)-4-{[4-methylthiobenzyl]amino}-3-piperidinyl)amino]-2-oxoethyl}-5-(trifluoromethyl)benzamide;

2-Amino-N-{2-[((cis)-4-{[4-ethylthiobenzyl]amino}-3-piperidinyl)amino]-2-oxoethyl}-5-(trifluoromethyl)benzamide;

N-{2-[((cis)-4-{[4-methylthiobenzyl]amino}-1-methyl-3-piperidinyl)amino]-2-oxoethyl}-3-(trifluoromethyl)benzamide;

N-{2-[((cis)-4-{bis[4-methylthiobenzyl]amino}-1-methyl-3-piperidinyl)amino]-2-oxoethyl}-3-(trifluoromethyl) benzamide;

2-Amino-N-{2-[((cis)-4-{[4-methylthiobenzyl]amino}-1-methyl-3-piperidinyl)amino]-2-oxoethyl}-5-(trifluoromethyl)benzamide;

N-{2-[((cis)-4-{[4-methylthiobenzyl]amino}-1-acetyl-3-piperidinyl)amino]-2-oxoethyl}-3-(trifluoromethyl)benzamide;

2-Amino-N-{2-[((cis)-4-{[4-methylthiobenzyl]amino}-1-butyl-3-piperidinyl)amino]-2-oxoethyl}-5-(trifluoromethyl)benzamide;

2-Cyclohexylamino-N-{2-[((cis)-4-{[4-methylthiobenzyl] amino}-1-propyl-3-piperidinyl)amino]-2-oxoethyl}-5-(trifluoromethyl)benzamide;

2-Iso-propylamino-N-{2-[((cis)-4-{[4-methylthiobenzyl] amino}-1-propyl-3-piperidinyl)amino]-2-oxoethyl}-5-(trifluoromethyl)benzamide;

2-(Pyrrolidinylcarbonyl)amino-N-{2-[((cis)-4-{[4-methylthiobenzyl]amino}-1-propyl-3-piperidinyl)amino]-2-oxoethyl}-5-(trifluoromethyl)benzamide;

2-(Methylaminocarbonyl)amino-N-{2-[((cis)-4-{[4-methylthiobenzyl]amino}-1-propyl-3-piperidinyl)amino]-2-oxoethyl}-5-(trifluoromethyl)benzamide;

3-Amino-N-{2-[((cis)-4-{[4-methylthiobenzyl]amino}-1-propyl-3-piperidinyl)amino]-2-oxoethyl}-5-(trifluoromethyl)benzamide;

N-{2-[((cis)-4-{[4-aminosulfonylbenzoyl]amino}-3-piperidinyl)amino]-2-oxoethyl}-3-(trifluoromethyl)benzamide;

N-{2-[((cis)-4-{[4-methylsulfonylbenzoyl]amino}-3-piperidinyl)amino]-2-oxoethyl}-3-(trifluoromethyl)benzamide;

2-Amino-N-{2-[((cis)-4-{[4-(methylthio)benzoyl]amino}-3-piperidinyl)amino]-2-oxoethyl}-5-(trifluoromethyl) benzamide;

N-{2-[((cis)-4-{[4-methylthiobenzoyl]amino}-1-methyl-3-piperidinyl)amino]-2-oxoethyl}-3-(trifluoromethyl)benzamide;

N-{2-[((cis)-4-{[4-methylthiobenzoyl]amino}-1-acetyl-3-piperidinyl)amino]-2-oxoethyl}-3-(trifluoromethyl)benzamide;

2-Amino-N-{2-[((cis)-4-{[4-methylthiobenzoyl]amino}-1-butyl-3-piperidinyl)amino]-2-oxoethyl}-3-(trifluoromethyl)benzamide;

2-Cyclohexylamino-N-{2-[((cis)-4-{[4-methylthiobenzoyl]amino}-1-propyl-3-piperidinyl)amino]-2-oxoethyl}-5-(trifluoromethyl)benzamide;

2-Iso-propylamino-N-{2-[((cis)-4-{[4-methylthiobenzoyl]amino}-1-propyl-3-piperidinyl)amino]-2-oxoethyl}-5-(trifluoromethyl)benzamide;

3-Amino-N-{2-[((cis)-4-{[4-methylthiobenzoyl]amino}-1-propyl-3-piperidinyl)amino]-2-oxoethyl}-5-(trifluoromethyl)benzamide;

N-{2-[((cis)-3-{[4-(aminosulfonyl)benzoyl]amino}-4-piperidinyl)amino]-2-oxoethyl}-3-(trifluoromethyl)benzamide;

N-{[4-Dimethylamino-2-(4-methylsulfanyl-benzylamino)-cyclohexylcarbamoyl]-methyl}-3-trifluoromethyl-benzamide trifluoroacetate;

N-{[2-(4-Chloro-benzylamino)-4-dimethylamino-cyclohexylcarbamoyl]-methyl}-3-trifluoromethyl-benzamide trifluoroacetate;

N-{[4-Dimethylamino-2-(4-methoxy-benzylamino)-cyclohexylcarbamoyl]-methyl}-3-trifluoromethyl-benzamide trifluoroacetate; and N-{[4-Dimethylamino-2-(4-methyl-benzylamino)-cyclohexylcarbamoyl]-methyl}-3-trifluoromethyl-benzamide trifluoroacetate.

In another embodiment, the present invention is directed to a pharmaceutical composition, comprising a pharmaceutically acceptable carrier and a therapeutically effective amount of a compound of Formula (I).

In another embodiment, the present invention is directed to a method for modulation of chemokine or chemokine receptor activity comprising administering to a patient in need thereof a therapeutically effective amount of a compound of Formula (I).

In another embodiment, the present invention is directed to a method for modulation of MCP-1, MCP-2, MCP-3 and MCP-4, and MCP-5 activity that is mediated by the CCR2 receptor comprising administering to a patient in need thereof a therapeutically effective amount of a compound of Formula (I).

In another embodiment, the present invention is directed to a method for modulation of MCP-1 activity comprising administering to a patient in need thereof a therapeutically effective amount of a compound of Formula (I).

In another embodiment, the present invention is directed to a method for treating or preventing disorders, comprising administering to a patient in need thereof a therapeutically effective amount of a compound of Formula (I), said disorders being selected from osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis.

In another embodiment, the present invention is directed to a method for treating or preventing disorders, of Formula (I), wherein said disorders being selected from psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis.

In another embodiment, the present invention is directed to a method for treating or preventing disorders, of Formula (I), wherein said disorders being selected from alveolitis, colitis, systemic lupus erythematosus, nephrotoxic serum nephritis, glomerularnephritis, asthma, multiple sclerosis, artherosclerosis, and rheumatoid arthritis.

In another embodiment, the present invention is directed to a method for treating or preventing disorders, of Formula (I), wherein said disorders being selected from asthma, multiple sclerosis, artherosclerosis, and rheumatoid arthritis.

In another embodiment, the present invention is directed to a method for treating or preventing rheumatoid arthritis, comprising administering to a patient in need thereof a therapeutically effective amount of a compound of Formula (I).

In another embodiment, the present invention is directed to a method for treating or preventing multiple sclerosis, comprising administering to a patient in need thereof a therapeutically effective amount of a compound of Formula (I).

In another embodiment, the present invention is directed to a method for treating or preventing atherosclerosis, comprising administering to a patient in need thereof a therapeutically effective amount of a compound of Formula(I).

In another embodiment, the present invention is directed to a method for treating or preventing asthma, comprising administering to a patient in need thereof a therapeutically effective amount of a compound of Formula (I).

In another embodiment, the present invention is directed to a method for treating or preventing inflammatory diseases, comprising administering to a patient in need thereof a therapeutically effective amount of a compound of Formula (I).

In another embodiment, the present invention is directed to a method for modulation of CCR2 activity comprising administering to a patient in need thereof a therapeutically effective amount of a compound of Formula (I).

In another embodiment, ring B is selected from

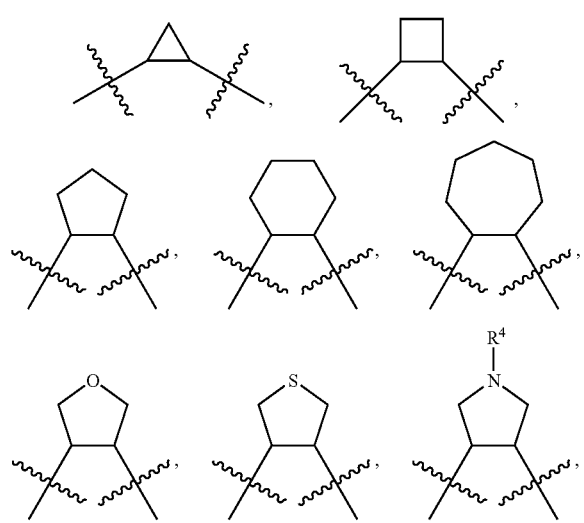

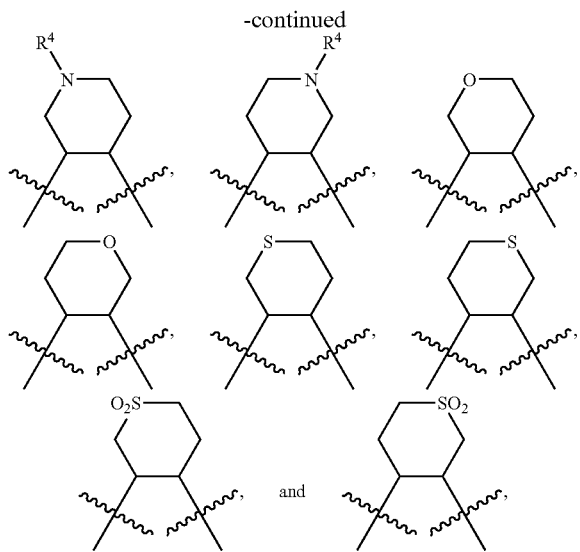

ring B being optionally substituted with 0-1 $R^5$.
In another embodiment, ring B is selected from

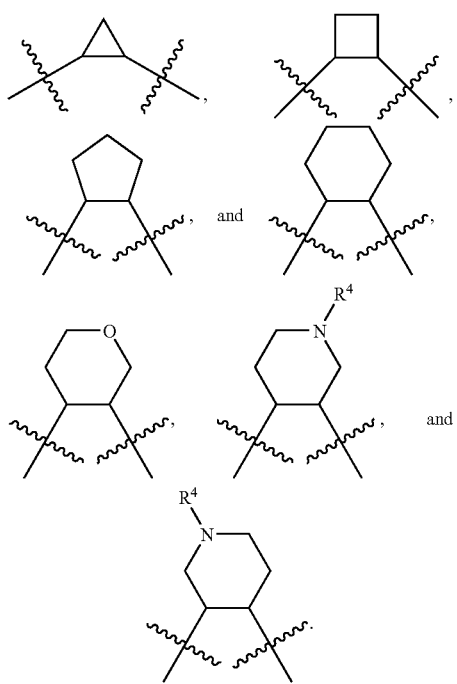

In another embodiment, Z is —C(O)—.

In another embodiment, $R^4$ is selected from H, $C_{1-6}$ alkyl, $C_{3-8}$ alkenyl, $C_{3-8}$ alkynyl, $(CRR)_qOH$, $(CHR)_sSH$, $(CRR)_tOR^{4d}$, $(CHR)_tSR^{4d}$, $(CHR)_rNR^{4a}R^{4a}$, $(CHR)_qC(O)OH$, $(CHR)_rC(O)R^{4b}$, $(CHR)_rC(O)NR^{4a}R^{4a}$, $(CHR)_tNR^{4a}C(O)R^{4b}$, $(CHR)_tOC(O)NR^{4a}R^{4a}$, $(CHR)_tNR^{4a}C(O)OR^{4d}$, $(CHR)_tNR^{4a}C(O)R^{4b}$, $(CHR)_rC(O)OR^{4b}$, $(CHR)_tOC(o)R^{4b}$, $(CHR)_rS(O)_pR^{4b}$, $(CHR)_rS(O)_2NR^{4a}R^{4a}$, $(CHR)_rNR^{4a}S(O)_2R^{4b}$; and R, at each occurrence, is independently selected from H, methyl, ethyl, propyl, allyl, propynyl, $(CH_2)_rC_{3-6}$ cycloalkyl, and $(CH_2)_r$phenyl substituted with $R^{6e}$.

In another embodiment, $R^4$ is selected from H, methyl, ethyl, propyl, i-propyl, butyl, i-butyl, allyl, propynyl, $(CRR)_qOH$, $(CRR)_sSH$, $(CRR)_tOR^{4d}$, $(CRR)_tSR^{4d}$, $(CRR)_tNR^{4a}R^{4a}$, $(CRR)_qC(O)OH$, $(CRR)_tC(O)R^{4b}$, $(CRR)_tC(O)NR^{4a}R^{4a}$, $(CRR)_tNR^{4a}C(O)R^{4b}$, $(CRR)_tOC(O)NR^{4a}R^{4a}$, $(CRR)_tNR^{4a}C(O)OR^{4d}$, $(CRR)_tNR^{4a}C(O)R^{4b}$, $(CRR)_tC(O)OR^{4b}$, $(CRR)_tOC(O)R^{4b}$, $(CRR)_rS(O)_pR^{4b}$, $(CRR)_rS(O)_2NR^{4a}R^{4a}$, $(CRR)_rNR^{4a}S(O)_2R^{4b}$.

$R^{4b}$ is selected from H, methyl, ethyl, propyl, i-propyl, butyl, i-butyl, t-butyl, pentyl, and cyclopropyl; and $R^{4d}$ is selected from methyl, ethyl, propyl, i-propyl, butyl, i-butyl, t-butyl, pentyl, and cyclopropyl.

In another embodiment, $R^4$ is selected from H, methyl, ethyl, propyl, i-propyl, butyl, i-butyl, allyl, propynyl, $(CH_2)_rC(O)R^{4b}$.

In another embodiment, $R^5$, at each occurrence, is independently selected from H, methyl, ethyl, propyl, i-propyl, butyl, i-butyl, allyl, propynyl, $(CH_2)_rOH$, $(CH_2)_rOR^{5d}$, $(CH_2)_rNR^{5a}R^{5a}$, $(CH_2)_rC(O)OH$, $(CH_2)_rC(O)R^{5b}$, $(CH_2)_rC(O)NR^{5a}R^{5a}$, $(CH_2)_rNR^{5a}C(O)R^{5b}$, $(CH_2)_rOC(O)NR^{5a}R^{5a}$, $(CH_2)_rNR^{5a}C(O)OR^{5d}$, $(CH_2)_rNR^{5a}C(O)R^{5b}$, $(CH_2)_rC(O)OR^{5b}$, $(CH_2)_rOC(O)R^{5b}$, $(CH_2)_rNR^{5a}S(O)_2R^{5b}$, and $C_{1-6}$ haloalkyl; and $R^{5a}$, at each occurrence, is independently selected from H, methyl, ethyl, propyl, i-propyl, butyl, i-butyl, pentyl, hexyl, cyclopropyl, and cyclobutyl.

In another embodiment, $R^5$, at each occurrence, is independently selected from H, $(CH_2)_rNR^{5a}R^{5a}$, $(CH_2)_rNR^{5a}C(O)R^{5b}$, and $(CH_2)_rNR^{5a}C(O)OR^{5d}$.

In another embodiment, $R^1$ is selected from phenyl substituted with 0-2 $R^6$, naphthyl substituted with 0-2 $R^6$, and a 5-10 membered heteroaryl system containing 1-4 heteroatoms selected from N, O, and S, substituted with 0-3 $R^6$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, $R^1$ is selected from a $C_{6-10}$ aryl group substituted with 0-3 $R^6$ wherein the aryl group is selected from phenyl and naphthyl, and a 5-10 membered heteroaryl system containing 1-4 heteroatoms selected from N and O, substituted with 0-3 $R^6$ wherein the heteroaryl system is selected from furyl, indolyl, and benzotriazolyl.

In another embodiment, $R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, $R^2$ is selected from phenyl substituted with 0-2 $R^7$.

In another embodiment, $R^6$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CH_2)_rNR^{6a}R^{6a}$, $(CH_2)_rOH$, $(CH_2)_rO(CH_2)_rR^{6d}$, $(CH_2)_rSH$, $(CH_2)_rC(O)H$, $(CH_2)_rS(CH_2)_rR^{6d}$, $(CH_2)_rC(O)OH$, $(CH_2)_rC(O)(CH_2)_rR^{6b}$, $(CH_2)_rC(O)NR^{6a}R^{6a}$, $(CH_2)_rNR^{6f}C(O)(CH_2)_rR^{6b}$, $(CH_2)_r$ C(O)O(CH$_2$)$_r$R$^{6d}$, (CH$_2$)$_r$OC(O)(CH$_2$)$_r$R$^{6b}$, (CH$_2$)$_r$S(O)$_p$ (CH$_2$)$_r$R$^{6b}$, (CH$_2$)$_r$S(O)$_2$NR$^{6a}$R$^{6a}$, (CH$_2$)$_r$NR$^{6f}$S(O)$_2$ (CH$_2$)$_r$R$^{6b}$, (CH$_2$)$_r$NR$^{6f}$S(O)$_2$ NR$^{6a}$R$^{6a}$, C$_{1-6}$ haloalkyl, and (CH$_2$)$_r$phenyl substituted with 0-3 R$^{6e}$;

R$^{6a}$, at each occurrence, is independently selected from H, methyl, ethyl, propyl, i-propyl, butyl, i-butyl, t-butyl, pentyl, hexyl, cyclopropyl and phenyl;

R$^{6b}$, at each occurrence, is selected from methyl, ethyl, propyl, i-propyl, butyl, i-butyl, t-butyl, pentyl, hexyl, cyclopropyl, and phenyl;

R$^{6d}$, at each occurrence, is selected from methyl, CF$_3$, ethyl, propyl, i-propyl, butyl, i-butyl, t-butyl, pentyl, hexyl, cyclopropyl, and phenyl;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$ SC$_{1-5}$ alkyl, (CH$_2$)$_r$NR$^{6f}$R$^{6f}$, and (CH$_2$)$_r$phenyl; and R$^{6f}$, at each occurrence, is selected from H, methyl, ethyl, propyl, i-propyl, butyl, i-butyl, t-butyl, pentyl, hexyl, cyclopropyl, and phenyl.

In another embodiment, R$^6$ is selected from methyl, ethyl, propyl, i-propyl, butyl, F, Cl, Br, I, NO$_2$, CN, O(CH$_2$)$_r$R$^{6d}$, C(O)H, SR$^{6d}$, NR$^{6a}$R$^{6a}$, OC(O)R$^{6b}$, S(O)$_p$R$^{6b}$, (CHR')$_r$S (O)$_2$NR$^{6a}$R$^{6a}$, CF$_3$;

R$^{6a}$ is H, methyl, or ethyl;

R$^{6b}$ is H or methyl; and

R$^{6d}$ is methyl, phenyl, CF$_3$, and (CH$_2$)-phenyl.

In another embodiment, R$^7$ is selected from methyl, ethyl, propyl, i-propyl, butyl, i-butyl, s-butyl, t-butyl, pentyl, hexyl, (CH$_2$)$_r$C$_{3-6}$ cycloalkyl, Cl, Br, I, F, NO$_2$, CN, (CH$_2$)$_r$ NR$^{7a}$R$^{7a}$, (CH$_2$)$_r$OH, (CH$_2$)$_r$O(CH)$_r$R$^{7d}$, (CH$_2$)$_r$SH, (CH$_2$)$_r$C(O)H, (CH$_2$)$_r$S(CH$_2$)$_r$R$^{7d}$, (CH$_2$)$_r$C(O)OH, (CH$_2$)$_r$ C(O)(CH$_2$)$_r$R$^{7b}$, (CH$_2$)$_r$C(O)NR$^{7a}$R$^{7a}$, (CH$_2$)$_r$ NR$^{7f}$C(O)(CH$_2$)$_r$R$^{7b}$, (CH$_2$)$_r$C(O)O(CH$_2$)$_r$R$^{7d}$, (CH$_2$)$_r$ OC(O)(CH$_2$)$_r$ R$^{7b}$, (CH$_2$)$_r$NR$^{7a}$C(O) NR$^{7a}$R$^{7a}$, (CH$_2$)$_r$ NR$^{7a}$C(O)O(CH$_2$)$_r$R$^{7d}$, (CH$_2$)$_r$S(O)$_p$(CH$_2$)$_r$R$^{7b}$, (CH$_2$)$_r$S (O)$_2$ NR$^{7a}$R$^{7a}$, (CH$_2$)$_r$NR$^{7f}$S(O)$_2$(CH$_2$)$_r$R$^{7b}$, C$_{1-6}$ haloalkyl, and (CH$_2$)$_r$phenyl substituted with 0-3 R$^{7e}$;

R$^{7a}$, at each occurrence, is selected from H, methyl, ethyl, propyl, i-propyl, butyl, i-butyl, t-butyl, pentyl, hexyl, and cyclopropyl;

R$^{7b}$, at each occurrence, is selected from methyl, ethyl, propyl, i-propyl, butyl, i-butyl, t-butyl, pentyl, hexyl, and cyclopropyl;

R$^{7d}$, at each occurrence, is selected from methyl, CF$_3$, ethyl, propyl, i-propyl, butyl, i-butyl, t-butyl, pentyl, hexyl, and cyclopropyl;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$ SC$_{1-5}$ alkyl, (CH$_2$)$_r$NR$^{7f}$R$^{7f}$, and (CH$_2$)$_r$phenyl; and R$^{7f}$, at each occurrence, is selected from H, methyl, ethyl, propyl, i-propyl, butyl, i-butyl, t-butyl, pentyl, hexyl, cyclopropyl, and phenyl.

In another embodiment, R$^7$ is selected from methyl, ethyl, propyl, i-propyl, butyl, i-butyl, s-butyl, pentyl, hexyl, Cl, Br, I, F, NO$_2$, NR$^{7a}$R$^{7a}$, NHC(O)NHR$^{7a}$, NR$^{7a}$C(O)R$^{7b}$, NR$^{7a}$C(O)OR$^{7d}$, CF$_3$, OCF$_3$, C(O)R$^{7b}$, NR$^{7f}$C(O)NHR$^{7a}$, and NHS(O)$_2$R$^{7b}$.

In another embodiment, R$^8$ is H.

In another embodiment, R$^9$ is H, methyl, or CH$_2$—R$^1$.

In another embodiment, R$^{11}$ and R$^{12}$ are H.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional even more preferred embodiments of the present invention. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., R$^a$) occurs more than one time in any constituent or formula for a compound, its definition at each occurrence is independent of its definition at every other occurrence. Thus, for example, if a group is shown to be substituted with 0-2 R$^a$, then said group may optionally be substituted with up to two R$^a$ groups and R$^a$ at each occurrence is selected independently from the definition of R$^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "C$_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. C$_{1-8}$ alkyl, is intended to include C$_1$, C$_2$, C$_3$, C$_4$, C$_5$, C$_6$, C$_7$, and C$_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "C$_{3-6}$ cycloalkyl", is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5-6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or in combination with other active ingredients effective to inhibit MCP-1 or effective to treat or prevent inflammatory disorders.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A series of compounds of formulas 6 and 7 are available via the methods shown in Scheme 1. A cyclic diamine 1 can be monoprotected to provide 2. This material can be coupled to the acid 3 to yield the amide 4. Once the protecting group is removed, a reductive amination can be performed to afford target 6. This can be alkylated again to give target 7.

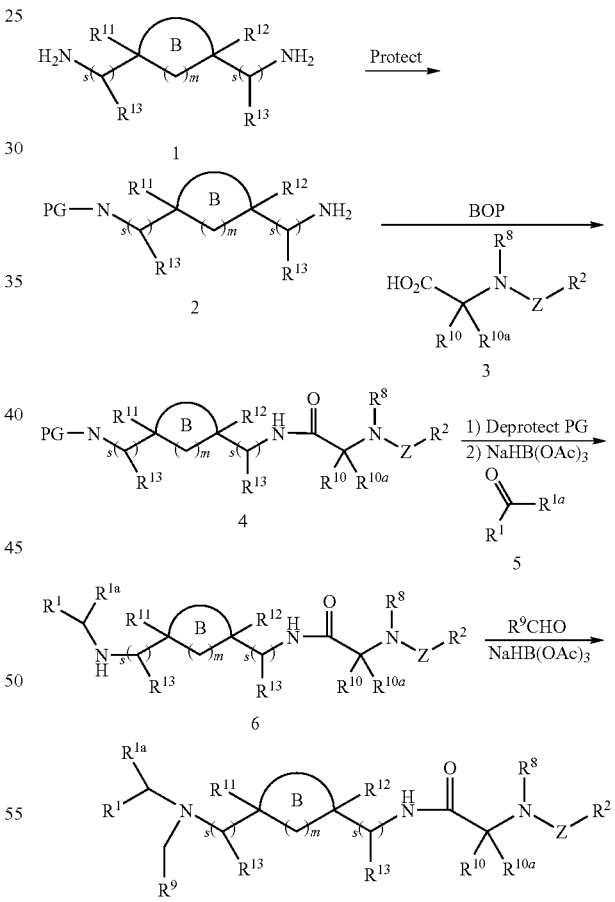

A series of compounds of formulas 10 and 11 are available as shown in Scheme 2. The protecting group on intermediate 4 can be removed, and a reductive amination can be performed to yield 8. This material can be coupled to acid 9 to give target 10. A second target can be synthesized by protecting group removal from intermediate 4 and direct coupling of 9 to give the target 11.

Scheme 2

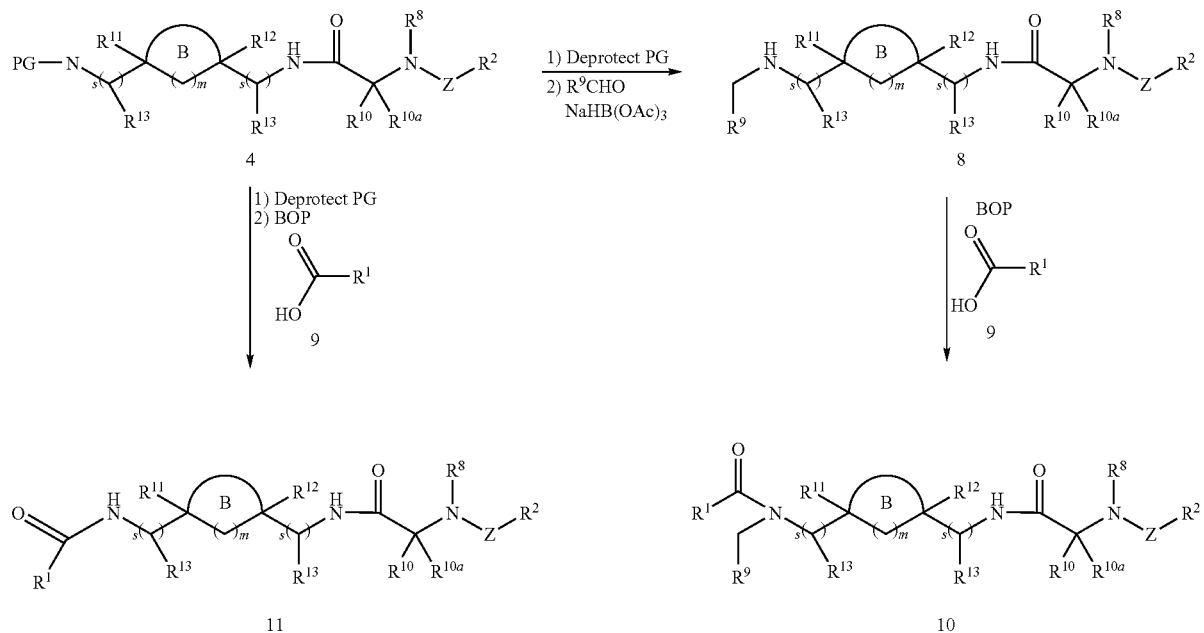

A series of compounds of formulas 20 and 21 are synthesized as shown in Scheme 3. A cyclic 1,2-diamine like 12 (for example, the commercially available 1,2-diaminocyclohexane) can be mono-protected as a Boc carbamate via BOC-ON (Brechbiel et al., *Bioorg. Med. Chem* . 1997, 5, 1925). The amine 13 can be directly coupled with 14 to yield the amide 15. In a second pathway, or a stepwise version, 13 can be coupled to 16 as the first step. The resulting amide 17 can be deprotected (N-Cbz), and then coupled to 9a to form the same 15. The N-Boc of 15 can be removed to give the key intermediate amine 19. One target can be synthesized via a reductive amination with 5 to yield 20. The second target can be synthesized by performing another reductive amination to give 21.

Scheme 3

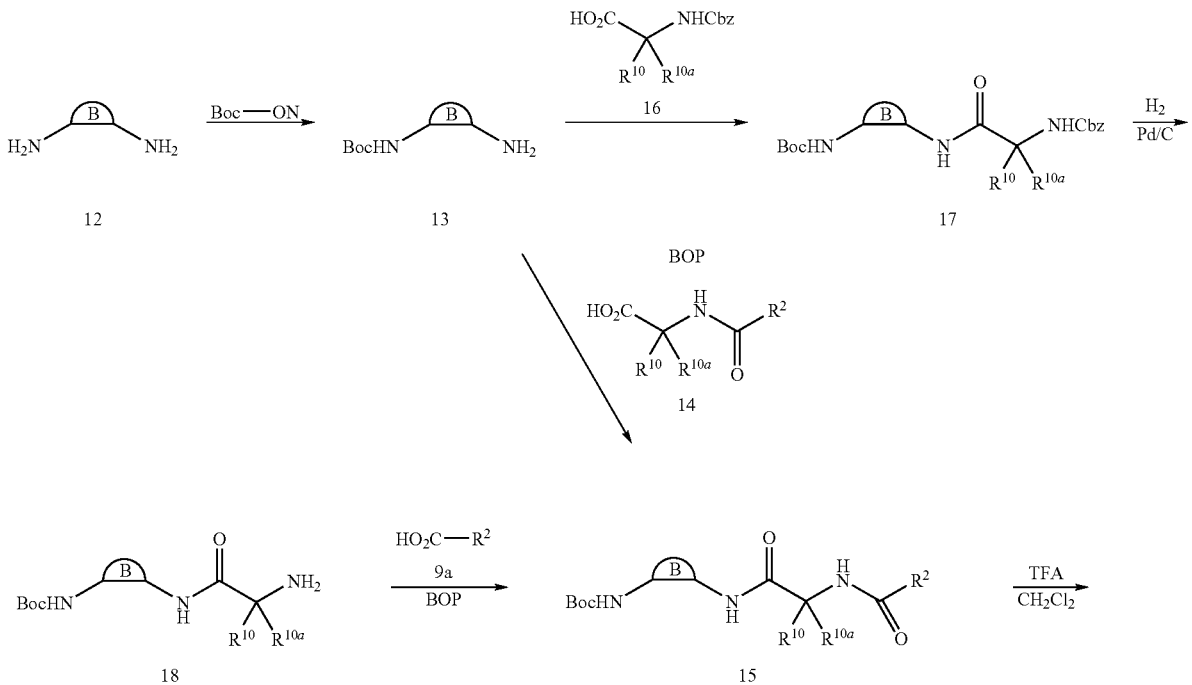

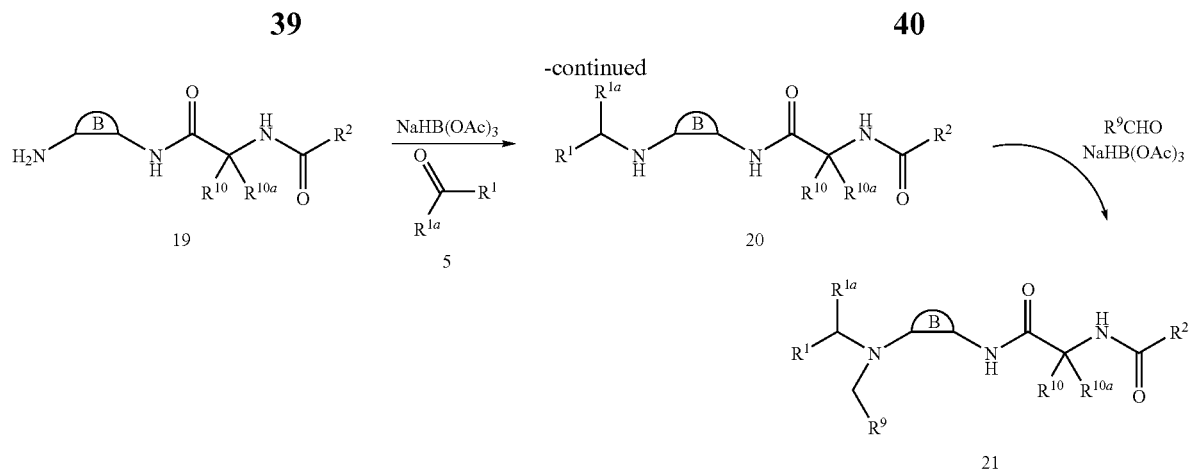

A series of compounds of formulas 23 and 24 can be synthesized as shown in Scheme 4. The key intermediate 19 can be alkyated via reductive amination to give 22. The first target can be synthesized by coupling 22 with 9 to give 23. The second target can be synthesized by direct coupling of 19 with 9 to afford 24.

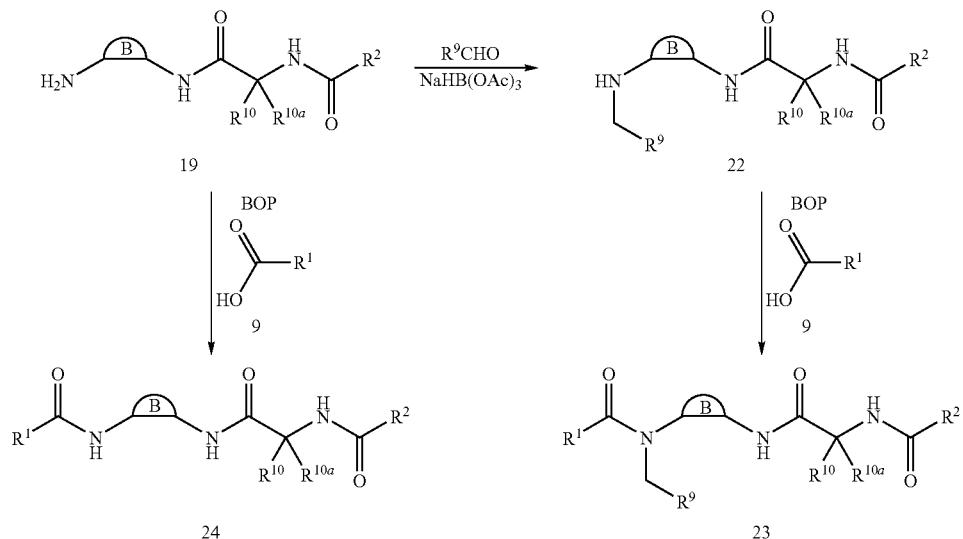

A series of compounds of formulas 32 and 34 are prepared via the methods shown in Scheme 5. An amine 25 (for example, the commercially available 2-benzyloxycyclopentylamine) can be protected as the carbamate 26 via Boc$_2$O. Removal of the benzyl group affords the alcohol 27, which can be converted to the mesylate 28. The mesylate can be displaced with NaN$_3$ to provide the azide 29. This can be reduced to the key intermediate 30. This amine can be coupled with 9 to afford the amide 31. The first target can be synthesized by deprotection with TFA followed by coupling with 3 to give 32. Another target can be synthesized from 30 by first performing a reductive amination to give 33. The amine 33 can be coupled to 9, deprotected with TFA, and coupled with 3 to afford the target 34.

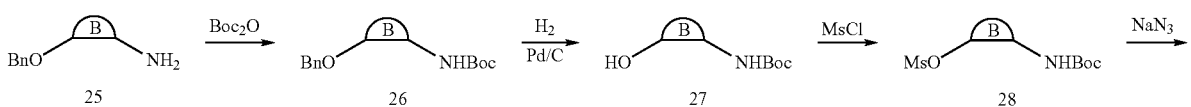

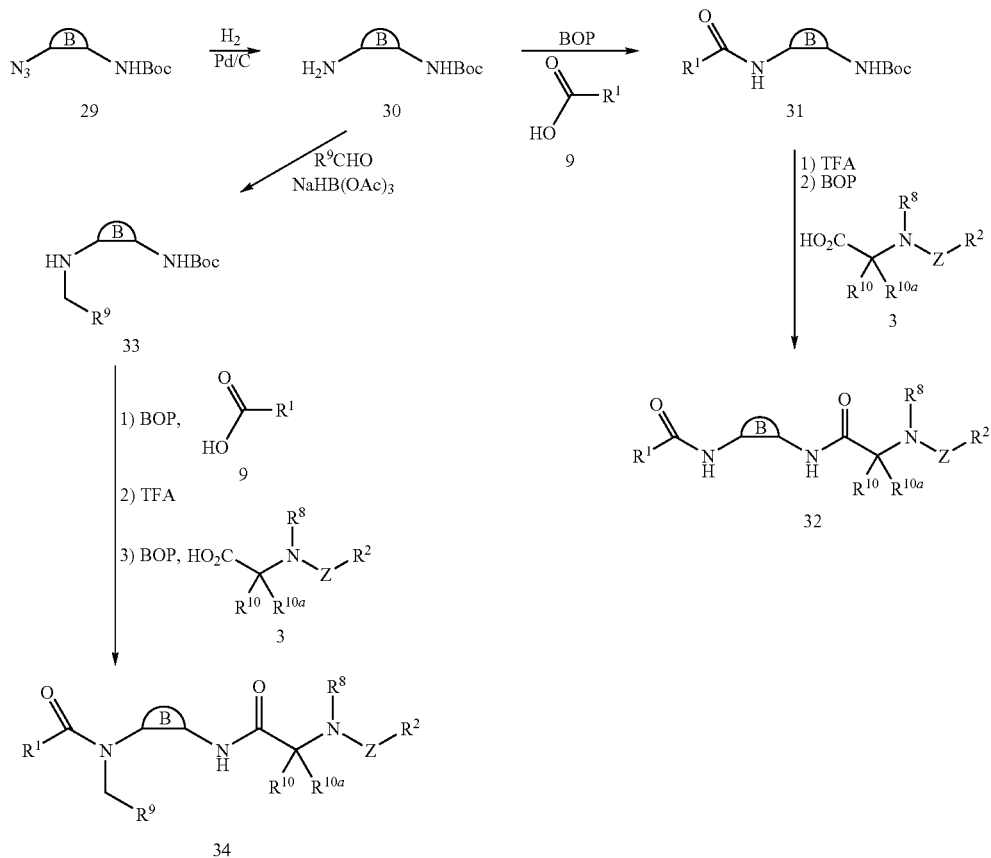

A series of compounds of formulas 39 and 40 are synthesized as shown in Scheme 6. The key intermediate 30 can be protected as the Cbz carbamate 35 via Cbz$_2$O. The Boc group can be removed, and the acid 3 can be coupled to provide amide 37. The amide 37 can be deprotected to the amine 38, and a reductive amination can be performed to give the first target 39. The second target can be synthesized via another reductive amination on 39 to afford 40.

Scheme 6

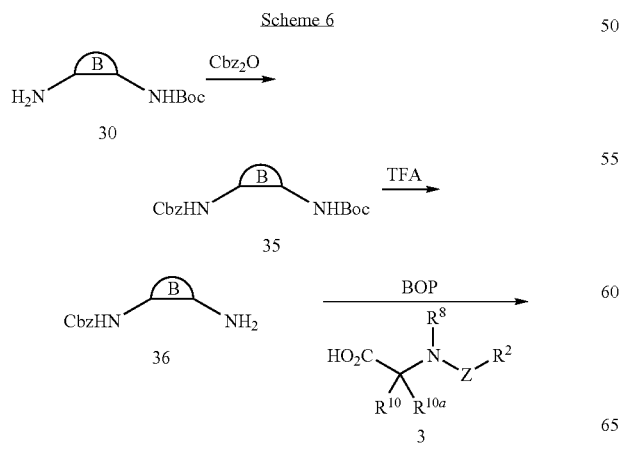

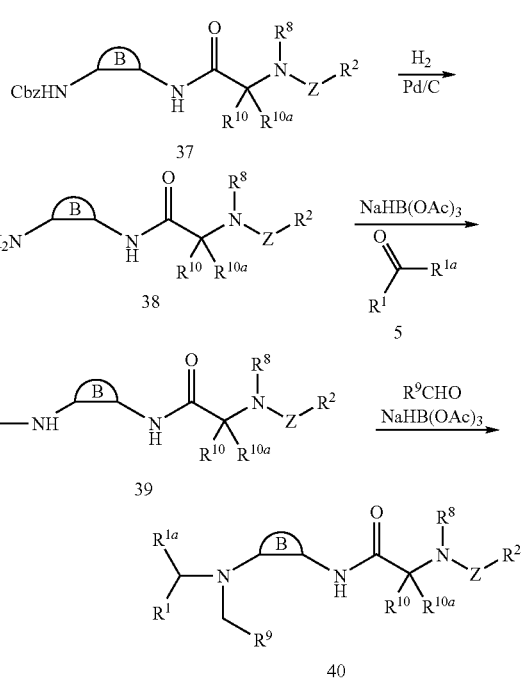

As shown in Schemes 5 and 6, intermediate 30 can be converted into several target molecules. As a key intermediate, 30 can be synthesized several different ways. As shown in Scheme 7, a cyclic olefin 41 [many are available for this: 1-carbobenzyloxy-1,2,3,6-tetrahydropyridine (D'Andrea et al., *J. Org. Chem.* 1991, 56, 3133), 4-aminocyclohexene derivatives (Bisagni et al., *J. Heterocycl. Chem.* 1990, 27, 1801 or Pfister et al. *Synthesis* 1983, 38-40), or 3-pyrroline derivatives (Lai et al., *J. Med. Chem.* 1997, 40, 226)] can be oxidized to the epoxide 42 (Jacobsen et al., *J. Org. Chem.* 1997, 62, 4197). This can be opened with NaN₃ to give the azide 43, which can be reduced. The resulting amine 44 can be protected as the N-Boc 45. This can be converted to the mesylate 46 and then the azide 47. In the final step, the azide 47 can be reduced to the key intermediate 30.

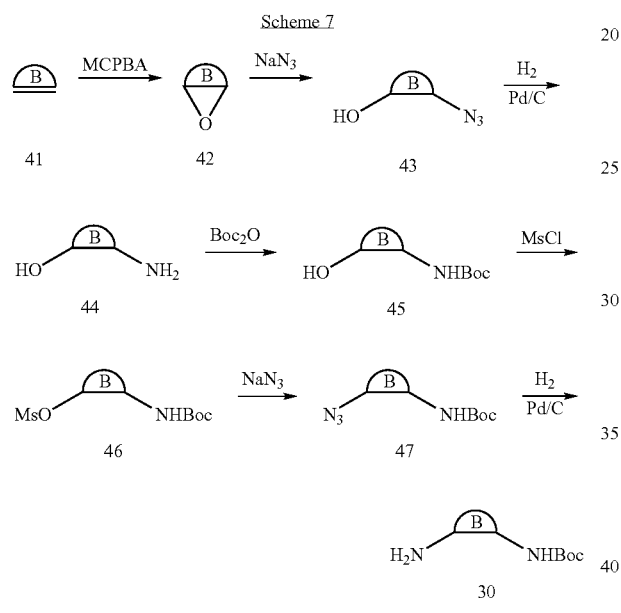

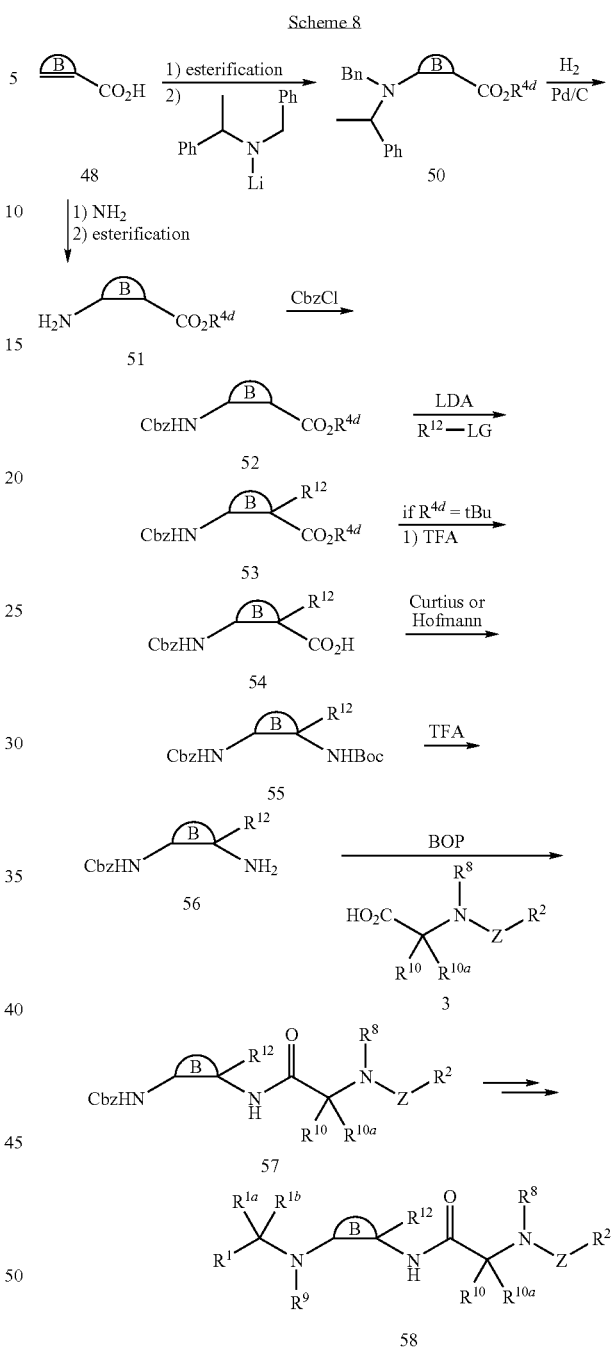

A series of compounds of formula 58 are synthesized as shown in Scheme 8. The cyclic, unsaturated acid 48 can be converted into the 2-aminocyclocarboxylate 51 via two routes. In the first route, esterification followed by a Michael reaction (Davies et al., *J. Chem. Soc. Perkin Trans. I*, 1994, 1411) gives 50. Simple hydrogenation gives the 2-aminocyclocarboxylate 51. In the second route, the Michael reaction (Schneider et al., *Chem Ber.* 1959, 92, 1594) can be performed with ammonia to give 51 after esterification. Going forward, a Cbz group (or another appropriate protecting group) can be installed under standard conditions to afford 52. Enolization of the ester with LDA (or another appropriate base) followed by alkylation gives the substituted 53. The ester is then removed to afford the free acid 54. A Curtius (Yamada et al., *Tetrahedron* 1974, 30, 2151) or Hofmann reaction (Zhang et al., *J. Org. Chem.* 1997, 62, 6918) can then be performed to give the diamino derivative 55 (as in 35, Scheme 6). After removal of the Boc group, the right-side piece 3 can be coupled on to give the amide 57. This can be elaborated as shown in Scheme 3, 4, 5, and 6 to give the desired target 58.

A series of comounds of formula 64 are synthesized as shown in Scheme 9. In this case, intermediate 52 (or another appropriate protecting group for Cbz) from Scheme 8 can be used as a starting point. Enolization of the ester with LDA (or another appropriate base) followed by alkylation gives the substituted 59. The ester is then removed to afford the free acid 60. A Curtius (Yamada et al., *Tetrahedron* 1974, 30, 2151) or Hofmann reaction (Zhang et al., *J. Org. Chem.* 1997, 62, 6918) can then be performed to give the diamino derivative 61 (as in 35, Scheme 6). The Cbz can be removed via hydrogenation to give the free amine 62. As before, this material can be coupled to the right-side piece 3 to give the amide 63. This can then be elaborated as shown in Scheme 3, 4, 5, and 6 to give the desired target 64.

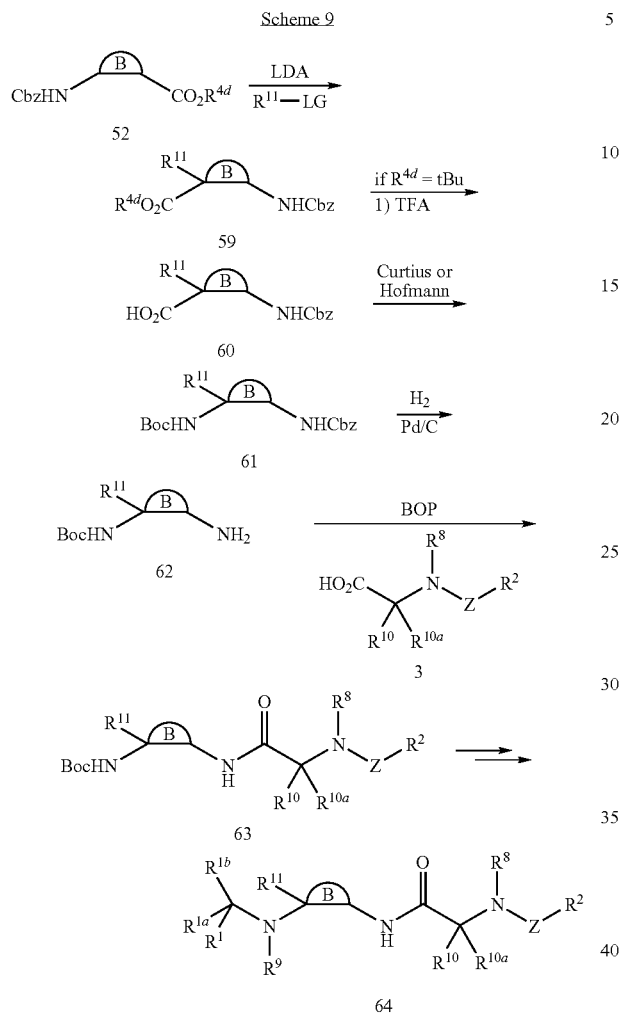

A series of compounds of formula 74 are synthesized as shown in Scheme 10. A cyclic ester acid 65 can be alkylated with LDA (or another appropriate base) and the electrophile $R^{11}$-LG to give 66. This material can be esterified via the isourea (Mathias *Synthesis* 1979, 561) to afford the diester 67. Hydrolysis leads to the acid 68, which can undergo a Curtius or a Hofmann to give 69 (or another appropriate protecting group for Cbz). Once again, the ester can be alkylated with the electrophile $R^{12}$-LG to provide 70. The tert-butyl ester can be removed to the acid 71, and a Curtius or Hofmann reaction provides the amine 72 (much like 35, Scheme 6). As before, 72 can be coupled to the right-side piece 3 to give the amide 73. This can then be elaborated as shown in Scheme 3, 4, 5, and 6 to give the desired target 74.

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602-2605.

Other features of the invention will become apparent in the course of the following descriptions of exemplary embodiments which are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "g" for gram or grams, "mg" for milligram or milligrams, "mL" for milliliter or milliliters, "¹H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "R" and "S" are stereochemical designations familiar to those skilled in the art.

Example 1

N-[2-[[(1S,2S)-2-[[(4-Chlorophenyl)methyl]amino]cyclohexyl]amino]-2-oxoethyl]-3-(trifluoromethyl)benzamide (1a) N-tert-Butyloxycarbonyl-cyclohexane-(S,S)-1,2-diamine (C. Wu et al., *Bioorg. Med. Chem.* 1997, 5, 1925) (3.0 g) was dissolved in DMF prior to the addition of, 4-methylmorpholine (7.7 mL) and [[3-(trifluoromethyl)benzoyl]amino]acetic acid (3.8 g). This solution was cooled to 0° C., and BOP (6.8 g) was added in portions. The reaction was warmed to rt and was stirred overnight. The reaction was quenched with water and EtOAc. The EtOAc layer was washed with 1 N HCl solution, NaHCO$_3$ solution, and brine. The organic layer was dried, filtered, and concentrated. Flash chromatography of the resulting residue gave the N-Boc derivative [(1S,2S)-2-[[[[3-(trifluoromethyl)benzoyl]amino]acetyl]amino]cyclohexyl]carbamic acid 1,1-dimethylethyl ester (5.0 g). MS found: (M+Na)$^+$=466.3.

(1b) The above derivative (1a)(5.0 g) was dissolved in CH$_2$Cl$_2$ (10 mL) and cooled to 0° C. Trifluoroacetic acid (10 mL) was added and the reaction was warmed to rt. After 1 h, the solvent was removed to give an oily residue. This was re-dissolved in CH$_2$Cl$_2$ and then re-concentrated to the amine N-[2-[[(1S,2S)-2-aminocyclohexyl]amino]-2-oxoethyl]-3-(trifluoromethyl)benzamide (5.0 g). MS found: (M+H)$^+$=344.3.

(1c) The above amine (1b)(110 mg) was dissolved in THF prior to the addition of Hunigs's base (0.2 mL). Next, 4-chlorobenzaldehyde (30 mg) was added along with 4A molecular sieves. After 3 h, NaHB(OAc)$_3$ (76 mg) was added. This mixture was stirred an additional 2 h before the reaction was quenched with NaHCO$_3$ solution. This was extracted with EtOAc. The EtOAc was dried and concentrated. Reverse phase HPLC purification (gradient elution, water/acetonitrile/TFA) of the resulting residue provided the title benzamide N-[2-[[(1S,2S)-2-[[(4-chlorophenyl)methyl]amino]cyclohexyl]amino]-2-oxoethyl]-3-(trifluoromethyl)benzamide (30 mg). MS found: (M+H)$^+$=468.2.

Example 2

N-[2-[[(1S,2S)-2-[[(2,4-Dimethylphenyl)methyl]amino]cyclohexyl]amino]-2-oxoethyl]-3-(trifluoromethyl)benzamide (2a) 2,4-Dimethylbenzaldehyde (0.04 mL) was incorporated into the above procedure, (1c), to give the title benzamide (35 mg). MS found: (M+H)$^+$=462.3.

Example 3

N-[2-[[(1S,2S)-2-[[(2,4,6-Trimethylphenyl)methyl]amino]cyclohexyl]amino]-2-oxoethyl]-3-(trifluoromethyl)benzamide (3a) 2,4,6-trimethylbenzaldehyde (0.07 mL) was incorporated into the above procedure, (1c), to give the title benzamide (30 mg). MS found: (M+H)$^+$=476.4.

Example 4

N-[2-[[(1S,2S)-2-[[(4-Benzyloxyphenyl)methyl]amino]cyclohexyl]amino]-2-oxoethyl]-3-(trifluoromethyl)benzamide (4a) 4-Benzyloxybenzaldehyde (108 mg) was incorporated into the above procedure, (1c), to give the title benzamide (40 mg). MS found: (M+H)$^+$=540.4.

Example 5

N-[2-[[(1S,2S)-2-[[(2,4-Difluorophenyl)methyl]amino]cyclohexyl]amino]-2-oxoethyl]-3-(trifluoromethyl)benzamide (5a) 2,4-Difluorobenzaldehyde (0.06 mL) was incorporated into the above procedure, (1c), to give the title benzamide (25 mg). MS found: (M+H)$^+$=470.3.

Example 6

N-[2-[[(1S,2S)-2-[[(2-Chloro-4-fluorophenyl)methyl]amino]cyclohexyl]amino]-2-oxoethyl]-3-(trifluoromethyl)benzamide (6a) 2-Chloro-4-fluorobenzaldehyde (75 mg) was incorporated into the above procedure, (1c), to give the title benzamide (15 mg). MS found: (M+H)$^+$=486.2.

Example 7

N-[2-[[(1S,2S)-2-[[(2-Trifluoromethyl-4-fluorophenyl)methyl]amino]cyclohexyl]amino]-2-oxoethyl]-3-(trifluoromethyl)benzamide (7a) 2-Trifluoromethyl-4-fluorobenzaldehyde (0.06 mL) was incorporated into the above procedure, (1c), to give the title benzamide (20 mg). MS found: (M+H)$^+$=520.2.

Example 8

N-[2-[[(1S,2S)-2-[[(2,4-Dichlorophenyl)methyl]amino]cyclohexyl]amino]-2-oxoethyl]-3-(trifluoromethyl)benzamide (8a) 2,4-Dichlorobenzaldehyde (91 mg) was incorporated into the above procedure, (1c), to give the title benzamide (10 mg). MS found: (M+H)$^+$=502.1.

Example 9

N-[2-[[(1S,2S)-2-[[(2-Fluoro-6-trifluoromethylphenyl)methyl]amino]cyclohexyl]amino]-2-oxoethyl]-3-(trifluoromethyl)benzamide (9a) 2-Fluoro-6-trifluoromethylbenzaldehyde (0.06 mL) was incorporated into the above procedure, (1c), to give the title benzamide (30 mg). MS found: (M+H)$^+$=520.2.

Example 10

N-[2-[[(1S,2S)-2-[[(2-Chloro-5-trifluoromethylphenyl)methyl]amino]cyclohexyl]amino]-2-oxoethyl]-3-(trifluoromethyl)benzamide (10a) 2-Chloro-5-trifluoromethylbenzaldehyde (0.083 mL) was incorporated into the above procedure, (1c), to give the title benzamide (20 mg). MS found: (M+H)$^+$=536.2.

Example 11

N-[2-[[(1S,2S)-2-[[(1-Naphthyl)methyl]amino]cyclohexyl]amino]-2-oxoethyl]-3-(trifluoromethyl)benzamide (11a) 1-Naphthaldehyde (0.05 mL) was incorporated into the above procedure, (1c), to give the title benzamide (6 mg). MS found: (M+H)$^+$=484.3.

Example 12

N-[2-[[(1S,2S)-2-[bis (3-furylmethyl)amino]cyclohexyl]amino]-2-oxoethyl]-3-(trifluoromethyl)benzamide (12a) 3-Furaldehyde (0.03 mL) was incorporated into the above procedure, (1c), to give the title benzamide (30 mg). MS found: (M+H)$^+$=504.3.

Example 13

N-[2-[[(1S,2S)-2-[(2,4-Dimethylbenzyl)(methyl)amino]cyclohexyl]amino]-2-oxoethyl]-3-(trifluoromethyl)benzamide (13a) The title benzamide from Example (2a)(25 mg) was dissolved in THF prior to the addition of Hunigs's base (0.01 mL). Next, 37% formaldehyde (0.02 mL) was added along with 4A molecular sieves. After 3 h, NaHB(OAc)$_3$ (46 mg) was added. This mixture was stirred an additional 2 h before the reaction was quenched with NaHCO$_3$ solution. This was extracted with EtOAc. The EtOAc was dried and concentrated. Reverse phase HPLC purification (gradient elution, water/acetonitrile/TFA) of the resulting residue provided the title benzamide N-[2-[[(1S,2S)-2-[(2,4-dimethylbenzyl)(methyl)amino]cyclohexyl]amino]-2-oxoethyl]-3-(trifluoromethyl)benzamide (10 mg). MS found: (M+H)$^+$=476.3.

Example 14

N-[2-[[(1S,2S)-2-[(4-Chlorobenzyl)(methyl)amino]cyclohexyl]amino]-2-oxoethyl]-3-(trifluoromethyl)benzamide (14a) The title benzamide from Example 1 (21 mg) was dissolved in THF prior to the addition of Hunigs's base (0.01 mL). Next, 37% formaldehyde (0.017 mL) was added along with 4A molecular sieves. After 3 h, NaHB(OAc)$_3$ (38 mg) was added. This mixture was stirred an additional 2 h before the reaction was quenched-with NaHCO$_3$ solution. This was extracted with EtOAc. The EtOAc was dried and concentrated. Reverse phase HPLC purification (gradient elution, water/acetonitrile/TFA) of the resulting residue provided the title benzamide N-[2-[[(1S,2S)-2-[(4-chlorobenzyl)(methyl)amino]cyclohexyl]amino]-2-oxoethyl]-3-(trifluoromethyl)benzamide (10 mg). MS found: (M+H)$^+$=482.3.

Example 15

N-[2-[[(cis)-2-[[(2,4-Dimethylphenyl)methyl]amino]cyclohexyl]amino]-2-oxoethyl]-3-(trifluoromethyl)benzamide (15a) 1-(N-tert-Butyloxycarbonyl)-cis-cyclohexane-1,2-diamine (prepared in an analogous fashion to N-tert-butyloxycarbonyl-cyclohexane-(S,S)-1,2-diamine see: C. Wu et al., *Bioorg. Med. Chem.* 1997, 5, 1925) was substituted into Example 1, step (1a), and 2,4-dimethylbenzaldehyde (0.1 mL) was substituted into step (1c) to give the title benzamide N-[2-[[(cis)-2-[[(2,4-dimethylphenyl)methyl]amino]cyclohexyl]amino]-2-oxoethyl]-3-(trifluoromethyl)benzamide (40 mg). MS found: (M+H)$^+$=462.4.

Example 16

N-[2-[[(cis)-2-[[(4-Chlorophenyl)methyl]amino]cyclohexyl]amino]-2-oxoethyl]-3-(trifluoromethyl)benzamide (16a) 4-Chlorobenzaldehyde (167 mg) was incorporated into Example 15 to give the title benzamide (30 mg). MS found: (M+H)$^+$=468.3.

Example 17

N-[2-[[(cis)-2-[[(4-Nitrophenyl)methyl]amino]cyclohexyl]amino]-2-oxoethyl]-3-(trifluoromethyl)benzamide (17a) 4-Nitrobenzaldehyde (67 mg) was incorporated into Example 15 to give the title benzamide (45 mg). MS found: (M+H)$^+$=479.3.

Example 18

N-[2-[[(cis)-2-[[(4-Isopropylphenyl)methyl]amino]cyclohexyl]amino]-2-oxoethyl]-3-(trifluoromethyl)benzamide (18a) 4-Isopropylbenzaldehyde (0.07 mL) was incorporated into Example 15 to give the title benzamide (20 mg). MS found: (M+H)$^+$=476.3.

Example 19

N-[2-[[(cis)-2-[[(4-Trifluorophenyl)methyl]amino]cyclohexyl]amino]-2-oxoethyl]-3-(trifluoromethyl)benzamide (19a) 4-Trifluorobenzaldehyde (0.05 mL) was incorporated into Example 15 to give the title benzamide (40 mg). MS found: (M+H)$^+$=502.3.

Example 20

N-[2-[[(cis)-2-[[(4-Trifluoromethoxyphenyl)methyl]amino]cyclohexyl]amino]-2-oxoethyl]-3-(trifluoromethyl)benzamide (20a) 4-Trifluoromethoxybenzaldehyde (0.09 mL) was incorporated into Example 15 to give the title benzamide (50 mg). MS found: (M+H)$^+$=518.2.

Example 21

N-[2-[[(cis)-2-[[(4-Phenoxyphenyl)methyl]amino]cyclohexyl]amino]-2-oxoethyl]-3-(trifluoromethyl)benzamide (21a) 4-Phenoxybenzaldehyde (0.1 mL) was incorporated into Example 15 to give the title benzamide (40 mg). MS found: (M+H)$^+$=526.2.

Example 22

N-[2-[[(cis)-2-[[(1-Naphthyl)methyl]amino]cyclohexyl]amino]-2-oxoethyl]-3-(trifluoromethyl)benzamide (22a) 1-Naphthaldehyde (0.05 mL) was incorporated into Example 15 to give the title benzamide (30 mg). MS found: $(M+H)^+=484.3$.

Example 23

N-[2-[[(cis)-2-[[(2-Naphthyl)methyl]amino]cyclohexyl]amino]-2-oxoethyl]-3-(trifluoromethyl)benzamide (23a) 2-Naphthaldehyde (53 mg) was incorporated into Example 15 to give the title benzamide (20 mg). MS found: $(M+H)^+=484.3$.

Example 24

N-[2-[[(cis)-2-[[(3-Indolyl)methyl]amino]cyclohexyl]amino]-2-oxoethyl]-3-(trifluoromethyl)benzamide (24a) Indole-3-carboxaldehyde (65 mg) was incorporated into Example 15 to give the title benzamide (10 mg). MS found: $(M+H)^+=473.3$.

Example 25

N-[2-[[(cis)-2-[[1-(4-Chlorophenyl)ethyl]amino]cyclohexyl]amino]-2-oxoethyl]-3-(trifluoromethyl)benzamide (25a) 2'-Chloroacetophenone (0.2 mL) was incorporated into Example 15 to give the title benzamide (20 mg). MS found: $(M+H)^+=482.2$.

Example 26

N-[2-[[(cis)-2-[Bis(3-furylmethyl)amino]cyclohexyl]amino]-2-oxoethyl]-3-(trifluoromethyl)benzamide (26a) 3-Furaldehyde (0.04 mL) was incorporated into Example 15 to give the title benzamide (30 mg). MS found: $(M+H)^+=504.3$.

Example 27

N-[2-[[(1S,2R)-2-[(4-Chlorobenzoyl)amino]cyclopentyl]amino]-2-oxoethyl]-3-(trifluoromethyl)benzamide (27a) (1S,2S)-1-Amino-2-benzyloxycyclopentane (12.1 g) (Lancaster Synthesis Inc.) was dissolved in THF prior to the addition of water (58 mL) and Et$_3$N (35.4 mL). After cooling to 0° C., Boc$_2$O (15.23 g) in THF (58 mL) was added dropwise. The reaction was warmed to rt and was stirred overnight. The THF was removed and EtOAc was added. This solution was washed with 1M HCl and brine. The EtOAc was dried (MgSO$_4$), filtered, and concentrated to give (1S,2S)-N-(t-butoxycarbonyl)-2-benzyloxycyclopentane (18.4 g). MS found: $(M+Na)^+=314.2$.

(27b) The above material (27a) (18.4 g) was dissolved in MeOH (90 mL) prior to the addition of 20% Pd(OH)$_2$/C. This reaction was placed on the Parr apparatus at 60 psi hydrogen pressure. After shaking 4.25 h, the Pd/C was filtered and the solution was concentrated (13.4 g). A portion of this material (12.7 g) was dissolved in CH$_2$Cl$_2$ prior to the addition of Et$_3$N (26.5 mL). After cooling to 0° C., MsCl (7.4 mL) was added dropwise. This continued stirring for 2.5 h, before water was added. The CH$_2$Cl$_2$ layer was also washed with NaHCO$_3$ solution and brine. The CH$_2$Cl$_2$ was dried (MgSO$_4$), filtered, and concentrated. This material was dissolved in DMF (180 mL) prior to the addition of NaN$_3$. The resulting solution was heated at 85° C. for 2 h. After cooling, EtOAc was added along with brine. The EtOAc was dried (MgSO$_4$), filtered, and concentrated to a solid. This solid was dissolved in MeOH (100 mL) prior to the addition of 10% Pd/C. A hydrogen balloon was attached, and the mixture stirred overnight. The Pd/C was filtered off, and the MeOH was removed to give (1S,2R)-1-(N-(t-butoxycarbonyl))-1,2-cyclopentanediamine (6 g). MS found: $(M+H)^+=201.4$.

(27c) 4-Chlorobenzoic acid (258 mg) was dissolved in DMF (8 mL) prior to the addition of Hunig's base (1.0 mL). After cooling to 0° C., BOP Reagent (729 mg) was added. This was stirred for 15 min before (1S,2R)-1-(N-(t-butoxycarbonyl))-1,2-cyclopentanediamine, (27b), (300 mg) was added as a DMF solution (2 mL). The resulting mixture warmed to rt and was stirred overnight. EtOAc was added along with 1 N HCl solution. The EtOAc layer was washed with 1 N HCl, NaHCO$_3$ solution, and brine. The EtOAc was dried (MgSO$_4$), filtered, and concentrated. The resulting material was dissolved in CH$_2$Cl$_2$ (10 mL) and cooled to 0° C. TFA (1.2 mL) was added and the reaction was stirred for 2 h. This solution was concentrated prior to the addition of DMF (8 mL). After cooling to 0° C., Hunig's base (1 mL) and [[3-(trifluoromethyl)benzoyl]amino]acetic acid (386 mg) were added. BOP Reagent (655 mg) was added next, and the mixture was stirred overnight. EtOAc was added along with 1 N HCl solution. The EtOAc layer was washed with 1 N HCl, NaHCO$_3$ solution, and brine. The EtOAc was dried (MgSO4), filtered, and concentrated. This was stirred in 1:1 EtOAc/hexane and then filtered to give the title benzamide N-[2-[[(1S,2R)-2-[(4-chlorobenzoyl)amino]cyclopentyl]amino]-2-oxoethyl]-3-(trifluoromethyl)benzamide (310 mg) as a solid. MS found: $(M+H)^+=468.2$.

Example 28

N-[2-[[(1S,2R)-2-[(4-(Methylthio)benzoyl)amino]cyclopentyl]amino]-2-oxoethyl]-3-(trifluoromethyl)benzamide (28a) 4-(Methylthio)benzoic acid (277 mg) was incorporated into Example 27, step (27c), to give the title benzamide (320 mg). MS found: $(M+H)^+=480.2$.

Example 29

N-[2-[[(1S,2R)-2-[(4-(Methylsulfonyl)benzoyl)amino]cyclopentyl]amino]-2-oxoethyl]-3-(trifluoromethyl)benzamide (29a) 4-(Methylsulfonyl)benzoic acid (330 mg) was incorporated into Example 27, step (27c), to give the title benzamide (209 mg). MS found: $(M+H)^+=512.1$.

Example 30

N-[2-[[(1S,2R)-2-[(4-Iodobenzoyl)amino]cyclopentyl]amino]-2-oxoethyl]-3-(trifluoromethyl)benzamide (30a) 4-Iodobenzoic acid (409 mg) was incorporated into Example 27, step (27c), and HPLC purification (gradient elution, water/acetonitrile/TFA) gave the title benzamide (20 mg). MS found: $(M+H)^+=431.0$.

Example 31

N-[2-[[(1S,2R)-2-[(4-(Aminosulfonyl)benzoyl)amino]cyclopentyl]amino]-2-oxoethyl]-3-(trifluoromethyl)benzamide (31a) 4-Carboxybenzenesulfonamide (79 mg) was incorporated into Example 27, step (27c), and the resulting residue was purified by reverse phase HPLC purification (gradient elution, water/acetonitrile/TFA) to provided the title benzamide (140 mg). MS found: $(M+Na)^+=535.1$.

Example 32

N-[2-[[(1S,2R)-2-[[(4-Chlorophenyl)methyl]amino]cyclopentyl]amino]-2-oxoethyl]-3-(trifluoromethyl)benzamide (32a) (1S,2R)-1-(N-(t-butoxycarbonyl))-1,2-cyclopentanediamine, (27b), (1.0 g) was dissolved in THF (5 mL) and water (5 mL) prior to the addition of Et₃N (2.8 mL). After cooling to 0° C., Cbz₂O (1.6 g) in THF was added. This mixture was warmed to rt and was stirred overnight. The THF was removed and EtOAc was added. The EtOAc layer was washed with 1 N HCl and brine. The EtOAc was dried (MgSO₄), filtered, and concentrated to a white solid (1.7 g). This white solid was dissolved in CH₂Cl₂ (20 mL) and cooled to 0° C. TFA (4 mL) was added and the reaction was stirred for 2 h. This solution was concentrated prior to the addition of DMF (10 mL). After cooling to 0° C., 4-methylmorpholine (2.2 mL) and [[3-(trifluoromethyl)benzoyl]amino]acetic acid (386 mg) were added. BOP Reagent (2.5 g) was added, and the mixture was stirred overnight. EtOAc was added along with 1 N HCl solution. The EtOAc layer was washed with 1 N HCl, NaHCO₃ solution, and brine. The EtOAc was dried (MgSO4), filtered, and concentrated. The resulting residue was purified by flash chromatography to afford the N-Cbz derivative [(1R,2S)-2-[[[[3-(trifluoromethyl)benzoyl]amino]acetyl]amino]cyclopentyl]carbamic acid phenylmethyl ester (1.3 g).

(32b) The above derivative (32a) (1.2 g) was dissolved in MeOH (100 mL) prior to the addition of 20% Pd(OH)₂ (240 mg). The solution was placed on a Parr shaker at 55 psi hydrogen pressure overnight. The Pd(OH)₂ was filtered off and the solution was concentrated. A portion of the resulting residue (132 mg) was dissolved in THF prior to the addition of acetic acid (0.23 mL) and 4-chlorobenzaldehyde (85 mg). After 45 min, NaHB(OAc)₃ was added. This mixture was stirred overnight before the solution was concentrated. EtOAc was added. The EtOAc layer was washed with NaHCO₃ solution. The EtOAc was dried (MgSO₄), filtered, and concentrated. Reverse phase HPLC purification (gradient elution, water/acetonitrile/TFA) of the resulting residue provided the title benzamide N-[2-[[(1S,2R)-2-[[(4-chlorophenyl)methyl]amino]cyclopentyl]amino]-2-oxoethyl]-3-(trifluoromethyl)benzamide (63 mg). MS found: $(M+H)^+=454.1$.

Example 33

N-[2-[[(1S,2R)-2-[[(2,4-Dimethylphenyl)methyl]amino]cyclopentyl]amino]-2-oxoethyl]-3-(trifluoromethyl)benzamide (33a) 2,4-Dimethylbenzaldehyde (0.1 mL) was incorporated into Example 32, step (32b), to give the title benzamide (47 mg). MS found: $(M+H)^+=448.2$.

Example 34

N-[2-[[(1S,2R)-2-[[(4-Methylphenyl)methyl]amino]cyclopentyl]amino]-2-oxoethyl]-3-(trifluoromethyl)benzamide (34a) 4-Methylbenzaldehyde (0.08 mL) was incorporated into Example 32, step (32b), to give the title benzamide (43 mg). MS found: $(M+H)^+=434.1$.

Example 35

N-[2-[[(cis)-2-[(4-Chlorobenzoyl)amino]cyclohexyl]amino]-2-oxoethyl]-3-(trifluoromethyl)benzamide (35a) 1-(N-tert-Butyloxycarbonyl)-cis-cyclohexane-1,2-diamine (prepared in an analogous fashion to N-tert-butyloxycarbonyl-cyclohexane-(S,S)-1,2-diamine, see: C. Wu et al., *Bioorg. Med. Chem.* 1997, 5, 1925) (5.0 g) was dissolved in DMF (70 mL). After cooling to 0° C., 4-methylmorpholine (7.7 mL) and [[3-(trifluoromethyl)benzoyl]amino]acetic acid (5.8 g) were added. BOP Reagent (11.3 g) was added, and the mixture was stirred overnight. EtOAc was added along with 1 N HCl solution. The EtOAc layer was washed with 1 N HCl, NaHCO₃ solution, and brine. The EtOAc was dried (MgSO₄), filtered, and concentrated. The resulting residue was purified by flash chromatography to afford the N-Boc derivative [(cis)-2-[[[[3-(trifluoromethyl)benzoyl]amino]acetyl]amino]cyclohexyl]carbamic acid 1,1-dimethylethyl ester (8.5 g). MS found: $(M+H)^+=444.1$.

(35b) A portion of the above derivative (35a) (5 g) was dissolved in CH₂Cl₂ (10 mL) and cooled to 0° C. TFA (10 mL) was added and the reaction was stirred for 2 h. This solution was concentrated and a portion (128 mg) was dissolved in DMF (5 mL). After cooling to 0° C., 4-methylmorpholine (0.15 mL) and 4-chlorobenzoic acid (53 mg) were added. BOP Reagent (136 mg) was added next, and the mixture was stirred overnight. EtOAc was added along with 1 N HCl solution. The EtOAc layer was washed with 1 N HCl, NaHCO₃ solution, and brine. The EtOAc was dried (MgSO₄), filtered, and concentrated. Reverse phase HPLC purification (gradient elution, water/acetonitrile/TFA) of the resulting residue provided the title benzamide N-[2-[[(cis)-2-[(4-chlorobenzoyl)amino]cyclohexyl]amino]-2-oxoethyl]-3-(trifluoromethyl)benzamide (30 mg). MS found: $(M+H)^+=482.2$.

Example 36

N-[2-[[(cis)-2-[(4-Methylbenzoyl)amino]cyclohexyl]amino]-2-oxoethyl]-3-(trifluoromethyl)benzamide (36a) 4-Methylbenzoic acid (41 mg) was incorporated into Example 35, step (35b), to give the title benzamide (40 mg). MS found: $(M+Na)^+=484.2$.

Example 37

N-[2-[[(cis)-2-[(4-Fluorobenzoyl)amino]cyclohexyl]amino]-2-oxoethyl]-3-(trifluoromethyl)benzamide (37a) 4-Fluorobenzoic acid (45 mg) was incorporated into Example 35, step (35b), to give the title benzamide (10 mg). MS found: (M+H)$^+$=466.2.

Example 38

N-[2-[[(cis)-2-[Benzoylamino]cyclohexyl]amino]-2-oxoethyl]-3-(trifluoromethyl)benzamide (38a) Benzoic acid (45 mg) was incorporated into Example 35, step (35b), to give the title benzamide (15 mg). MS found: (M+H)$^+$=448.2.

Example 39

N-[2-[[(cis)-2-[(4-Bromobenzoyl)amino]cyclohexyl]amino]-2-oxoethyl]-3-(trifluoromethyl)benzamide (39a) 4-Bromobenzoic acid (58 mg) was incorporated into Example 35, step (35b), to give the title benzamide (18 mg). MS found: (M+H)$^+$=528.1.

Example 40

N-[2-[[(cis)-2-[(4-Phenoxybenzoyl)amino]cyclohexyl]amino]-2-oxoethyl]-3-(trifluoromethyl)benzamide (40a) 4-Phenoxybenzoic acid (67 mg) was incorporated into Example 35, step (35b), to give the title benzamide (10 mg). MS found: (M+H)$^+$=540.2.

Example 41

N-[2-[[(cis)-2-[(4-Trifluoromethylbenzoyl)amino]cyclohexyl]amino]-2-oxoethyl]-3-(trifluoromethyl)benzamide (41a) 4-Trifluorobenzoic acid (67 mg) was incorporated into Example 35, step (35b), to give the title benzamide (38 mg). MS found: (M+H)$^+$=516.2.

Example 42

N-[2-[[(cis)-2-[(5-Benzotriazolecarbonyl)amino]cyclohexyl]amino]-2-oxoethyl]-3-(trifluoromethyl)benzamide (42a) Benzotriazole-5-carboxylic (45 mg) was incorporated into Example 35, step (35b), to give the title benzamide (8 mg). MS found: (M+H)$^+$=489.2.

Example 43

N-[2-[[(cis)-2-[(4-Iodobenzoyl)amino]cyclohexyl]amino]-2-oxoethyl]-3-(trifluoromethyl)benzamide (43a) 4-Iodobenzoic acid (74 mg) was incorporated into Example 35, step (35b), to give the title benzamide (25 mg). MS found: (M+H)$^+$=574.2.

Example 44

N-[2-[[(cis)-2-[(4-Cyanobenzoyl)amino]cyclohexyl]amino]-2-oxoethyl]-3-(trifluoromethyl)benzamide (44a) 4-Cyanobenzoic acid (49 mg) was incorporated into Example 35, step (35b), to give the title benzamide (40 mg). MS found: (M+H)$^+$=473.3.

Example 45

N-[2-[[(cis)-2-[(4-Trifluoromethoxybenzoyl)amino]cyclohexyl]amino]-2-oxoethyl]-3-(trifluoromethyl)benzamide (45a) 4-Trifluoromethoxybenzoic acid (55 mg) was incorporated into Example 35, step (35b), to give the title benzamide (15 mg). MS found: (M+H)$^+$=532.2.

Example 46

N-[2-[[(cis)-2-[(4-Formylbenzoyl)amino]cyclohexyl]amino]-2-oxoethyl]-3-(trifluoromethyl)benzamide (46a) 4-Formylbenzoic acid (36 mg) was incorporated into Example 35, step (35b), to give the title benzamide (10 mg). MS found: (M+H)$^+$=476.3.

Example 47

N-[2-[[(cis)-2-[(4-Carbomethoxybenzoyl)amino]cyclohexyl]amino]-2-oxoethyl]-3-(trifluoromethyl)benzamide (47a) 4-Carbomethoxybenzoic acid (38 mg) was incorporated into Example 35, step (35b), to give the title benzamide (55 mg). MS found: (M+H)$^+$=506.2.

Example 48

N-[2-[[(cis)-2-[(4-Nitrobenzoyl)amino]cyclohexyl]amino]-2-oxoethyl]-3-(trifluoromethyl)benzamide (48a) 4-Nitrobenzoic acid (140 mg) was incorporated into Example 35, step (35b), to give the title benzamide (200 mg). MS found: (M+H)$^+$=493.2.

Example 49

N-[2-[[(cis)-2-[(4-Aminobenzoyl)amino]cyclohexyl]amino]-2-oxoethyl]-3-(trifluoromethyl)benzamide (49a) The above material, Example 48, (10 mg) was dissolved in MeOH prior to the addition of 10% Pd/C. A hydrogen balloon was attached and the mixture was stirred overnight. The Pd/C was filtered off and the MeOH removed to give the title benzamide N-[2-[[(cis)-2-[(4-aminobenzoyl)amino]cyclohexyl]amino]-2-oxoethyl]-3-(trifluoromethyl)benzamide (5 mg). MS found: (M+H)$^+$=463.2.

Example 50

N-[2-[[(cis)-2-[(4-Methoxybenzoyl)amino]cyclohexyl]amino]-2-oxoethyl]-3-(trifluoromethyl)benzamide (50a) 4-Methoxybenzoic acid (31 mg) was incorporated into Example 35, step (35b), to give the title benzamide (47 mg). MS found: (M+H)$^+$=478.3.

Example 51

N-[2-[[(cis)-2-[(4-Methylthiobenzoyl)amino]cyclo-hexyl]amino]-2-oxoethyl]-3-(trifluoromethyl)benzamide (51a) 4-Methylthiobenzoic acid (38 mg) was incorporated into Example 35, step (35b), to give the title benzamide (10 mg). MS found: $(M+H)^+=494.2$.

Example 52

N-[2-[[(cis)-2-[(4-Methylsulfonylbenzoyl)amino] cyclohexyl]amino]-2-oxoethyl]-3-(trifluoromethyl) benzamide (52a) 4-Methylsulfonylbenzoic acid (45 mg) was incorporated into Example 35, step (35b), to give the title benzamide (40 mg). MS found: $(M+H)^+=526.2$.

Example 53

N-[2-[[(cis)-2-[(4-Aminosulfonylbenzoyl)amino] cyclohexyl]amino]-2-oxoethyl]-3-(trifluoromethyl) benzamide (53a) 4-Aminosulfonylbenzoic acid (50 mg) was incorporated into Example 35, step (35b), to give the title benzamide (40 mg). MS found: $(M+H)^+=527.2$.

Example 54

N-[2-[[(cis)-2-[(4-Isopropylbenzoyl)amino]cyclo-hexyl]amino]-2-oxoethyl]-3-(trifluoromethyl)benzamide (54a) 4-Isopropylbenzoic acid (45 mg) was incorporated into Example 35, step (35b), to give the title benzamide (30 mg). MS found: $(M+H)^+=490.3$.

Example 55

N-[2-[[(cis)-2-[(4-Phenylthiobenzoyl)amino]cyclo-hexyl]amino]-2-oxoethyl]-3-(trifluoromethyl)benzamide (55a) 4-Phenylthiobenzoic acid (63 mg) was incorporated into Example 35, step (35b), to give the title benzamide (27 mg). MS found: $(M+H)^+=556.2$.

Example 56

N-[2-[[(cis)-2-[(4-(N,N-diethylsulfamoyl)benzoyl) amino]cyclohexyl]amino]-2-oxoethyl]-3-(trifluoromethyl)benzamide (56a) N,N-Diethyl-4-sulfamoylbenzoic acid (63 mg) was incorporated into Example 35, step (35b), to give the title benzamide (30 mg). MS found: $(M+H)^+=583.3$.

Example 57

N-[2-[[(cis)-2-[(4-Trifluoromethylthiobenzoyl) amino]cyclohexyl]amino]-2-oxoethyl]-3-(trifluoromethyl)benzamide (57a) 4-Trifluoromethylthiobenzoic acid (117 mg) was incorporated into Example 35, step (35b), to give the title benzamide (20 mg). MS found: $(M+H)^+=548.2$.

Example 58

N-[2-[[(cis)-2-[[(4-Chlorophenyl)methyl]amino] cyclopropyl]amino]-2-oxoethyl]-3-(trifluoromethyl) benzamide (58a) 1-(N-(t-butoxycarbonyl))-1,2-(cis)-cyclopropanediamine hydrogen chloride (Langlois et al, *Bioorg. Med. Chem.* 2000, 8, 321) (850 mg) was dissolved in DMF (10 mL). After cooling to 0° C., 4-methylmorpholine (2.7 mL) and [[3-(trifluoromethyl)benzoyl]amino]acetic acid (1.4 g) were added. BOP Reagent (2.4 g) was added, and the mixture was stirred overnight. EtOAc was added along with 1 N HCl solution. The EtOAc layer was washed with 1 N HCl, NaHCO₃ solution, and brine. The EtOAc was dried (MgSO₄), filtered, and concentrated. The resulting residue was purified by flash chromatography to afford the N-Boc derivative [(cis)-2-[[[3-(trifluoromethyl)benzoyl]amino]acetyl]amino]cyclopropyl] carbamic acid 1,1-dimethylethyl ester (1.5 g). MS found: $(M+Na)^+=424.1$.

(58b) The above derivative (58a) (1.2 g) was dissolved in CH₂Cl₂ and cooled to 0° C. Trifluoroacetic acid was added and the reaction was warmed to rt. After 2 h, the solvent was removed. A portion of the resulting residue (100 mg) was dissolved in THF prior to the addition of acetic acid (0.014 mL), 4-chlorobenzaldehyde (34 mg), and 4A molecular sieves (100 mg). After 30 min, NaHB(OAc)₃ (76 mg) was added, and the mixture was stirred overnight at rt. EtOAc and NaHCO₃ solution were added. This was extracted with EtOAc. The EtOAc was dried and concentrated. Reverse phase HPLC purification (gradient elution, water/acetonitrile/TFA) of the resulting residue provided the title benzamide, N-[2-[[(cis)-2-[[(4-Chlorophenyl)methyl]amino]cyclopropyl]amino]-2-oxoethyl]-3-(trifluoromethyl) benzamide (10 mg). MS found: $(M+H)^+=550.1$.

Example 59

N-[2-[[(cis)-2-[[(3,4-Dimethylphenyl)methyl]amino] cyclopropyl]amino]-2-oxoethyl]-3-(trifluoromethyl) benzamide (59a) 3,4-Dimethylbenzaldehyde (0.03 mL) was incorporated into Example 58, step (58b), to give the title benzamide (20 mg). MS found: $(M+H)^+=420.1$.

Example 60

N-[2-[[(cis)-2-[[(4-Methylphenyl)methyl]amino] cyclopropyl]amino]-2-oxoethyl]-3-(trifluoromethyl) benzamide (60a) 4-Methylbenzaldehyde (28 mg) was incorporated into Example 58, step (58b), to give the title benzamide (10 mg). MS found: $(M+H)^+=406.1$.

Example 61

2-Amino-N-[2-[[(cis)-2-[[(4-(aminosulfonyl)benzoyl]amino]cyclohexyl]amino]-2-oxoethyl]-5-iodobenzamide (61a) 1-(N-tert-Butyloxycarbonyl)-cis-cyclohexane-1,2-diamine (prepared in an analogous fashion to N-tert-butyloxycarbonyl-cyclohexane-(S,S)-1,2-diamine, see: C. Wu et al., *Bioorg. Med. Chem.* 1997, 5, 1925) (10.7 g) was dissolved in DMF (167 mL). After cooling to 0° C., diisopropylethylamine (35 mL) and N-Cbz-Gly-OH (12.1 g) were added. HATU Reagent (21.9 g) was added, and the mixture was stirred for 4 days (out of convenience). EtOAc was added along with 1 N HCl solution. The EtOAc layer was washed with 1 N HCl, NaHCO$_3$ solution, and brine. The EtOAc was dried (MgSO$_4$), filtered, and concentrated (14.6 g). The resulting residue was dissolved in CH$_2$Cl$_2$ (20 mL) prior to the addition of TFA (20 mL). After 15 min, the solution was concentrated to a foam. This material was dissolved in DMF (70 mL). After cooling to 0° C., diisopropylethylamine (25 mL) and 4-aminosulfonylbenzoic acid (8.7 g) were added. BOP Reagent (19.2 g) was added, and the mixture was stirred overnight. EtOAc was added along with 1 N HCl solution. The EtOAc layer was washed with 1 N HCl, NaHCO$_3$ solution, and brine. The EtOAc was dried (MgSO$_4$), filtered, and concentrated. CH$_2$Cl$_2$ was added and the off-white solid was collected to give benzyl (cis)-2-[(2-{[4-(aminosulfonyl)benzoyl]amino}cyclohexyl)amino]-2-oxoethylcarbamate (8.1 g). MS found: (M+H)$^+$=511.1.

(61b) The material from above benzyl (cis)-2-[(2-{[4-(aminosulfonyl)benzoyl]amino}cyclohexyl)amino]-2-oxoethylcarbamate (217 mg) was dissolved in 30% HBr/AcOH (5 mL) at rt. After 1 h, Et$_2$O was added and the solid was collected to give N-(cis)-{2-[(aminoacetyl)amino]cyclohexyl}-4-(aminosulfonyl)benzamide hydrogen bromide. MS found: (M+H)$^+$=355.2.

(61c) The above material, (61b), N-(cis)-{2-[(aminoacetyl)amino]cyclohexyl}-4-(aminosulfonyl)benzamide hydrogen bromide (59 mg) was dissolved in DMF (1 mL). After cooling to 0° C., diisopropylethylamine (0.1 mL) and 2-amino-5-iodobenzoic acid (43 mg) were added. BOP Reagent (72 mg) was added, and the mixture was stirred overnight. EtOAc was added along with NaHCO$_3$ solution. The EtOAc was dried (MgSO$_4$), filtered, and concentrated. Reverse phase HPLC purification (gradient elution, water/acetonitrile/TFA) of the resulting residue provided the title benzamide 2-amino-N-{2-[((cis)-2-{[4-(aminosulfonyl)benzoyl]amino}cyclohexyl)amino]-2-oxoethyl}-5-iodobenzamide (6 mg). MS found: (M+Na)$^+$=622.2.

Example 62

2-Amino-N-[2-[[(cis)-2-[[4-(aminosulfonyl)benzoyl]amino]cyclohexyl]amino]-2-oxoethyl]-5-chlorobenzamide (62a) 2-Amino-5-chlorobenzoic acid (65 mg) was incorporated into Example 61, step (61c), to give the title benzamide (8 mg). MS found: (M+Na)$^+$=530.3.

Example 63

N-[2-[[(cis)-2-[[4-(Aminosulfonyl)benzoyl]amino]cyclohexyl]amino]-2-oxoethyl]-3-chlorobenzamide (63a) 3-Chlorobenzoic acid (43 mg) was incorporated into Example 61, step (61c), to give the title benzamide (50 mg). MS found: (M+H)$^+$=515.2.

Example 64

N-[2-[[(cis)-2-[[4-(Aminosulfonyl)benzoyl]amino]cyclohexyl]amino]-2-oxoethyl]-3-trifluoromethoxy-benzamide (64a) 3-Trifluoromethoxybenzoic acid (57 mg) was incorporated into Example 61, step (61c), to give the title benzamide (47 mg). MS found: (M+H)$^+$=543.1.

Example 65

Tert-butyl 2-[({2-[((cis)-2-{[4-(aminosulfonyl)benzoyl]amino}cyclohexyl)amino]-2-oxoethyl}amino)carbonyl]-4-(trifluoromethyl)phenylcarbamate (65a) 2-(Tert-butoxycarbonyl)amino-5-trifluoromethylbenzoic acid (87 mg) (Takagishi et al., Synlett 1992, 360) was incorporated into Example 61, step (61c), to give the title benzamide (150 mg). MS found: (M+Na)$^+$=664.3.

Example 66

2-Amino-N-[2-[[(cis)-2-[[4-(aminosulfonyl)benzoyl]amino]cyclohexyl]amino]-2-oxoethyl]-5-trifluoromethylbenzamide trifluoroacetate (66a) The material from above, (65a), (125 mg) was dissolved in CH$_2$Cl$_2$ (5 mL) prior to the addition of TFA (5 mL). After 1 h, the solution was concentrated. Reverse phase HPLC purification (gradient elution, water/acetonitrile/TFA) of a portion (25 mg) of the resulting residue provided the title benzamide (10 mg). MS found: (M+Na)$^+$=564.2.

Example 67

4-(Aminosulfonyl)-N-((cis)-2-{[({[2-(trifluoromethyl)anilino]carbonyl}amino)acetyl]amino}cyclohexyl)benzamide (67a) N-(cis)-{2-[(aminoacetyl)amino]cyclohexyl}-4-(aminosulfonyl)benzamide hydrogen bromide, (61b), (100 mg) was dissolved in DMF (3 mL) prior to the addition of 4-methylmorpholine (0.13 mL) and 2-trifluoromethylphenyl isocyanate (0.05 mL). After stirring overnight, EtOAc was added and the solution was washed with 1N HCl. The EtOAc was dried, filtered, and concentrated. Reverse phase HPLC purification (gradient elution, water/acetonitrile/TFA) of the resulting residue provided the title benzamide (50 mg). MS found: (M+Na)$^+$=564.3.

Example 68

4-(Aminosulfonyl)-N-{(cis)-2-[({[(3-chlorophenyl)sulfonyl]amino}acetyl)amino]cyclohexyl}benzamide (68a) N-(cis)-{2-[(aminoacetyl)amino]cyclohexyl}-4-(aminosulfonyl)benzamide hydrogen bromide, (61b), (70 mg) was dissolved in DMF (2.5 mL) prior to the addition of 3-chlorobenzenesulfonyl chloride (51 mg). After stirring overnight, EtOAc was added and the solution was washed with 1N HCl. The EtOAc was dried, filtered, and concentrated. Reverse phase HPLC purification (gradient elution, water/acetonitrile/TFA) of the resulting residue provided the title benzamide (25 mg). MS found: (M+H)$^+$=530.1.

Example 69

Ethyl 2-[({2-[((cis)-2-{[4-(aminosulfonyl)benzoyl]amino}cyclohexyl)amino]-2-oxoethyl}amino)carbonyl]-4-(iodo)phenylcarbamate (69a) 2-(Ethyloxycarbonyl)amino-5-iodobenzoic acid (185 mg) was incorporated into Example 61, step (61c), to give the title phenylcarbamate (87 mg). MS found: (M–H)$^-$=670.9.

Example 70

Methyl 2-[({2-[((cis)-2-{[4-(aminosulfonyl)benzoyl]amino}cyclohexyl)amino]-2-oxoethyl}amino)carbonyl]-4-(iodo)phenylcarbamate (70a) 2-(Methyloxycarbonyl)amino-5-iodobenzoic acid (177 mg) was incorporated into Example 61, step (61c), to give the title phenylcarbamate (67 mg). MS found: (M–H)$^-$=656.9.

Example 71

Tert-butyl N-Methyl-2-[({2-[((cis)-2-{[4-(aminosulfonyl)benzoyl]amino}cyclohexyl)amino]-2-oxoethyl}amino)carbonyl]-4-(trifluoromethyl)phenylcarbamate (71a) N-Methyl-2-(Tert-butoxycarbonyl)amino-5-trifluoromethylbenzoic acid (106 mg) was incorporated into Example 61, step (61c), to give the title phenylcarbamate (50 mg). MS found: (M+Na)$^+$=678.2.

Example 72

Ethyl 2-[({2-[((cis)-2-{[4-(aminosulfonyl)benzoyl]amino}cyclohexyl)amino]-2-oxoethyl}amino)carbonyl]-4-(trifluoromethyl)phenylcarbamate (72a) 2-(Ethyloxycarbonyl)amino-5-trifluoromethyl benzoic acid (61 mg) was incorporated into Example 61, step (61c), to give the title phenylcarbamate (12 mg). MS found: (M+Na)$^+$=636.1.

Example 73

2-(Benzylamino)-N-[2-[[(cis)-2-[[4-(aminosulfonyl)benzoyl]amino]cyclohexyl]amino]-2-oxoethyl]-5-trifluoromethyl benzamide (73a) 2-(Benzylamino)-5-trifluoromethyl benzoic acid (65 mg) was incorporated into Example 61, step (61c), to give the title benzamide (45 mg). MS found: (M+Na)$^+$=654.2.

Example 74

2-(Ethylamino)-N-[2-[[(cis)-2-[[4-(aminosulfonyl)benzoyl]amino]cyclohexyl]amino]-2-oxoethyl]-5-trifluoromethyl benzamide (74a) 2-(Ethylamino)-5-trifluoromethyl benzoic acid (51 mg) was incorporated into Example 61, step (61c), to give the title benzamide (45 mg). MS found: (M+Na)$^+$=592.1.

Example 75

2-(Methylamino)-N-[2-[[(cis)-2-[[4-(aminosulfonyl)benzoyl]amino]cyclohexyl]amino]-2-oxoethyl]-5-trifluoromethyl benzamide (75a) 2-(Methylamino)-5-trifluoromethyl benzoic acid (25 mg) was incorporated into Example 61, step (61c), to give the title benzamide (8 mg). MS found: (M+Na)$^+$=578.2.

Example 76

2-Amino-N-[2-[[(cis)-2-[[4-(aminosulfonyl)benzoyl]amino]cyclohexyl]amino]-2-oxoethyl]-5-bromo benzamide (76a) 2-Amino-5-bromo benzoic acid (79 mg) was incorporated into Example 61, step (61c), to give the title benzamide (69 mg). MS found: (M+H)$^+$=554.1.

Example 77

Tert-butyl 2-[({2-[((cis)-2-{[4-(aminosulfonyl)benzoyl]amino}cyclohexyl)amino]-2-oxoethyl}amino)carbonyl]-4-(trifluoromethoxy)phenylcarbamate (77a) 2-(Tert-butoxycarbonyl)amino-5-trifluoromethoxybenzoic acid (42 mg) was incorporated into Example 61, step (61c), to give the title phenylcarbamate (45 mg). MS found: (M+Na)$^+$=680.2.

Example 78

2-Amino-N-[2-[[(cis)-2-[[4-(aminosulfonyl)benzoyl]amino]cyclohexyl]amino]-2-oxoethyl]-5-trifluoromethoxy benzamide (78a) The material from above, (77a), (25 mg) was dissolved in CH$_2$Cl$_2$ (3 mL) prior to the addition of TFA (1.5 mL). After 1 h, the solution was concentrated. Reverse phase HPLC purification (gradient elution, water/acetonitrile/TFA) of the resulting residue provided the title benzamide (20 mg). MS found: (M+Na)$^+$=580.1.

Example 79

2-(Allylamino)-N-[2-[[(cis)-2-[[4-(aminosulfonyl)benzoyl]amino]cyclohexyl]amino]-2-oxoethyl]-5-trifluoromethyl benzamide (79a) 2-(allylamino)-5-trifluoromethyl benzoic acid (50 mg) was incorporated into Example 61, step (61c), to give the title benzamide (62 mg). MS found: (M+Na)$^+$=604.1.

Example 80

2-((2-methyl-2-propenyl)amino)-N-[2-[[(cis)-2-[[4-(aminosulfonyl)benzoyl]amino]cyclohexyl]amino]-2-oxoethyl]-5-trifluoromethyl benzamide (80a) 2-((2-methyl-2-propenyl)amino)-5-trifluoromethyl benzoic acid (52 mg) was incorporated into Example 61, step (61c), to give the title benzamide (40 mg). MS found: (M+Na)$^+$=618.1.

Example 81

2-(cyclopropylmethylene)amino-N-[2-[[(cis)-2-[[4-(aminosulfonyl)benzoyl]amino]cyclohexyl]amino]-2-oxoethyl]-5-trifluoromethyl benzamide (81a) 2-(cyclopropylmethylene)amino-5-trifluoromethyl benzoic acid (52 mg) was incorporated into Example 61, step (61c), to give the title benzamide (20 mg). MS found: $(M+Na)^+=618.2$.

Example 82

2-(butyl)amino-N-[2-[[(cis)-2-[[4-(aminosulfonyl)benzoyl]amino]cyclohexyl]amino]-2-oxoethyl]-5-trifluoromethyl benzamide (82a) 2-(butyl)amino-5-trifluoromethyl benzoic acid (53 mg) was incorporated into Example 61, step (61c), to give the title benzamide (20 mg). MS found: $(M+Na)^+=620.1$.

Example 83

2-(propyl)amino-N-[2-[[(cis)-2-[[4-(aminosulfonyl)benzoyl]amino]cyclohexyl]amino]-2-oxoethyl]-5-trifluoromethyl benzamide (83a) 2-(propyl)amino-5-trifluoromethyl benzoic acid (50 mg) was incorporated into Example 61, step (61c), to give the title benzamide (59 mg). MS found: $(M+Na)^+=606.2$.

Example 84

2-((2-methyl-2-propyl)amino)-N-[2-[[(cis)-2-[[4-(aminosulfonyl)benzoyl]amino]cyclohexyl]amino]-2-oxoethyl]-5-trifluoromethyl benzamide (84a) 2-((2-methyl-2-propyl)amino)-5-trifluoromethyl benzoic acid (50 mg) was incorporated into Example 61, step (61c), to give the title benzamide (50 mg). MS found: $(M+Na)^+=620.2$.

Example 85

2-((aminocarbonyl)amino)-N-[2-[[(cis)-2-[[4-(aminosulfonyl)benzoyl]amino]cyclohexyl]amino]-2-oxoethyl]-5-trifluoromethyl benzamide (85a) 2-(aminocarbonyl)amino-5-trifluoromethyl benzoic acid (60 mg) was incorporated into Example 61, step (61c), to give the title benzamide (7 mg). MS found: $(M+Na)^+=665.1$.

Example 86

2-(acetylamino)-N-[2-[[(cis)-2-[[4-(aminosulfonyl)benzoyl]amino]cyclohexyl]amino]-2-oxoethyl]-5-trifluoromethyl benzamide (86a) 2-acetylamino-5-trifluoromethyl benzoic acid (77 mg) was incorporated into Example 61, step (61c), to give the title benzamide (35 mg). MS found: $(M+H)^+=642.1$.

Example 87

2-(Methylamino)-N-[2-[[(cis)-2-[[4-(aminosulfonyl)benzoyl]amino]cyclohexyl]amino]-2-oxoethyl]-5-iodomethyl benzamide (87a) 2-Methylamino-5-iodo benzoic acid (127 mg) was incorporated into Example 61, step (61c), to give the title benzamide (20 mg). MS found: $(M+H)^+=614.1$.

Example 88

2-(Ethylamino)-N-[2-[[(cis)-2-[[4-(aminosulfonyl)benzoyl]amino]cyclohexyl]amino]-2-oxoethyl]-5-iodomethyl benzamide (88a) 2-Ethylamino-5-iodo benzoic acid (100 mg) was incorporated into Example 61, step (61c), to give the title benzamide (25 mg). MS found: $(M+H)^+=628.1$.

Example 89

2-(Trifluoroacetylamino)-N-[2-[[(cis)-2-[[4-(aminosulfonyl)benzoyl]amino]cyclohexyl]amino]-2-oxoethyl]-5-iodomethyl benzamide (89a) 2-Trifluoroacetylamino-5-iodo benzoic acid (77 mg) was incorporated into Example 61, step (61c), to give the title benzamide (44 mg). MS found: $(M+H)^+=696.1$.

Example 90

2-(amino)-N-[2-[[(cis)-2-[[4-(aminosulfonyl)benzoyl]amino]cyclohexyl]amino]-2-oxoethyl]-5-nitro benzamide (90a) 2-amino-5-nitro benzoic acid (28 mg) was incorporated into Example 61, step (61c), to give the title benzamide (15 mg). MS found: $(M+H)^+=519.1$.

Example 91

Iso-propyl 2-[({2-[((cis)-2-{[4-(aminosulfonyl)benzoyl]amino}cyclohexyl)amino]-2-oxoethyl}amino)carbonyl]-4-(iodo)phenylcarbamate (91a) 2-(Iso-propoxycarbonyl)amino-5-iodobenzoic acid (73 mg) was incorporated into Example 61, step (61c), to give the title benzamide (10 mg). MS found: $(M+Na)^+=686.2$.

Example 92

Tert butyl 2-[({2-[((cis)-2-{[4-(aminosulfonyl)benzoyl]amino}cyclohexyl)amino]-2-oxoethyl}amino)carbonyl]-4-(iodo)phenylcarbamate (92a) 2-(Tert-butoxycarbonyl)amino-5-iodobenzoic acid (76 mg) was incorporated into Example 61, step (61c), to give the title benzamide (9 mg). MS found: $(M+Na)^+=722.1$.

Example 93

2-(amino)-N-[2-[[(cis)-2-[[4-(aminosulfonyl)benzoyl]amino]cyclohexyl]amino]-2-oxoethyl]-3,5-dinitro benzamide (93a) 2-amino-3,5-dinitro benzoic acid (45.4 mg) was incorporated into Example 61, step (61c), to give the title benzamide (20 mg). MS found: $(M+H)^+=632.0$.

Example 94

2-((Isopropylaminocarbonyl)amino)-N-[2-[[(cis)-2-[[4-(aminosulfonyl)benzoyl]amino]cyclohexyl]amino]-2-oxoethyl]-5-trifluoromethyl benzamide (94a) The material from above, (66a), (20 mg) was dissolved in DMF (5 mL) prior to the addition of N-methylmorpholine (6 mg) and isopropyl isocyanate (4 mg). After 5 h, the solution was loaded onto an HPLC. Reverse phase HPLC purification (gradient elution, water/acetonitrile/TFA) provided the title benzamide (5 mg). MS found: $(M+Na)^+=649.2$.

Example 95

2-((cyclohexylcarbonyl)amino)-N-[2-[[(cis)-2-[[4-(aminosulfonyl)benzoyl]amino]cyclohexyl]amino]-2-oxoethyl]-5-trifluoromethyl benzamide (95a) The material from above, (66a), (20 mg) was dissolved in THF (2 mL) prior to the addition of 2M $K_2CO_3$ (0.1 mL) and cyclohexane carbonyl chloride(0.1 mL). After 15 h, 1 N HCl was added and this was extracted with ethyl acetate. The ethyl acetate was dried and concentrated. Reverse phase HPLC purification (gradient elution, water/acetonitrile/TFA) provided the title benzamide (15 mg). MS found: $(M+H)^+=652.2$.

Example 96

2-((Cyclopentylmethylenecarbonyl)amino)-N-[2-[[(cis)-2-[[4-(aminosulfonyl)benzoyl]amino]cyclohexyl]amino]-2-oxoethyl]-5-trifluoromethyl benzamide (96a) Cyclopentylacetyl chloride (0.1 mL) was incorporated into Example 95, step (95a), to give the title benzamide (10 mg). MS found: $(M+H)^+=652.2$.

Example 97

2-((cyclohexylcarbonyl)amino)-N-[2-[[(cis)-2-[[4-(methylsulfonyl)benzoyl]amino]cyclohexyl]amino]-2-oxoethyl]-5-trifluoromethyl benzamide (97a) 1-(N-tert-Butyloxycarbonyl)-cis-cyclohexane-1,2-diamine (prepared in an analogous fashion to N-tert-butyloxycarbonyl-cyclohexane-(S,S)-1,2-diamine, see: C. Wu et al., *Bioorg. Med. Chem.* 1997, 5, 1925) (8 g) was dissolved in THF (125 mL) and water (18 mL). After cooling to 0° C., triethyl amine (6.2 mL) was added followed by $Cbz_2O$ (12.8 g). This was warmed to rt and was stirred for 18 h. Some of the THF was removed before ethyl acetate was added. This solution was washed with brine and then 1 N HCl solution (aq). The EtOAc was dried ($MgSO_4$), filtered, and concentrated. The resulting residue was dissolved in $CH_2Cl_2$ (15 mL). After cooling to 0° C., TFA (15 mL) was added dropwise. After 1 h, the reaction was concentrated and 1 N HCl was added. This acidic solution was extracted with $Et_2O$. The aqueous solution was taken to pH=13 via addition of solid $Na_2CO_3$. This solution was extracted with EtOAc. The EtOAc was dried ($MgSO_4$), filtered, and concentrated to give 1-(N-benzyloxycarbonyl)-cis-cyclohexane-1,2-diamine (7.9 g). MS found: $(M+H)^+=249.1$.

(97b) The material from above 1-(N-benzyloxycarbonyl)-cis-cyclohexane-1,2-diamine (5 g) was dissolved in DMF (100 mL). After cooling to 0° C., 4-methylmorpholine (11 mL) and N-Boc-Gly-OH (4.2 g) were added. BOP Reagent (11.6 g) was added, and the mixture was stirred at rt for 18 h. The DMF was removed. EtOAc was added along with 1 N HCl solution. The EtOAc layer was washed with 1 N HCl, $NaHCO_3$ solution, and brine. The EtOAc was dried ($MgSO_4$), filtered, and concentrated to give cis-[2[[[[(1,1-dimethylethoxy)carbonyl]amino]acetyl]amino]cyclohexyl]-carbamic acid benzyl ester (9.6 g). MS found: $(M+H)^+=406.3$.

(97c) The material from above (9.6 g) was dissolved in $CH_2Cl_2$ (20 mL). After cooling to 0° C., TFA (10 mL) was added dropwise. After 1 h, the reaction was concentrated. A portion of this residue (5.5 g) was dissolved in DMF (65 mL). After cooling to 0° C., 4-methylmorpholine (7.2 mL) and 2-(tert-butoxycarbonyl)amino-5-trifluoromethylbenzoic acid (4.0 g) were added. BOP Reagent (8.7 g) was added, and the mixture was stirred at rt for 18 h. The DMF was removed. EtOAc was added along with 1 N HCl solution. The EtOAc layer was washed with 1 N HCl, $NaHCO_3$ solution, and brine. The EtOAc was dried ($MgSO_4$), filtered, and concentrated. Flash chromatography of the resulting residue gave [(cis)-2-[[[[(2-(tert-butyloxycarbonylamino)-5-trifluoromethyl)benzoyl]amino]acetyl]amino]cyclohexyl]carbamic acid benzyl ester (5.9 g). MS found: $(M+H)^+=593.3$.

(97d) The material (97c) from above (2 g) was dissolved in $CH_2Cl_2$ (5 mL). After cooling to 0° C., TFA (2.5 mL) was added dropwise. After 1 h, the reaction was concentrated. A portion of the resulting residue (500 mg) was dissolved in THF (3 mL) prior to the addition of 4-methylmorpholine (0.56 mL). After 5 min, cyclohexanecarbonyl chloride (0.4 mL) was added dropwise. After 30 min, EtOAc and 1 N HCl (aq) were added. The EtOAc was dried ($MgSO_4$), filtered, and concentrated. This material was dissolved in MeOH (5 mL) prior to the addition of 10% Pd/C (200 mg). A hydrogen balloon was added and the reaction continued to stir. After 1.5 h, the solution was filtered and concentrated to give N-[2-[[(cis)-2-aminocyclohexyl]amino]-2-oxoethyl]-3-(2-cyclohexylcarbonylamino-5-trifluoromethyl)benzamide (202 mg). MS found: $(M+H)^+=469.4$.

(97e) The material (97d) from above (50 mg) was dissolved in DMF (2 mL). After cooling to 0° C., 4-methylmorpholine (55.5 mg) and p-(methylsulfonyl)benzoic acid (26 mg) were added. After 5 min, BOP Reagent (73 mg) was added and the mixture was stirred at rt for 18 h. The DMF was removed. EtOAc was added along with 1 N HCl solution. The EtOAc layer was washed with 1 N HCl, $NaHCO_3$ solution, and brine. The EtOAc was dried ($MgSO_4$), filtered, and concentrated. Reverse phase HPLC purification (gradient elution, water/acetonitrile/TFA) provided the title benzamide (15 mg). MS found: $(M+H)^+=651.2$.

Example 98

2-((cyclohexylcarbonyl)amino)-N-[2-[[(cis)-2-[[4-(methylthio)benzoyl]amino]cyclohexyl]amino]-2-oxoethyl]-5-trifluoromethyl benzamide (98a) 4-(Methylthio)benzoic (28 mg) was incorporated into Example 97, step (97e), to give the title benzamide (20 mg). MS found: $(M+H)^+=619.3$.

Example 99

2-((Isopropylaminocarbonyl)amino)-N-[2-[[(cis)-2-[[4-(methylthio)benzoyl]amino]cyclohexyl]amino]-2-oxoethyl]-5-trifluoromethyl benzamide (99a) Isopropyl isocyanate (0.3 mL) was incorporated into Example 97, step (97d), and reacted for 18 h before being taken forward. Subsequently, 4-(methylthio)benzoic (22 mg) was incorporated into Example 97, step (97e), to give the title benzamide (20 mg). MS found: $(M+H)^+=594.3$.

Example 100

2-((Isopropylaminocarbonyl)amino)-N-[2-[[(cis)-2-[[4-(methylsulfonyl)benzoyl]amino]cyclohexyl]amino]-2-oxoethyl]-5-trifluoromethyl benzamide (100a) Isopropyl isocyanate (0.3 mL) was incorporated into Example 97, step (97d), and reacted for 18 h before being taken forward. Subsequently, 4-(methylsulfonyl)benzoic (26 mg) was incorporated into Example 97, step (97e), to give the title benzamide (9 mg). MS found: $(M+H)^+=541.2$.

Example 101

2-((Methylsulfonyl)amino)-N-[2-[[(cis)-2-[[4-(aminosulfonyl)benzoyl]amino]cyclohexyl]amino]-2-oxoethyl]-5-trifluoromethyl benzamide (101a) Methanesulfonyl chloride (0.3 mL) and pyridine (35 mg) were incorporated into Example 97, step (97d), and reacted for 18 h before being taken forward. Subsequently, p-sulfamylbenzoic (43 mg) was incorporated into Example 97, step (97e), to give the title benzamide (30 mg). MS found: $(M+H)^+=620.1$.

Example 102

2-((Aminocarbonyl)amino)-N-[2-[[(cis)-2-[[4-(aminosulfonyl)benzoyl]amino]cyclohexyl]amino]-2-oxoethyl]-5-trifluoromethyl benzamide (102a) Sodium cyanate (0.3 mL) in acetic acid and water were incorporated into Example 97, step (97d), and reacted for 1 h before the precipitated solid was taken forward. Subsequently, p-sulfamylbenzoic (24 mg) was incorporated into Example 97, step (97e), to give the title benzamide (20 mg). MS found: $(M+H)^+=585.2$.

Example 103

2-Allylamino-5-trifluoromethylbenzoic acid (103a) 2-(Tert-butoxycarbonyl)amino-5-trifluoromethylbenzoic acid (3.0 g) was dissolved in DMF prior to the addition of $K_2CO_3$ (2.4 g) and iodomethane (0.8 mL). After 1.5 h, the solution was diluted with EtOAc and was washed with brine solution followed by 1N HCl solution. The organic layer was then washed with $Na_2CO_3$ solution, water, and brine. The organic layer was dried ($MgSO_4$), filtered, and concentrated to give the ester as a off-white solid (3.03 g). A portion of this solid was dissolved in TFA (3.3 mL) and cooled to 0° C. prior to the addition of TFAA (0.97 mL). After 10 min, crushed ice was added. After an additional 30 min, the solid was collected and washed with water. The solid was dried to give the TFA amide (970 mg). A portion of this solid (385 mg) was dissolved in DMF (2 mL) and $K_2CO_3$ (338 mg) was added followed by allyl bromide (1.21 mL). The reaction was stirred 18 h before it was diluted with EtOAc and washed with 1N HCl and brine. The EtOAc was dried, filtered, and concentrated. The resulting residue was dissolve in THF (10 mL) prior to addition of 1N LiOH (10 mL) and 20 drops of MeOH. After 18 h, the THF was removed and the solution was made acidic (pH=5) with 1N HCl. This solution was extracted with EtOAc. The organic layer was washed with brine, dried, filtered, and concentrated to give 2-allylamino-5-trifluoromethylbenzoic acid (265 mg). MS found: $(M+H)^+=246.2$.

Example 104

2-((Allyl)amino)-N-[2-[[(cis)-2-[[4-(methylsulfonyl)benzoyl]amino]cyclohexyl]amino]-2-oxoethyl]-5-trifluoromethyl benzamide (104a) 1-(N-tert-Butyloxycarbonyl)-cis-cyclohexane-1,2-diamine (prepared in an analogous fashion to N-tert-butyloxycarbonyl-cyclohexane-(S,S)-1,2-diamine, see: C. Wu et al., *Bioorg. Med. Chem.* 1997, 5, 1925) (6 g) was dissolved in DMF (80 mL). After cooling to 0° C., 4-methylmorpholine (15.4 mL) and N-Cbz-Gly-OH (7.03 g) were added. BOP Reagent (18.6 g) was added, and the mixture was stirred at rt for 18 h. EtOAc was added along with 1 N HCl solution. The EtOAc layer was washed with 1 N HCl, $NaHCO_3$ solution, and brine. The EtOAc was dried ($MgSO_4$), filtered, and concentrated. Flash chromatography of the resulting residue gave cis-[2[[[[(benzyloxy)carbonyl]amino]acetyl]amino]cyclohexyl]-carbamic acid tert-butyl ester (6.2 g). MS found: $(M+H)^+406.3$.

(104b) The material from above (9.6 g) was dissolved in MeOH (60 mL) prior to the addition of 10% Pd/C (1.5 g). A hydrogen balloon was added and the solution was stirred for 18 h. The palladium was filtered off and the filtrate was concentrated. A portion (301 mg) of the resulting residue was dissolved in DMF (5 mL). After cooling to 0° C., 4-methylmorpholine (0.5 mL) and 2-allylamino-5-trifluoromethylbenzoic acid (Example 103) (226 mg) were added. BOP Reagent (613 mg) was added, and the mixture was stirred at rt for 18 h. EtOAc was added along with 1 N HCl solution. The EtOAc layer was washed with 1 N HCl, $NaHCO_3$ solution, and brine. The EtOAc was dried ($MgSO_4$), filtered, and concentrated. Flash chromatography of the resulting gave [(cis)-2-[[[[(2-(allylamino)-5-trifluoromethyl)benzoyl]amino]acetyl]amino]cyclohexyl]carbamic acid tert-butyl ester (364 mg). MS found: $(M+Na)^+521.2$.

(104c) The material (104b) from above (360 mg) was dissolved in 4M HCl/dioxane(10 mL). After stirring for 2 h, the solution was concentrated. A portion (50 mg) of the resulting residue was dissolved in DMF (2.5 mL). After cooling to 0° C., 4-methylmorpholine (58 mg) and 4-methylsulfonylbenzoic acid (28 mg) was added. BOP Reagent (76 mg) was added, and the mixture was stirred at rt for 18 h. EtOAc was added along with 1 N HCl solution. The EtOAc layer was washed with 1 N HCl, $NaHCO_3$ solution, and brine. The EtOAc was dried ($MgSO_4$), filtered, and concentrated. Reverse phase HPLC purification (gradient elution, water/acetonitrile/TFA) provided the title benzamide (15 mg). MS found: $(M+H)^+=581.3$.

Example 105

2-((Allyl)amino)-N-[2-[[(cis)-2-[[4-(methylthio)benzoyl]amino]cyclohexyl]amino]-2-oxoethyl]-5-trifluoromethyl benzamide (105a) 4-(Methylthio)benzoic (168 mg) was incorporated into Example 104, step (104c), to give the title benzamide (20 mg). MS found: (M+H)$^+$=549.3.

Example 106

2-((2-Methyl-2-propenyl)amino)-N-[2-[[(cis)-2-[[4-(methylsulfonyl)benzoyl]amino]cyclohexyl]amino]-2-oxoethyl]-5-trifluoromethyl benzamide (106a) 3-Bromo-2-methylpropene was substituted for allyl bromide in Example 103 to give 2-(2-methyl-2-propenyl)amino-5-trifluoromethylbenzoic acid, which was incorporated into Example 104, step (104b), to give the title benzamide (20 mg). MS found: (M+H)$^+$=595.2

Example 107

2-((2-methyl-2-propenyl)amino)-N-[2-[[(cis)-2-[[4-(methylthio)benzoyl]amino]cyclohexyl]amino]-2-oxoethyl]-5-trifluoromethyl benzamide (107a) 3-Bromo-2-methylpropene was substituted for allyl bromide in Example 103 to give 2-(2-methyl-2-propenyl)amino-5-trifluoromethylbenzoic acid, which was incorporated into Example 104, step (104b). Subsequently, 4-(methylthio)benzoic (168 mg) was incorporated into Example 104, step (104c), to give the title benzamide (20 mg). MS found: (M+H)$^+$=563.3.

Example 108

2-((Propyl)amino)-N-[2-[[(cis)-2-[[4-(methylsulfonyl)benzoyl]amino]cyclohexyl]amino]-2-oxoethyl]-5-trifluoromethyl benzamide (108a) For this preparation, Example 104, step 104c, was altered as follows. [(Cis)-2-[[[[(2-(allylamino)-5-trifluoromethyl)-benzoyl]amino]acetyl]amino]cyclohexyl]carbamic acid tert-butyl ester from 104(b) (360 mg) was dissolved in 4M HCl/dioxane(10 mL). After stirring for 2 h, the solution was concentrated. A portion (300 mg) of the resulting residue was dissolved in MeOH (5 mL) and 10% Pd/C was added. A hydrogen balloon was added and the solution was stirred for 2 h. The palladium was filtered and the solution was concentrated. A portion (50 mg) of the resulting residue was dissolved in DMF (2.5 mL). After cooling to 0° C., 4-methylmorpholine (63 mg) and 4-methylsulfonylbenzoic acid (30 mg) were added. BOP Reagent (83 mg) was added, and the mixture was stirred at rt for 18 h. EtOAc was added along with 1 N HCl solution. The EtOAc layer was washed with 1 N HCl, NaHCO$_3$ solution, and brine. The EtOAc was dried (MgSO$_4$), filtered, and concentrated. Reverse phase HPLC purification (gradient elution, water/acetonitrile/TFA) provided the title benzamide (15 mg). MS found: (M+H)$^+$=583.3.

Example 109

2-((Propyl)amino)-N-[2-[[(cis)-2-[[4-(methylthio)benzoyl]amino]cyclohexyl]amino]-2-oxoethyl]-5-trifluoromethyl benzamide (109a) 4-(Methylthio)benzoic (25 mg) was incorporated into Example 108 to give the title benzamide (10 mg). MS found: (M+H)$^+$=551.3.

Example 110

2-((2-Methylpropyl)amino)-N-[2-[[(cis)-2-[[4-(methylsulfonyl)benzoyl]amino]cyclohexyl]amino]-2-oxoethyl]-5-trifluoromethyl benzamide (110a) [(Cis)-2-[[[[(2-((2-methyl-2-propenyl)amino)-5-trifluoromethyl)benzoyl]amino]acetyl]amino]cyclohexyl]carbamic acid tert-butyl ester was incorporated into Example 108 to give the title benzamide (15 mg). MS found: (M+H)$^+$=597.3.

Example 111

2-((2-Methylpropyl)amino)-N-[2-[[(cis)-2-[[4-(methylthio)benzoyl]amino]cyclohexyl]amino]-2-oxoethyl]-5-trifluoromethyl benzamide (111a) 4-(Methylthio)benzoic (25 mg) was incorporated into Example 110 to give the title benzamide (10 mg). MS found: (M+H)$^+$=565.3.

Example 112

2-((Butyl)amino)-N-[2-[[(cis)-2-[[4-(methylsulfonyl)benzoyl]amino]cyclohexyl]amino]-2-oxoethyl]-5-trifluoromethyl benzamide (112a) 2-Butylamino-5-trifluoromethylbenzoic acid (prepared analogously to Example 103 with butyl iodide) was incorporated into Example 104, step (104b), to give the title benzamide (25 mg). MS found: (M+H)$^+$=597.2.

Example 113

2-((Butyl)amino)-N-[2-[[(cis)-2-[[4-(methylthio)benzoyl]amino]cyclohexyl]amino]-2-oxoethyl]-5-trifluoromethyl benzamide (113a) 4-(Methylthio)benzoic (22 mg) was incorporated into Example 112 to give the title benzamide (25 mg). MS found: (M+H)$^+$=565.3.

Example 114

2-((Ethylaminocarbonyl)amino)-N-[2-[[(cis)-2-[[4-(methylthio)benzoyl]amino]cyclohexyl]amino]-2-oxoethyl]-5-trifluoromethyl benzamide (114a) [(Cis)-2-[[[[(2-(tert-butyloxycarbonylamino)-5-trifluoromethyl)benzoyl]amino]acetyl]amino]cyclohexyl]carbamic acid benzyl ester (Example 97c) (1.4 g) was dissolved in 4M HCl/dioxane. After stirring at rt for 3h, the reaction was concentrated. A portion of this residue (500 mg) was dissolved in MeOH (5 mL) prior to the addition of 10% Pd/C. A hydrogen balloon was added and the solution was stirred for 3 h. The palladium was filtered and the solution was concentrated. The resulting residue was cooled to 0° C. prior to the addition of 4-methylmorpholine (0.55 mL) and 4-(methylthio)benzoic acid (168 mg). BOP Reagent (531 mg) was added, and the mixture was stirred at rt for 18 h. The DMF was removed. EtOAc was added along with 1 N HCl solution. The EtOAc layer was washed with 1 N HCl, NaHCO$_3$ solution, and brine. The EtOAc was dried (MgSO$_4$), filtered, and concentrated. Flash chromatography of the resulting residue gave 2-(amino)-N-[2-[[(cis)-2-[[4-(methylthio)benzoyl]amino] cyclohexyl]amino]-2-oxoethyl]-5-trifluoromethyl benzamide (360 mg). MS found: (M+H)$^+$=509.2.

(114b) 2-(amino)-N-[2-[[(cis)-2-[[4-(methylthio)benzoyl]amino]cyclohexyl]amino]-2-oxoethyl]-5-trifluoromethyl benzamide (Example 114a) (50 mg) was dissolved in THF (2.5 mL) prior to the addition of triethylamine (30 mg) and ethyl isocyanate (21 mg). After stirring for 72 h, EtOAc was added along with 1 N HCl solution. The EtOAc layer was washed with 1 N HCl and brine. The EtOAc was dried (MgSO$_4$), filtered, and concentrated. Reverse phase HPLC purification (gradient elution, water/acetonitrile/TFA) provided the title benzamide (10 mg). MS found: (M+Na)$^+$=602.4.

Example 115

2-((Allylaminocarbonyl)amino)-N-[2-[[(cis)-2-[[4-(methylthio)benzoyl]amino]cyclohexyl]amino]-2-oxoethyl]-5-trifluoromethyl benzamide (115a) Allyl isocyanate (25 mg) was incorporated into Example 114, step (114b), to give the title benzamide (10 mg). MS found: (M+H)$^+$=592.3.

Example 116

2-((2-methylpropyl)aminocarbonyl)amino-5-trifluoromethylbenzoic acid (116a) 2-Amino-5-trifluoromethylbenzoic acid (3.75 g) was dissolved in DMF (20 mL) prior to the addition of K$_2$CO$_3$ (3.78 g) and allyl bromide (2.4 mL). After 3 h, the solution was diluted with EtOAc and was washed with brine solution and water. The organic layer was dried (MgSO$_4$), filtered, and concentrated. Flash chromatography of the resulting residue gave the allyl ester as a yellow oil (2.6 g). This ester was dissolved in THF (6 mL) and added dropwise to a THF (3.5 mL) solution of trichloromethyl chloroformate (1.1 mL). After stirring for 18 h, the solution was concentrated. A portion (1.4 g) of the resulting residue was dissolved in THF (2.2 mL) prior to the addition of iso-butylamine (0.95 mL) in THF (3 mL). After 4 h, the solution was diluted with EtOAc and was washed with brine solution and 1N HCl. The organic layer was dried (MgSO$_4$), filtered, and concentrated to a white solid. This solid was dissolved in CH$_3$CN (30 mL) prior to the addition of pyrrolidine (0.23 mL) and Pd(PPh)$_4$ (64 mg). After 3 h, the solution was diluted with EtOAc and was washed 1N HCl. The organic layer was dried (MgSO$_4$), filtered, and concentrated to 2-((2-methylpropyl)aminocarbonyl)amino-5-trifluoromethylbenzoic acid (386 mg) as a white solid. MS found: (2M−H)$^-$=607.3.

Example 117

2-((Iso-butylaminocarbonyl)amino)-N-[2-[[(cis)-2-[[4-(methylthio)benzoyl]amino]cyclohexyl]amino]-2-oxoethyl]-5-trifluoromethyl benzamide (117a) 1-(N-tert-Butyloxycarbonyl)-cis-cyclohexane-1,2-diamine (6 g) was dissolved in DMF (100 mL). After cooling to 0° C, 4-methylmorpholine (15.4 mL) and p-(methylthio) benzoic acid (5.2 g) were added. BOP Reagent (15.0 g) was added, and the mixture was stirred at rt for 18 h. The DMF was removed. EtOAc was added along with 1 N HCl solution. The EtOAc layer was washed with 1 N HCl, NaHCO$_3$ solution, and brine. The EtOAc was dried (MgSO$_4$), filtered, and concentrated. Flash chromatography of the resulting residue gave tert-butyl (cis)-2-{[4-(methylthio)benzoyl]amino} cyclohexylcarbamate (8.4 g). MS found: (2M+Na)$^+$=751.3.

(117b) The material, 117a, from above (8.4 g) was dissolved in 4M HCl/dioxane. After 3 h, the solution was concentrated. The resulting residue was dissolved in DMF (50 mL). After cooling to 0° C., 4-methylmorpholine (12.6 mL) and N-Boc-glycine (4.8 g) were added. BOP Reagent (15.3 g) was added, and the mixture was stirred at rt for 18 h. The DMF was removed. EtOAc was added along with 1 N HCl solution. The EtOAc layer was washed with 1 N HCl, NaHCO$_3$ solution, and brine. The EtOAc was dried (MgSO$_4$), filtered, and concentrated. Flash chromatography of the resulting residue gave tert-butyl 2-[((cis)-2-{[4-(methylthio)benzoyl] amino}cyclohexyl)amino]-2-oxoethyl carbamate (9.4 g). MS found: (M+Na)$^+$=444.4.

(117c) A portion (2.3 g) of the material, (117b), from above was dissolved in 4M HCl/dioxane. After 3 h, the solution was concentrated. A portion of the resulting material (100 mg) was dissolved in DMF (5 mL). After cooling to 0° C., 4-methylmorpholine (0.15 mL) was added followed by 2-((2-methylpropyl)aminocarbonyl)amino-5-trifluoromethylbenzoic acid (Example 116) (26 mg). After 5 min, BOP Reagent (161 mg) was added and the mixture was stirred at rt for 18 h. The DMF was removed. EtOAc was added along with 1 N HCl solution. The EtOAc layer was washed with 1 N HCl, NaHCO$_3$ solution, and brine. The EtOAc was dried (MgSO$_4$), filtered, and concentrated. Reverse phase HPLC purification (gradient elution, water/acetonitrile/TFA) provided the title benzamide (50 mg). MS found: (M+H)$^+$=608.3.

Example 118

2-((Cyclopentylaminocarbonyl)amino)-N-[2-[[(cis)-2-[[4-(methylthio)benzoyl]amino]cyclohexyl] amino]-2-oxoethyl]-5-trifluoromethyl benzamide (118a) 2-(cyclopentylaminocarbonyl)amino-5-trifluoromethylbenzoic acid (made analogously to Example 116 with cyclopentylamine in place of iso-butylamine) (88.6 mg) was incorporated into Example 117, step (117c), to give the title benzamide (50 mg). MS found: (M+H)$^+$=620.3.

Example 119

2-((Tert-butoxycarbonyl)amino)-N-[2-[[(cis)-2-[[4-(methylthio)benzoyl]amino]cyclohexyl]amino]-2-oxoethyl]-5-trifluoromethyl benzamide (119a) 2-(Tert-butoxycarbonyl)amino-5-trifluoromethylbenzoic acid (Takagishi et al., Synlett 1992, 360) (88.6 mg) was incorporated into Example 117, step (117c), to give the title benzamide (25 mg). MS found: (M+H)$^+$=609.3.

Example 120

2-((Iso-propoxycarbonyl)amino)-N-[2-[[(cis)-2-[[4-(methylthio)benzoyl]amino]cyclohexyl]amino]-2-oxoethyl]-5-trifluoromethyl benzamide (120a) 2-(Iso-propoxycarbonyl)amino-5-trifluoromethyl-benzoic acid (98 mg) was incorporated into Example 117, step (117c), to give the title benzamide (20 mg). MS found: $(M+H)^+$=595.3.

Example 121

2-((Ethoxycarbonyl)amino)-N-[2-[[(cis)-2-[[4-(methylthio)benzoyl]amino]cyclohexyl]amino]-2-oxoethyl]-5-trifluoromethyl benzamide (121a) 2-(Ethoxycarbonyl)amino-5-trifluoromethyl-benzoic acid (96 mg) was incorporated into Example 117, step (117c), to give the title benzamide (30 mg). MS found: $(M+H)^+$=581.3.

Example 122

N-[2-[(1-Pyrrolidinylcarbonyl)amino]-5-(trifluoromethyl)benzoyl]glycine (122a) 2-(Pyrrolidinylcarbonyl)amino-5-trifluoromethyl-benzoic acid (made analogously to Example 116 with pyrrolidine in place of iso-butylamine (2.9 g) was dissolved in DMF (40 mL). After cooling to 0° C., 4-methylmorpholine (3.2 mL) and glycine benzyl ester hydrogen chloride (5.6 g) were added. After 5 min, BOP Reagent (5.6 g) was added and the mixture was stirred at rt for 18 h. EtOAc was added along with 1 N HCl solution. The EtOAc layer was washed with 1 N HCl, NaHCO$_3$ solution, and brine. The EtOAc was dried (MgSO$_4$), filtered, and concentrated to a solid (2.6 g). This solid was dissolved in MeOH (14 mL) prior to the addition of 10% Pd/C. A hydrogen balloon was added and the solution was stirred for 1 h. The palladium was filtered and the solution was concentrated to give the title glycine derivative (2.0 g) as a white solid. MS found: $(M+H)^+$=360.2.

Example 123

2-((Pyrrolidinylcarbonyl)amino)-N-[2-[[(cis)-2-[[4-(methylthio)benzoyl]amino]cyclohexyl]amino]-2-oxoethyl]-5-trifluoromethyl benzamide (123a) Tert-butyl (cis)-2-{[4-(methylthio)benzoyl]amino}cyclohexylcarbamate (117a) was dissolved in CH$_2$Cl$_2$ (5 mL) and cooled to 0° C. TFA (5 mL) was added and the solution was stirred. After 1 h, the solution was concentrated. A portion of the resulting residue (80 mg) was dissolved in DMF (2 mL). After cooling to 0° C., 4-methylmorpholine (0.1 mL) and N-[2-[(1-pyrrolidinylcarbonyl)amino]-5-(trifluoromethyl)benzoyl]glycine (Example 122)(75 mg) were added. After 5 min, BOP Reagent (116 mg) was added and the mixture was stirred at rt for 18 h. EtOAc was added along with 1 N HCl solution. The EtOAc layer was washed with 1 N HCl, NaHCO$_3$ solution, and brine. The EtOAc was dried (MgSO$_4$), filtered, and concentrated. Reverse phase HPLC purification (gradient elution, water/acetonitrile/TFA) provided the title benzamide (30 mg). MS found: $(M+H)^+$=606.5.

Example 124

2-((Morpholinylcarbonyl)amino)-N-[2-[[(cis)-2-[[4-(methylthio)benzoyl]amino]cyclohexyl]amino]-2-oxoethyl]-5-trifluoromethyl benzamide (124a) N-[2-[(l-Morpholinylcarbonyl)amino]-5-(trifluoromethyl)benzoyl]glycine (made analogously to Example 122 with 2-(morpholinylcarbonyl)amino-5-trifluoromethyl-benzoic acid, see Example 116) (78 mg) was incorporated into Example 123 to give the title benzamide (30 mg). MS found: $(M+Na)^+$=644.6.

Example 125

2-((Azetidinylcarbonyl)amino)-N-[2-[[(cis)-2-[[4-(methylthio)benzoyl]amino]cyclohexyl]amino]-2-oxoethyl]-5-trifluoromethyl benzamide (125a) N-[2-[(1-Azetidinylcarbonyl)amino]-5-(trifluoromethyl)benzoyl]glycine (made analogously to Example 122 with 2-(azetidinylcarbonyl)amino-5-trifluoromethyl-benzoic acid, see Example 116) (72 mg) was incorporated into Example 123 to give the title benzamide (35 mg). MS found: $(M+H)^+$=592.5.

Example 126

Tert-butyl (cis)-3-({N-[2-[(1-pyrrolidinylcarbonyl)amino]-5-(trifluoromethyl)benzoyl]glycyl}amino)tetrahydro-2H-pyran-4-ylcarbamate (126a) 3,4-Epoxytetrahydropyran (*Tetrahedron* 1974, 4013) (1 g) was dissolved in MeOH (10 mL) prior to the addition of NaN$_3$ (3.9 g) and NH$_4$Cl (3.2 g) in water (1 mL). The mixture was heated at 85° C. for 18 h. After cooling, the solution was concentrated prior to the addition of CH$_2$Cl$_2$ (100 mL). The solids were filtered away and the filtrate was concentrated. The resulting residue was dissolved in EtOAc (10 mL) followed by the addition of Boc$_2$O (3 g) and 20% Pd(OH)$_2$ (500 mg). A hydrogen balloon was added and the mixture was stirred for 2 h. EtOAc was added and the solution was filtered before concentration. Flash chromatography of the resulting residue gave trans-4-(tert-butoxycarbonyl)aminotetrahydro-2H-pyran-3-ol (see also *J. Med. Chem.* 2001, 725) (900 mg). MS found: $(M+H)^+$=218.1.

(126b) The pyran-3-ol (900 mg) from above, Example 126a, was dissolved in CH$_2$Cl$_2$ and prior to the addition of triethylamine (1.73 mL). After cooling to 0° C., methanesulfonyl chloride (0.48 mL) was added dropwise. The solution was stirred for 2 h before 1N HCl was added. The organic layer was washed with 1 N HCl, NaHCO$_3$ solution, and brine. The organic layer was dried (MgSO$_4$), filtered, and concentrated. The resulting residue was dissolved in DMSO (10 mL) prior to the addition of NaN$_3$ (1.3 g). The solution was heated at 85° C. for 18 h. After cooling, EtOAc and water were added. The water layer was extracted with EtOAc. The EtOAc was washed with brine, dried, and concentrated. Flash chromatography of the resulting residue gave cis-3-azido-4-(tert-butoxycarbonyl)aminotetrahydro-2H-pyran (430 mg), which was taken forward. This solid was dissolved in MeOH (10 mL) prior to the addition of 10% Pd/C (300 mg). A hydrogen balloon was added and the solution was stirred for 1 h. The palladium was filtered and the solution was concentrated. A portion of the resulting residue (50 mg) was dissolved in DMF (2 mL). After cooling to 0° C., 4-methylmorpholine (0.13 mL) and N-[2-[(1-pyrrolidinylcarbonyl)amino]-5-(trifluoromethyl)benzoyl]glycine (Example 122)(91 mg) were added. After 5 min, BOP Reagent (132 mg) was added and the mixture was stirred at rt for 18 h. EtOAc was added along with 1 N HCl solution. The EtOAc layer was washed with 1 N HCl, NaHCO$_3$ solution, and brine. The EtOAc was dried (MgSO$_4$), filtered, and concentrated. Flash chromatography of the resulting residue gave the title compound (140 mg). MS found: (M+Na)$^+$=580.5.

Example 127

2-{[1-Pyrrolidinylcarbonyl]amino}-N-{2-[((cis)-4-{[4-(methylthio)benzyl]amino}tetrahydro-2H-pyran-3-yl)amino]-2-oxoethyl}-5-(trifluoromethyl)benzamide (127a) The carbamate (140 mg) from above, Example 126, was dissolved in CH$_2$Cl$_2$ (10 mL) and TFA (10 mL). After 0.5 h, the solution was concentrated. A portion (50 mg) of this residue was dissolved in THF (2 mL) prior to the addition of acetic acid (0.5 mL) and 4-(methylthio)benzaldehyde (20 mg). After 30 min, NaHB(OAc)$_3$ (27 mg) was added and the solution was stirred for 2 h. The solution was filtered and reverse phase HPLC purification (gradient elution, water/acetonitrile/TFA) provided the title benzamide (7 mg). MS found: (M+H)$^+$=594.5.

Example 128

Tert-butyl (cis)-3-({N-[2-[(1-azetidinylcarbonyl)amino]-5-(trifluoromethyl)benzoyl]glycyl}amino)tetrahydro-2H-pyran-4-ylcarbamate (128a) N-[2-[(l-Azetidinylcarbonyl)amino]-5-(trifluoromethyl)benzoyl]glycine (made analogously to Example 122 with 2-(azetidinylcarbonyl)amino-5-trifluoromethylbenzoic acid, see Example 116) (209.3 mg) was incorporated into Example 126 to give the title carbamate (123.7 mg). MS found: (M+Na)$^+$=566.4.

Example 129

2-{[1-Azetidinylcarbonyl]amino}-N-{2-[((cis)-4-{[4-(methylthio)benzyl]amino}tetrahydro-2H-pyran-3-yl)amino]-2-oxoethyl}-5-(trifluoromethyl)benzamide (129a) The carbamate (80 mg), Example 128, from above was incorporated into Example 127 to give the title benzamide (11 mg). MS found: (M+H)$^+$=580.5.

Example 130

2-{[1-Azetidinylcarbonyl]amino}-N-{2-[((cis)-4-{[4-(methoxy)benzyl]amino}tetrahydro-2H-pyran-3-yl)amino]-2-oxoethyl}-5-(trifluoromethyl)benzamide (130a) Anisaldehyde (43 mg) was incorporated into Example 129 to give the title benzamide (36 mg). MS found: (M+H)$^+$=564.4.

Example 131

1-(4-Methylthiobenzoylamino)-2-[2-(2-amino-5-trifluoromethylbenzoylamino)-acetylamino]-4-aminocyclohexane (131a) (Cis)-N-benzyl-2,2,2-trifluoro-N-(7-oxa-bicyclo[4.1.0]hept-3-yl) acetamide (M. Chini et al., *J. Org. Chem.* 1990, 55, 4265-4272) (3.7 g) was dissolved in methanol (50 mL) prior to addition of NaN$_3$ (1.6 g) in H$_2$O (5 mL). The flask was fitted with a condenser and heated at reflux for 2 h. The cooled solution was partitioned between EtOAc and water and the organic layer was washed with NaHCO$_3$ and brine. The organic layer was dried, filtered, and concentrated. Flash chromatography of the resulting residue provided N-(3-azido-4-hydroxycyclohexyl)-N-benzyl-2,2,2-trifluoroacetamide (3.1 g). MS found: (M+Na)$^+$=378.2.

(131b) A portion of the above derivative (131a) (3.1 g) was dissolved in THF (20 mL) prior to addition of PPh$_3$ (3.6 g). The solution was stirred at rt for 12 h and water (5 mL) was added. The solution was stirred for an additional 12 h, and partitioned between EtOAc and water. The water layer was treated with 2 N NaOH until the pH=9 and was extracted EtOAc (3×). The combined organic extracts were dried, filtered and concentrated. The residue was partially purified by flash chromatography and was dissolved in THF (160 mL) and water (40 mL). The solution was treated with NaHCO$_3$ (3 g) prior to addition of di-tert-butyl dicarbonate (4.7 g). The solution was stirred for 8 h, partitioned between EtOAc and water, and the organic layer was washed with NaHCO$_3$ and brine. The organic layer was dried, filtered, and concentrated. Flash chromatography of the residue provided {5-[benzyl-(2,2,2-trifluoroacetyl)amino]-2-hydroxycyclohexyl}carbamic acid tert-butyl ester (3.1 g). MS found: (M+Na)$^+$=439.1.

(131c) The above derivative (131b) (3.1 g) was dissolved in methanol (100 mL) prior to addition of KOH (3 g), dissolved in water (50 mL). The flask was fitted with a condenser and heated at reflux for 2 h. The cooled solution was partitioned between EtOAc and water. The water layer was extracted with EtOAc (3×). The combined organic extracts were dried, filtered, and concentrated. The residue was dissolved in methanol (100 mL) prior to addition of 5% Pd/C (0.5 g). This reaction was placed on a Parr apparatus at 50 psi hydrogen pressure. After shaking for 8 h, the Pd/C was filtered off and the solution was concentrated. The residue was dissolved in THF (80 mL) and water (20 mL). The solution was treated with NaHCO$_3$ (1.7 g) prior to addition of benzyl chloroformate (1.3 mL). The solution was stirred for 8 h, and partitioned between EtOAc and water. The organic layer was washed with NaHCO$_3$ and brine. The organic layer was dried, filtered, and concentrated. Flash chromatography of the residue provided (3-tert-butoxycarbonylamino-4-hydroxycyclohexyl)carbamic acid benzyl ester (2.75 g). MS found: (M+Na)$^+$=387.2. (131d) A stirred solution of PPh$_3$ (2.3 g) was dissolved in THF (20 mL) and cooled to 0° C. prior to the dropwise addition of DEAD (1.4 mL). The solution was stirred for 0.5 h and combined with a solution of the above derivative (131c) (1.6 g) in THF (10 mL) and 10% HN3 in benzene (10.5 mL). The solution was stirred for 4 h and partitioned between EtOAc and water. The organic layer was washed with NaHCO$_3$ and brine. The organic layer was dried, filtered, and concentrated. Flash chromatography of the residue provided (2-azido-5-benzyloxycarbonylaminocyclohexyl)carbamic acid tert-butyl ester (1.6 g). MS found: (M+Na)$^+$=412.2.

(131e) The above derivative (131d) (1.5 g) was dissolved in THF (50 mL) prior to addition of PPh$_3$ (1.5 g). The solution was stirred at rt for 12 h and water (5 mL) was added. The solution was stirred for 12 h and partitioned between EtOAc and water. The water layer was treated with 2 N NaOH until the pH=9 and was extracted with EtOAc (3×). The combined organic extracts were dried, filtered, and concentrated. Flash chromatography of the residue provided (2-amino-5-benzyloxycarbonylaminocyclohexyl)carbamic acid tert-butyl ester (1.1 g). MS found: $(M+H)^+$=364.2.

(131f) A portion of the above derivative (131e) (150 mg) was dissolved in DMF (2 mL) prior to addition of Hunig's base (0.5 mL). 4-(thiomethyl)benzoic acid (140 mg) was added followed by HATU (470 mg). The solution was stirred for 8 h then quenched with aqueous NH$_4$Cl. The mixture was partitioned between EtOAc and water. The organic layer was washed with NaHCO$_3$, 5% LiCl (3×), and brine. The organic layer was dried, filtered, and concentrated. Flash chromatography of the residue provided [3-tert-butoxycarbonylamino-4-(4-methylthio-benzoylamino)cyclohexyl]carbamic acid benzyl ester (198 mg). MS found: $(M+H)^+$=514.2.

(131g) A portion of the above derivative (131f) (198 mg) was dissolved in CH$_2$Cl$_2$ (10 mL) prior to addition of TFA (10 mL). The solution was stirred for 4 h, and concentrated. The residue was dissolved in DMF (2 mL) prior to addition of Hunig's base (0.5 mL). (2-tert-Butoxycarbonylamino-5-trifluoromethylbenzoylamino)acetic acid (181 mg) was added followed by HATU (470 mg). The solution was stirred for 8 h and quenched with aqueous NH$_4$Cl. The mixture was partitioned between EtOAc and water. The organic layer was washed with NaHCO$_3$, 5% LiCl (3×), and brine. The organic layer was dried, filtered, and concentrated. Flash chromatography of the residue provided [2-({[5-benzyloxycarbonylamino-2-(4-methylthio-benzoylamino)cyclohexylcarbamoyl]-methyl}carbamoyl)-4-trifluoromethylphenyl]carbamic acid tert-butyl ester (250 mg). MS found: $(M+H)^+$=758.1.

(131h) A portion of the above derivative (131g) (250 mg) was dissolved in HOAc (3 mL) prior to addition of 38% HBr (3 mL). The solution was stirred for 12 h and poured into NaHCO$_3$ (100 mL). The solution was adjusted to pH=9 with 2 N NaOH and extracted with EtOAc. The organic layer was dried, filtered, and concentrated. Flash chromatography of the residue provided the title compound (120 mg). MS found: $(M+H)^+$=524.3.

Example 132

{4-(4-Methylthiobenzoylamino)-3-[2-(3-trifluoromethylbenzoylamino)-acetylamino]-4-aminocyclohexane (132a) (3-Trifluoromethylbenzoylamino) acetic acid (77 mg) was incorporated into Example 131, step (131g). Flash chromatography of the residue provided {4-(4-methylthiobenzoylamino)-3-[2-(3-trifluoromethylbenzoylamino)acetylamino]-cyclohexyl}carbamic acid benzyl ester (47 mg). MS found: $(M+H)^+$=643.2.

(132b) A portion of the above derivative (132a) (16 mg) was incorporated into Example 131, step (131h). Reverse phase HPLC purification (gradient elution, water/acetonitrile/TFA) of the residue provided the title compound (8 mg). MS found: $(M+H)^+$=509.2.

Example 133

1-(4-Methanesulfonylbenzoylamino)-2-[2-(3-trifluoromethylbenzoylamino)-acetylamino]cyclohexyl-4-aminocyclohexane (133a) A portion of the above derivative (132a) (51 mg) was dissolved in CH$_2$Cl$_2$ (20 mL) prior to addition of K$_2$CO$_3$ (138 mg) and 50% m-CPBA (86 mg). The mixture was stirred for 8 h and quenched with aqueous sodium thiosulfate. The organic layer was washed with NaHCO$_3$ and brine. The organic layer was dried, filtered, and concentrated. The residue was dissolved in CH$_2$Cl$_2$ (10 mL) prior to addition of TFA (10 mL). The solution was stirred for 4 h and concentrated. The residue was dissolved in DMF (2 mL) prior to addition of Hunig's base (0.2 mL). (3-trifluoromethylbenzoylamino) acetic acid (77 mg) was added followed by HATU (150 mg). The solution was stirred for 8 h, and quenched with aqueous NH$_4$Cl. The mixture was partitioned between EtOAc and water. The organic layer was washed with NaHCO$_3$, 5% LiCl (3×), and brine. The organic layer was dried, filtered, and concentrated. Flash chromatography of the residue provided {4-(4-Methanesulfonylbenzoylamino)-3-[2-(3-trifluoromethylbenzoylamino)acetylamino]-cyclohexyl}carbamic acid benzyl ester (41 mg). MS found: $(M+H)^+$=675.2.

(133b) A portion of the above derivative (133a) (35 mg) was incorporated into Example 131, step (131h). Reverse phase HPLC purification (gradient elution, water/acetonitrile/TFA) of the residue provided the title compound (14 mg). MS found: $(M+H)^+$=541.2.

Example 134

1-(4-Methylthiobenzoylamino)-2-[2-(2-amino-5-trifluoromethylbenzoylamino)acetylamino]-4-(2-propylamino)cyclohexane (134a) A portion of the above derivative (131h) (35 mg) was dissolved in methanol (0.5 mL) prior to addition of HC(OCH$_3$)$_3$ (2 mL) and acetone (0.2 mL). The solution was stirred for 1 h and NaBH(OAc)$_3$ (100 mg) was added. The solution was stirred for 12 h and poured into NaHCO$_3$ (10 mL). The solution was adjusted to pH=9 with 2 N NaOH and extracted with EtOAc. The organic layer was dried, filtered, and concentrated. Reverse phase HPLC purification (gradient elution, water/acetonitrile/TFA) of the residue provided the title compound (14 mg). MS found: $(M+H)^+$=566.1.

Example 135

1-(4-Methylthiobenzoylamino)-2-[2-(2-amino-5-trifluoromethylbenzoylamino)acetylamino]-4-(3-methylureido)cyclohexane (135a) A portion of the above derivative (131h) (35 mg) was dissolved in CH$_2$Cl$_2$ (5 mL) prior to addition of Hunig's base (0.2 mL). Methyl isocyanate (40 mg) was added and the solution was stirred for 4 h. The solution was poured into NaHCO$_3$ (10 mL) and EtOAc 20 mL). The organic layer was dried, filtered and concentrated. Reverse phase HPLC purification (gradient elution, water/acetonitrile/TFA) of the residue provided the title compound (10 mg). MS found: $(M+H)^+$=581.0.

Example 136

1-(4-Methylthiobenzoylamino)-2-[2-(3-trifluoromethylbenzoylamino)acetylamino]6-aminocyclohexane (136a) A portion of the above derivative (131e) (100 mg) was dissolved in DMF (2 mL) prior to addition of Hunig's base (0.3 mL). (3-trifluoromethyl-benzoylamino)-acetic acid (136 mg) was added followed by HATU (310 mg). The solution was stirred for 8 h and quenched with NH$_4$Cl. The mixture was partitioned between EtOAc and water. The organic layer was washed with NaHCO$_3$, 5% LiCl (3×), and brine. The organic layer was dried, filtered and concentrated. Flash chromatography of the residue provided {5-benzyloxycarbonylamino-2-[2-(3-trifluoromethylbenzoylamino)acetylamino]-cyclohexyl}carbamic acid tert-butyl ester (140 mg). MS found: (M+H)$^+$=593.3.

(136b) A portion of the above derivative (136a) (136 mg) was dissolved in CH$_2$Cl$_2$ (10 mL) prior to addition of TFA (10 mL). The solution was stirred for 4 h, and concentrated. The residue was dissolved in DMF (2 mL) prior to addition of Hunig's base (0.3 mL). 4-(thiomethyl)benzoic acid (77 mg) was added followed by HATU (262 mg). The solution was stirred for 8 h and quenched with aqueous NH$_4$Cl. The mixture was partitioned between EtOAc and water. The organic layer was washed with NaHCO$_3$, 5% LiCl (3×), and brine. The organic layer was dried, filtered, and concentrated. Flash chromatography of the residue provided {3-(4-methylthiobenzoylamino)-4-[2-(3-trifluoromethylbenzoylamino)acetylamino]cyclohexyl}carbamic acid benzyl ester (56 mg). MS found: (M+H)$^+$=643.3.

(136c) A portion of the above derivative (136b) (31 mg) was incorporated into Example 131, step (131h). Reverse phase HPLC purification (gradient elution, water/acetonitrile/TFA) of the residue provided the title compound (22 mg). MS found: (M+H)$^+$=509.2.

Example 137

1-(4-Methylthiobenzoylamino)-2-[2-(3-trifluoromethylbenzoylamino)acetylamino]6-(2-propylamino)cyclohexane (137a) A portion of the above derivative (136c) (15 mg) was incorporated into Example 134, step (134a). Reverse phase HPLC purification (gradient elution, water/acetonitrile/TFA) of the residue provided the title compound (13 mg). MS found: (M+H)$^+$=551.0.

Example 138

1-(4-Methylthio-benzoylamino)-2-[2-(2-Amino-5-trifluoromethyl-benzoylamino)-acetylamino]-4-aminocyclohexane (138a) (Cis)-N-benzyl-2,2,2-trifluoro-N-(7-oxa-bicyclo[4.1.0]hept-3-yl)acetamide (M. Chini et al., J. Org. Chem. 1990, 55, 4265-4272) (1.2 g) was incorporated into Example 131, step (131a). The residue was purified by flash chromatography to provide N-(4-azido-3-hydroxycyclohexyl)-N-benzyl-2,2,2-trifluoroacetamide (785 mg). MS found: (M+Na)$^+$=378.2.

(138b) A portion of the above derivative (138a) (785 mg) was incorporated into Example 131, step (131b). The residue was purified by flash chromatography to provide {4-[benzyl-(2,2,2-trifluoroacetyl)-amino]-2-hydroxycyclohexyl}carbamic acid tert-butyl ester (765 mg). MS found: (M−H)$^-$=415.0.

(138c) A portion of the above derivative (138b) (765 mg) was incorporated into Example 131, step (131c). The residue was purified by flash chromatography to provide (4-tert-butoxycarbonylamino-3-hydroxycyclohexyl)carbamic acid benzyl ester (580 mg). MS found: (M+H)$^+$=365.2.

(138d) A portion of the above derivative (138c) (530 mg) was incorporated into Example 131, step (131d). The residue was purified by flash chromatography to provide (2-azido-4-benzyloxycarbonylaminocyclohexyl)carbamic acid tert-butyl ester (480 mg). MS found: (M+Na)$^+$=412.2.

(138e) A portion of the above derivative (138d) (380 mg) was incorporated into Example 131, step (131e). The residue was purified by flash chromatography to provide (3-amino-4-tert-butoxycarbonylaminocyclohexyl)carbamic acid benzyl ester (320 mg). MS found: (M+H)$^+$=364.2.

(138f) The above derivative (138e) (80 mg) was incorporated into Example 131, step (131g). Flash chromatography of the residue provided {4-benzyloxycarbonylamino-2-[2-(2-tert-butoxycarbonylamino-5-trifluoromethylbenzoylamino)acetylamino]cyclohexyl}carbamic acid tert-butyl ester (97 mg). MS found: (M−H)$^-$=706.4.

(138g) The derivative (138f) (97 mg) was incorporated into Example 136, step (136b). Flash chromatography of the residue provided [3-[2-(2-amino-5-trifluoromethyl-benzoylamino)acetylamino]-4-(4-methylsulfanylbenzoylamino)cyclohexyl]carbamic acid benzyl ester (80 mg). MS found: (M+H)$^+$=658.2.

(138h) The derivative (138g) (60 mg) was incorporated into Example 131, step (131h): Reverse phase HPLC purification (gradient elution, water/acetonitrile/TFA) of the residue provided the title compound (16 mg). MS found: (M+H)$^+$=524.3.

Example 139

4-(4-Methylthiobenzoylamino)-3-[2-(3-trifluoromethylbenzoylamino)acetylamino]-4-aminocyclohexane (139a) A portion of the above derivative (138e) (50 mg) incorporated into Example 136, step (136b). The organic layer was dried, filtered, and concentrated. Flash chromatography of the residue provided {4-benzyloxycarbonylamino-2-[2-(3-trifluoromethylbenzoylamino)-acetylamino]cyclohexyl}carbamic acid tert-butyl ester (74 mg). MS found: (M+H)$^+$=593.3.

(139b) A portion of the derivative (139a) (70 mg) was incorporated into Example 136, step (136b) Reverse phase HPLC purification (gradient elution) of the residue provided {4-(4-methylthiobenzoylamino)-3-[2-(3-trifluoromethylbenzoylamino)acetylamino]-cyclohexyl}carbamic acid benzyl ester (20 mg). MS found: (M+H)$^+$=643.2.

(139c) A portion of the above derivative (139b) (60 mg) was incorporated into Example 131, step (131h). Reverse phase HPLC purification (gradient elution, water/acetonitrile/TFA) of the residue provided the title compound (28 mg). MS found: (M+H)$^+$=509.3.

Example 140

4-(4-Methylthiobenzoylamino)-3-[2-(3-trifluoromethylbenzoylamino)acetylamino]-4-(2-propylamino)-cyclohexane (140a) The derivative (139c) (15 mg) was incorporated into Example 134, step (134a). Reverse phase HPLC purification (gradient elution, water/acetonitrile/TFA) of the residue provided the title compound (11 mg). MS found: (M+H)$^+$=551.2.

Example 141

1-(4-Methylthiobenzoylamino)-2-[2-(3-trifluoromethylbenzoylamino)acetylamino]-5-aminocyclohexane (141a) The derivative (138e) (35 mg) was incorporated into Example 131, step (131f). Flash chromatography of the residue provided [4-benzyloxycarbonylamino-2-(4-methylthiobenzoylamino)cyclohexyl]carbamic acid tert-butyl ester (44 mg). MS found: $(M+H)^+=514.2$.

(141b) The above derivative (141a) (40 mg) was incorporated into Example 132, step (132a). The residue was triturated with EtOAc and collected on a sintered glass frit to provide the title compound {3-(4-methylthiobenzoylamino)-4-[2-(3-trifluoromethylbenzoylamino)acetylamino]cyclohexyl}carbamic acid benzyl ester (43 mg). MS found: $(M+H)^+=643.3$.

(141c) The above derivative (141b) (40 mg) was incorporated into Example 131, step (131h). Reverse phase HPLC purification (gradient elution, water/acetonitrile/TFA) of the residue provided the title compound (15 mg). MS found: $(M+H)^+=509.1$.

Example 143

[2-Isopropylamino-5-(trifluoromethyl)]benzoic acid (143a) Isopropylamine (4.0 mL) was dissolved in THF (20 mL). This solution was cooled to 0° C. and n-butyllithium (2.5 M, 20 mL) was added. The reaction was stirred for 90 min, then transferred to a solution of [2-fluoro-5-(trifluoromethyl)]benzoic acid (4.2 g) in THF (40 mL) at −78° C. This mixture was stirred for 15 min and the reaction was quenched with aqueous NH4Cl. The mixture was extracted with EtOAc (3×). The organic layer was dried, filtered, and concentrated. Flash chromatography of the resulting residue provided the title compound (2.4 g). MS found: $(M+H)^+=248.2$.

Example 144

2-Isopropylamino-N-{[(cis)2-(4-methylthiobenzylamino)-cyclohexylcarbamoyl]-methyl}-5-trifluoromethyl-benzamide (144a) N-tert-Butyloxycarbonylcyclohexane-(cis)-1,2-diamine (518 mg) was dissolved in CH$_2$Cl$_2$ (45 mL) and DMF (15 mL) prior to the addition of Hunig's base (1.7 mL) and ([2-(isopropylamino)-5-(trifluoromethyl)benzoylamino] acetic acid (incorporated Example 143 into Example 122) (400 mg) and HATU (1.84 g) at rt. The reaction was stirred for 8h and quenched with water. The organic layer was washed with 1 N HCl, aqueous NaHCO$_3$, 5% aqueous LiCl, and brine. The organic layer was dried, filtered, and concentrated. Flash chromatography of the residue provided cis-{2-[2-(2-isopropylamino-5-trifluoromethylbenzoylamino)-acetylamino]cyclohexyl}carbamic acid tert-butyl ester (534 mg). MS found: $(M-Boc+H)^+=401.1$.

(144b) The above derivative (144a) (150 mg) was dissolved in CH$_2$Cl$_2$ (12 mL) and cooled to 0° C. Trifluoroacetic acid (4 mL) was added and the reaction was warmed to rt, stirred for 1 h and concentrated. The residue was dissolved in CH$_2$Cl$_2$, washed with aqueous NH$_4$OH, and concentrated. The residue was dissolved in trimethylorthoformate (3 mL) prior to the addition of 4-methylsulfanylbenzaldehyde (400 μL). After 6 h, NaBH$_4$ (113 mg) was added. The reaction was stirred for 12 h, quenched with water and extracted with CH$_2$Cl$_2$ (3×). The CH$_2$Cl$_2$ layer was washed with aqueous NH$_4$Cl and brine. The organic layer was dried, filtered, and concentrated. Flash chromatography of the residue provided 2-isopropylamino-N-{[(cis)2-(4-methylthiobenzylamino)-cyclohexylcarbamoyl]-methyl}-5-trifluoromethylbenzamide (114 mg). MS found: $(M+H)^+=537.2$.

Example 145

2-(3-Isopropylureido)-N-{[2-(4-methylthiobenzylamino)cyclohexylcarbamoyl]-methyl}-5-trifluoromethylbenzamide (145a) [2-(3-Isopropylureido)-5-trifluoromethylbenzoylamino]acetic acid was incorporated into Example 144, step (144a) to give (2-(cis)-[2-[2-(3-isopropylureido)-5-trifluoromethylbenzoylamino]acetylamino]cyclohexyl)carbamic acid tert-butyl ester (404 mg). MS found: $(M-Boc+H)^+=444.0$.

(145b) The above derivative (145a) was incorporated into Example 144, step (144b). Reverse phase HPLC purification (gradient elution, water/acetonitrile/TFA) of the residue provided the title compound (75 mg). MS found: $(M+H)^+=580.1$.

Example 146

2-(3-Morpholinylureido)-N-{[2-(4-methylthiobenzylamino)cyclohexylcarbamoyl]-methyl}-5-trifluoromethylbenzamide (146a) {2-[(Morpholinylcarbonyl)amino]-5-trifluoromethylbenzoylamino}acetic acid was incorporated into Example 144, step (144a) to provide cis-[2-(2-{2-[(morpholine-4-carbonyl)-amino]-5-trifluoromethylbenzoylamino}acetylamino)cyclohexyl]carbamic acid tert-butyl ester (606 mg). MS found: $(M-Boc+H)^+=472.0$.

(146b) The above derivative (146a) was incorporated into Example 144, step (144b). Reverse phase HPLC purification (gradient elution, water/acetonitrile/TFA) of the resulting residue provided the title compound (58 mg). MS found: $(M+H)^+=608$.

Example 151

2-amino-N-{2-[((3S,4R)-4-{[4-(methylthio)benzyl]amino}-1-propyl-3-piperidinyl)amino]-2-oxoethyl}-5-(trifluoromethyl)benzamide (151a) 1-Tert-butoxycarbonyl-4-azido-3-hydroxy-piperidine (Marquis et al. *J. Med. Chem.* 2001, 44, 725) (39.6 g) was dissolved in MeOH (500 mL) prior to the addition of 10% Pd/C (10 g) in a Parr bottle. The reaction was shaken at 50 psi overnight. The reaction was filtered and the volatiles were removed under reduced pressure. The resulting residue (35.4 g) was dissolved in THF (1000 mL) and water (240 mL) along with Et$_3$N (68.6 mL) and (Cbz)$_2$O (52 g). The reaction was stirred at ambient temperature overnight and the volatiles were removed under reduced pressure. The resulting material was taken into ether and washed with 10% aqueous citric acid, water, saturated aqueous sodium bicarbonate, brine, dried over MgSO$_4$, and the volatiles were removed under reduced pressure. Flash chromatography of the resulting residue gave 1-tert-butoxycarbonyl-4-(benzyloxycarbonyl)amino-3-hydroxy-piperidine (37.2 g) as the faster eluting isomer 1e. MS found: $(M+Na)^+=534.5$.

(151b) To a stirred, cooled (5° C. water bath) solution of 2.81 grams of triphenylphosphine in 80 mL of benzene was added 1.82 mL of DEAD dropwise over 5 minutes. After stirring 15 minutes at 5° C. a premixed solution of 3 grams of 151a (from above) in 40 mL THF and 80 mL of ~2.3 molar HN3 in benzene was added over 20 minutes. The reaction was stirred at ambient temperature overnight. Ether was added and the mixture was washed with saturated aqueous sodium bicarbonate, water, brine and dried over $MgSO_4$. The volatiles were removed under reduced pressure. The resulting material (combined from two runs) was dissolved in THF (400 mL) and triphenylphosphine (13.5 g) was added along with 4 mL of water. The reaction was stirred at 65° C. for 14 hours and the volatiles were removed under reduced pressure. The material was taken into ether and extracted 4 times with 0.1M aqueous HCl. The combined aqueous layers were washed twice with ether and made basic (pH>9) by the addition of sodium bicarbonate. The resulting slurry was extracted three times with ether, dried over $MgSO_4$ and the volatiles were removed under reduced pressure affording 3 grams of 1-tert-butoxycarbonyl-3-amino-4-(benzyloxycarbonyl)amino-piperidine. MS found: $(M+H)^+=350.4$.

(151c) The above material (151b, 2.0 g) was dissolved in DMF (40 mL) prior to the addition of NMM (1.9 mL), N-[2-[(1-t-butoxycarbonyl)amino]-5-(trifluoromethyl)benzoyl] glycine (see Example 122) (2.3 g), and HATU (2.3 g). After stirring overnight at ambient temperature the volatiles were removed under reduced pressure and resulting material was slurried in ether and washed with 10% aqueous citric acid, water, saturated aqueous sodium bicarbonate, brine, dried over $MgSO_4$, and the volatiles were removed under reduced pressure. This resulted in tert-butyl (cis)-4-{[(benzyloxy)carbonyl]amino}-3-{[1-{[2-[(tert-butoxycarbonyl)amino]-5-(trifluoromethyl)benzoyl]amino}2-oxoethyl]amino}-1-piperidinecarboxylate (4.05 g). MS found: $(M+H)^+=692.4$.

(151d) The above material (151c) (13.4 g) was dissolved in $CH_2Cl_2$ (50 mL) and TFA (50 mL). After stirring for 30 minutes, the volatiles were removed under reduced pressure. The resulting residue was dissolved in $CH_3CN$ (200 mL) prior to the addition of potassium carbonate (10.7 g) and allylbromide (1.83 mL). The reaction was stirred at ambient temperature overnight, the mixture was filtered and the volatiles were removed under reduced pressure. The material was dissolved in ether and washed with water, saturated aqueous brine, dried over $MgSO_4$. The volatiles were removed under reduced pressure affording benzyl (cis)-1-allyl-3-{[1-{[2-amino-5-(trifluoromethyl)benzoyl]amino}2-oxoethyl]amino}-4-piperidinylcarbamate (8 g). MS found: $(M+H)^+=534.5$.

(151e) The above material (151d) (8.0 g) was dissolved in MeOH (100 mL) prior to the addition of 10% Pd/C (8 g). This was stirred under hydrogen (balloon) for 6 hours. The mixture was filtered and the volatiles removed under reduced pressure. The resulting residue was dissolved in MeOH (250 mL) prior to the addition of 4-methylthiobenzaldehyde (1.78 mL), sodium cyanoborohydride (2.0 g), and zinc chloride (4.4 g). The reaction was stirred at ambient temperature overnight. The volatiles were removed under reduced pressure and resulting material was partitioned in ether and water. The ether phase was washed with water, then extracted 4× with 0.1N HCl. All the acidic extracts were combined and washed twice with ether, rendered basic (pH>8.5) by the addition of sodium bicarbonate, extracted three times with dichloromethane, dried over $MgSO_4$, and the volatiles were removed under reduced pressure. The resulting material was chromatographed on silica gel eluting with a gradient of 2-5% methanol/chloroform affording 1.8 grams as the mixture of enantiomers. The mixture was chromatographed on a chiracel OD column eluting with 15% ethanol/hexane. The faster enantiomer was collected, the volatiles were removed under reduced pressure and the resulting material was lypholized from a mixture of water/TFA affording the title benzamide (0.98 g). MS found: $(M+H)^+=538.5$.

Example 152

2-Amino-N-{2-[((3R,4S)-4-{[4-(methylthio)benzyl]amino}-1-propyl-3-piperidinyl)amino]-2-oxoethyl}-5-(trifluoromethyl)benzamide (152a) The final chiracel OD column from above also gave this enantiomer (second) as the title compound. MS found: $(M+H)^+=538.5$.

Example 153

2-amino-N-{2-[((cis)-4-{[4-(methylthio)benzoyl]amino}-1-methyl-3-piperidinyl)amino]-2-oxoethyl}-5-(trifluoromethyl)benzamide (153a) MeI (0.58 mL of 0.10 g/mL solution in $CH_3CN$) was incorporated into Example 151d to give benzyl (cis)-1-methyl-3-{[1-{[2-amino-5-(trifluoromethyl)benzoyl]amino}2-oxoethyl]amino}-4-piperidinylcarbamate (107 mg). LRMS found $(M+H)^+=508.3$.

(153b) The above material (153a) (100 mg) was dissolved in MeOH (5 mL) prior to the addition of 10% Pd/C (100 mg). This was stirred under hydrogen (balloon) for 2 hours. The mixture was filtered and the volatiles removed under reduced pressure. The resulting residue was dissolved in DMF (1.5 mL) prior to the addition of NMM (0.032 mL), 4-methylthiobenzoic acid (0.018 g), and HATU (0.038 g). After stirring overnight at ambient temperature the volatiles were removed under reduced pressure. Reverse phase HPLC purification (gradient elution, water/acetonitrile/TFA) of the residue provided the title compound (29 mg). MS found: $(M+H)^+=524.4$.

Example 154

N-{2-[((cis)-4-{[4-chlorobenzyl]amino}-3-piperidinyl)amino]-2-oxoethyl}-3-(trifluoromethyl)benzamide (154a) (3-Trifluoromethylbenzoylamino) acetic acid and 4-chlorobenzaldehyde were incorporated into Example 151 (without the allyl bromide alkylation of step 151d) to give the title benzamide. MS found: $(M+H)^+=469.3$.

Example 155

N-{2-[((cis)-4-{[4-(methylthio)benzyl]amino}-3-piperidinyl)amino]-2-oxoethyl}-3-(trifluoromethyl)benzamide (155a) (3-Trifluoromethylbenzoylamino) acetic acid and 4-methylthiobenzaldehyde were incorporated into Example 151 (without the allyl bromide alkylation of step 151d) to give the title benzamide. MS found: $(M+H)^+=481.2$.

Example 156

2-Amino-N-{2-[((cis)-4-{[4-chlorobenzyl]amino}-3-piperidinyl)amino]-2-oxoethyl}-5-(trifluoromethyl)benzamide (156a) 4-Chlorobenzaldehyde was incorporated into Example 151 (without the allyl bromide alkylation of step 151d) to give the title benzamide. MS found: $(M+H)^+=484.4$.

Example 157

2-Amino-N-{2-[((cis)-4-{[4-methylthiobenzyl]amino}-3-piperidinyl)amino]-2-oxoethyl}-5-(trifluoromethyl)benzamide (157a) 4-Methylthiobenzaldehyde was incorporated into Example 151 (without the allyl bromide alkylation of step 151d) to give the title benzamide. MS found: $(M+H)^+=496.5$.

Example 158

2-Amino-N-{2-[((cis)-4-{[4-ethylthiobenzyl]amino}-3-piperidinyl)amino]-2-oxoethyl}-5-(trifluoromethyl)benzamide (158a) 4-Ethylthiobenzaldehyde was incorporated into Example 151 (without the allyl bromide alkylation of step 151d) to give the title benzamide. MS found: $(M+H)^+=510.5$.

Example 159

N-{2-[((cis)-4-{[4-methylthiobenzyl]amino}-1-methyl-3-piperidinyl)amino]-2-oxoethyl}-3-(trifluoromethyl)benzamide (159a) MeI and (3-Trifluoromethylbenzoylamino) acetic acid were incorporated into Example 151 to give the title benzamide. MS found: $(M+H)^+=493.3$.

Example 160

N-{2-[((cis)-4-{bis[4-methylthiobenzyl]amino}-1-methyl-3-piperidinyl)amino]-2-oxoethyl}-3-(trifluoromethyl)benzamide (160a) The final reverse phase HPLC purification from the procedure above (159a) also gave the title benzamide. MS found: $(M+H)^+=631.3$.

Example 161

2-Amino-N-{2-[((cis)-4-{[4-methylthiobenzyl]amino}-1-methyl-3-piperidinyl)amino]-2-oxoethyl}-5-(trifluoromethyl)benzamide (161a) MeI and was incorporated into Example 151 to give the title benzamide. MS found: $(M+H)^+=510.3$.

Example 162

N-{2-[((cis)-4-{[4-methylthiobenzyl]amino}-1-acetyl-3-piperidinyl)amino]-2-oxoethyl}-3-(trifluoromethyl)benzamide (162a) (3-Trifluoromethylbenzoylamino) acetic acid (substituted in step 151c) and acetyl chloride/Et$_3$N (substituted for allyl bromide/K$_2$CO$_3$, step 151d) were incorporated into Example 151 to give the title benzamide. MS found: $(M+H)^+=551.4$.

Example 163

2-Amino-N-{2-[((cis)-4-{[4-methylthiobenzyl]amino}-1-butyl-3-piperidinyl)amino]-2-oxoethyl}-5-(trifluoromethyl)benzamide (163a) Crotyl bromide and was incorporated into Example 151 to give the title benzamide. MS found: $(M+H)^+=552.5$.

Example 164

2-Cyclohexylamino-N-{2-[((cis)-4-{[4-methylthiobenzyl]amino}-1-propyl-3-piperidinyl)amino]-2-oxoethyl}-5-(trifluoromethyl)benzamide (164a) N-[2-[cyclohexylamino]-5-(trifluoromethyl)benzoyl]glycine (see Example 143 with cyclohexyl amine and Example 122) was incorporated into Example 151 to give the title benzamide. MS found: $(M+H)^+=620.6$.

Example 165

2-Iso-propylamino-N-{2-[((cis)-4-{[4-methylthiobenzyl]amino}-1-propyl-3-piperidinyl)amino]-2-oxoethyl}-5-(trifluoromethyl)benzamide (165a) N-[2-[Iso-propylamino]-5-(trifluoromethyl)benzoyl]glycine (see Example 143 and Example 122) was incorporated into Example 151 to give the title benzamide. MS found: $(M+H)^+=580.5$.

Example 166

2-(Pyrrolidinylcarbonyl)amino-N-{2-[((cis)-4-{[4-methylthiobenzyl]amino}-1-propyl-3-piperidinyl)amino]-2-oxoethyl}-5-(trifluoromethyl)benzamide (166a) 2-(Pyrrolidinylcarbonyl)amino-5-trifluoromethylbenzoic acid (see Example 122) was incorporated into Example 151 to give the title benzamide. MS found: $(M+H)^+=635.6$.

Example 167

2-(Methylaminocarbonyl)amino-N-{2-[((cis)-4-{[4-methylthiobenzyl]amino}-1-propyl-3-piperidinyl)amino]-2-oxoethyl}-5-(trifluoromethyl)benzamide (167a) 2-(Methylcarbonyl)amino-5-trifluoromethylbenzoic acid (see Example 122) was incorporated into Example 151 to give the title benzamide. MS found: $(M+H)^+=595.6$.

Example 168

3-Amino-N-{2-[((cis)-4-{[4-methylthiobenzyl]amino}-1-propyl-3-piperidinyl)amino]-2-oxoethyl}-5-(trifluoromethyl)benzamide (168a) 3-Amino-5-trifluoromethylbenzoic acid (see Example 122) was incorporated into Example 151 to give the title benzamide. MS found: $(M+H)^+=538.5$.

Example 169

N-{2-[((cis)-4-{[4-aminosulfonylbenzoyl]amino}-3-piperidinyl)amino]-2-oxoethyl}-3-(trifluoromethyl)benzamide (169a) 4-Aminosulfonylbenzoic acid (into step 153b) and (3-trifluoromethylbenzoylamino) acetic acid (into step 151c) were incorporated into Example 151 without step 151d (skip this step) to give the title benzamide. MS found: $(M+H)^+=528.3$.

Example 170

N-{2-[((cis)-4-{[4-methylsulfonylbenzoyl]amino}-3-piperidinyl)amino]-2-oxoethyl}-3-(trifluoromethyl)benzamide (170a) 4-Methylsulfonylbenzoic acid was incorporated into Example 169 to give the title benzamide. MS found: (M+H)⁺=527.0.

Example 171

2-Amino-N-{2-[((cis)-4-{[4-(methylthio)benzoyl]amino}-3-piperidinyl)amino]-2-oxoethyl}-5-(trifluoromethyl)benzamide (171a) N-[2-[(l-t-butoxycarbonyl)amino]-5-(trifluoromethyl)benzoyl]glycine was incorporated into Example 153 and step 151d was skipped to give the title benzamide. MS found: (M+H)⁺=510.3.

Example 172

N-{2-[((cis)-4-{[4-methylthiobenzoyl]amino}-1-methyl-3-piperidinyl)amino]-2-oxoethyl}-3-(trifluoromethyl)benzamide (172a) (3-Trifluoromethylbenzoylamino) acetic acid was incorporated into Example 153 (by way of 151c) to give the title benzamide. MS found: (M+H)⁺=509.3.

Example 173

N-{2-[((cis)-4-{[4-methylthiobenzoyl]amino}-1-acetyl-3-piperidinyl)amino]-2-oxoethyl}-3-(trifluoromethyl)benzamide (173a) Acetyl chloride/Et₃N was incorporated into Example 172 (via step 153a) to give the title benzamide. MS found: (M+H)⁺=559.3.

Example 174

2-Amino-N-{2-[((cis)-4-{[4-methylthiobenzoyl]amino}-1-butyl-3-piperidinyl)amino]-2-oxoethyl}-3-(trifluoromethyl)benzamide (174a) Crotyl bromide was incorporated into Example 153 (via step 153a) to give the title benzamide. MS found: (M+H)⁺=566.5.

Example 175

2-Cyclohexylamino-N-{2-[((cis)-4-{[4-methylthiobenzoyl]amino}-1-propyl-3-piperidinyl)amino]-2-oxoethyl}-5-(trifluoromethyl)benzamide (175a) N-[2-[cyclohexylamino]-5-(trifluoromethyl)benzoyl]glycine (see Example 143 with cyclohexyl amine and Example 122) and allyl bromide were incorporated into Example 153 to give the title benzamide. MS found: (M+H)⁺=634.6.

Example 176

2-Iso-propylamino-N-{2-[((cis)-4-{[4-methylthiobenzoyl]amino}-1-propyl-3-piperidinyl)amino]-2-oxoethyl}-5-(trifluoromethyl)benzamide (176a) N-[2-[iso-propylamino]-5-(trifluoromethyl)benzoyl]glycine (see Example 143 with i-propylamine and Example 122) and allyl bromide were incorporated into Example 153 to give the title benzamide. MS found: (M+H)⁺=594.4.

Example 177

3-Amino-N-{2-[((cis)-4-{[4-methylthiobenzoyl]amino}-1-propyl-3-piperidinyl)amino]-2-oxoethyl}-5-(trifluoromethyl)benzamide (177a) N-[3-(amino)-5-(trifluoromethyl)benzoyl]glycine (see Example 122) and allyl bromide were incorporated into Example 153 to give the title benzamide. MS found: (M+H)⁺=552.4.

Example 178

N-{2-[((cis)-3-{[4-(aminosulfonyl)benzoyl]amino}-4-piperidinyl)amino]-2-oxoethyl}-3-(trifluoromethyl)benzamide (178a) 1-tert-butoxycarbonyl-3-amino-4-(benzyloxycarbonyl)amino-piperidine (151b) (300 mg) was dissolved in DMF (5 mL) prior to addition of Hunig's base (0.45 mL). 4-(aminosulfonyl)benzoic acid (210 mg) was added followed by BOP (420 mg). The solution was stirred for 8 h then quenched with aqueous NH₄Cl. The mixture was partitioned between EtOAc and water. The organic layer was washed with NaHCO₃, 5% LiCl (3×), and brine. The organic layer was dried, filtered, and concentrated. Flash chromatography of the residue provided tert-butyl (cis)-3-{[4-(aminosulfonyl)benzoyl]amino}-4-{[(benzyloxy)carbonyl]amino}-1-piperidinecarboxylate (210 mg). MS found: (M−H)⁻=531.3.

(178b) The material from above (178a) (200 mg) was dissolved in CH₂Cl₂ (2 mL) prior to the addition of Pd(OAc)₂ (28 mg), Et₃SiH (0.29 mL), and Et₃N (0.02 mL). The solution was stirred overnight. This was quench with saturated NaHCO₃ and extracted with CH₂Cl₂. The organic layer was dried, filtered, and concentrated. The resulting residue was dissolved in DMF (1 mL) prior to addition of NMM (0.032 mL), (3-Trifluoromethylbenzoylamino)acetic acid (see Example 122) (29 mg), and HATU (42 mg). After stirring overnight at ambient temperature the volatiles were removed under reduced pressure and EtOAc was added. This was washed with 10% aqueous citric acid, water, saturated aqueous sodium bicarbonate, brine, dried over MgSO₄, and the volatiles were removed under reduced. This material was dissolved in CH₂Cl₂ (1 mL) prior to the addition of TFA (1 mL). After 1 h, the solution was concentrated. Reverse phase HPLC purification (gradient elution, water/acetonitrile/TFA) of the resulting residue provided the title benzamide. MS found: (M+H)⁺=528.1.

Example 179

N-{[4-Dimethylamino-2-(4-methylsulfanyl-benzylamino)-cyclohexylcarbamoyl]-methyl}-3-trifluoromethyl-benzamide trifluoroacetate (179a) Cis-4-(benzyloxy)-1,2-epoxycyclohexane (6 g) (Chini et al. *J. Org. Chem.* 1990, 55, 4265) was dissolved in MeOH (160 mL) prior to the addition of NaN₃ (9.5 g) and NH₄Cl (3.4 g) in water (20 mL). The mixture was heated at 85° C. for 18 h. After cooling, the solution was concentrated prior to the addition of CH₂Cl₂. The solids were filtered away and the filtrate was concentrated. A portion (500 mg) of the resulting residue was dissolved in EtOAc (10 mL) followed by the addition of Boc₂O (485 mg) and 20% Pd(OH)₂ (200 mg). A hydrogen balloon was added and the mixture was stirred for 2 h. EtOAc was added and the solution was filtered before concentration. This material was dissolved in CH₂Cl₂ (5 mL) and cooled to 0° C. prior to the addition of Et₃N (0.26 mL) and methanesulfonyl chloride (0.3 mL). After 2 h, the CH₂Cl₂ was removed and EtOAc was added. This was washed with 1N HCl, saturated NaHCO₃, and brine. The organic layer was dried, filtered, and concentrated. This solid was dissolved in DMSO (5 mL) prior to the addition of NaN₃ (326 mg). This was heated at 80° C. for 18 h. After cooling to 0° C., water was added and it was extracted with EtOAc. The organic layer was washed with brine, dried, filtered, and concentrated. Flash chromatography of the resulting residue gave (2-azido-5-benzyloxy-cyclohexyl)-carbamic acid tert-butyl ester (250 mg). MS found: (M+H)⁺=347.2.

(179b) The above material (3 g) was dissolved in MeOH (25 mL) prior to the addition of 10% Pd/C (2 g). A hydrogen balloon was added and the solution was stirred for 1.0 h. The palladium was filtered and the solution was concentrated. This material was dissolved in DMF prior to the addition of 4-methylmorpholine (6.7 mL) and 3-trifluoromethyl-benzoylamino)-acetic acid (3.3 g). After cooling to 0° C., BOP Reagent (7 g) was added. The resulting mixture was warmed to rt and was stirred overnight. EtOAc was added along with 1 N HCl solution (aq). The EtOAc layer was washed with 1 N HCl, NaHCO₃ solution (aq), and brine. The EtOAc was dried (MgSO₄), filtered, and concentrated. Flash chromatography of the resulting residue gave {5-benzyloxy-2-[2-(3-trifluoromethyl-benzoylamino)-acetylamino]-cyclohexyl}-carbamic acid tert-butyl ester (8 g). MS found: (M+Na)⁺=550.4.

(179c) The above material (6 g) was dissolved in MeOH (50 mL) prior to the addition of 10% Pd(OH)₂ (2.5 g). Hydrogen gas (50 psi) was added and the solution was shaken overnight. The palladium was filtered and the solution was concentrated (4.75 g). A portion (300 mg) of this material was dissolved in CH₂Cl₂ (5 mL) and cooled to 0° C. prior to the addition of Et₃N (0.26 mL) and methanesulfonyl chloride (0.08 mL). After 1 h, the CH₂Cl₂ was removed and EtOAc was added. This was washed with 1N HCl, saturated NaHCO₃, and brine. The organic layer was dried, filtered, and concentrated. This solid was dissolved in DMSO (5 mL) prior to the addition of NaN₃ (211 mg). This was heated at 80° C. for 18 h. After cooling to 0° C., water was added and it was extracted with EtOAc. The organic layer was washed with brine, dried, filtered, and concentrated. Flash chromatography of the resulting residue gave {5-azido-2-[2-(3-trifluoromethyl-benzoylamino)-acetylamino]-cyclohexyl}-carbamic acid tert-butyl ester (140 mg). MS found: (M+H)⁺=485.5.

(179d) The above material (135 mg) was dissolved in MeOH (5 mL) prior to the addition of 10% Pd/C (100 mg). A hydrogen balloon was added and the solution was stirred 1 h. The palladium was filtered and the solution was concentrated. This was dissolved in MeOH (5 mL) prior to the addition of 37% formaldehyde (106 mg) solution (aq). After 10 min, NaBH₃CN (49 mg) was added. The reaction was stirred for 2 h before the solution was concentrated. EtOAc was added along with some water. The organic layer was dried, filtered, and concentrated. This was dissolved in CH₂Cl₂ (5 mL) and TFA (5 mL). After 1 h, it was concentrated. This was dissolved in THF (2.5 mL) prior to the addition of 4-(methylthio) benzaldehyde (0.04 mL) and Hunig's base (0.1 mL). After 10 min, NaHB(OAc)₃ was added. The reaction was stirred for 2 h before the solution was filtered and concentrated. Reverse phase HPLC purification (gradient elution, water/acetonitrile/TFA) of the resulting residue gave the title compound (35 mg). MS found: (M+H)⁺=523.4.

Example 180

N-{[2-(4-Chloro-benzylamino)-4-dimethylamino-cyclohexylcarbamoyl]-methyl}-3-trifluoromethyl-benzamide trifluoroacetate (180a) 4-Chlorobenzaldehyde (17 mg) was incorporated into Example 179 to give the title compound (2.5 mg). MS found: (M+H)⁺=511.3.

Example 181

N-{[4-Dimethylamino-2-(4-methoxy-benzylamino)-cyclohexylcarbamoyl]-methyl}-3-trifluoromethyl-benzamide trifluoroacetate (181a) 4-(Methoxy)benzaldehyde (0.01 mL) was incorporated into Example 179 to give the title compound (3.5 mg). MS found: (M+H)⁺=507.4.

Example 182

N-{[4-Dimethylamino-2-(4-methyl-benzylamino)-cyclohexylcarbamoyl]-methyl}-3-trifluoromethyl-benzamide trifluoroacetate (182a) 4-(Methyl)benzaldehyde (0.01 mL) was incorporated into Example 179 to give the title compound (4.5 mg). MS found: (M+H)⁺=491.4.

Table 1 contains representative examples of the present invention. Each of the following structural formulas are to be used in the indicated example (Ex) range paired with the given R¹ and R² substituent.

TABLE 1

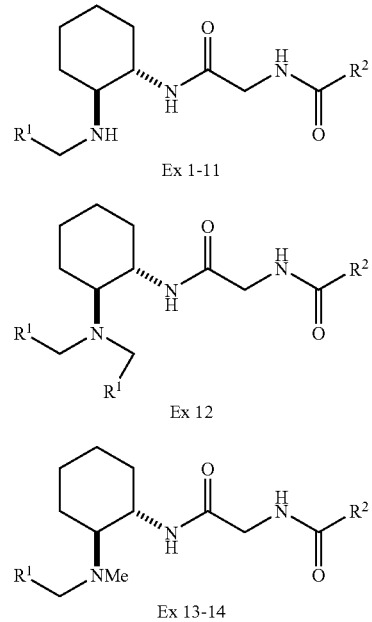

TABLE 1-continued
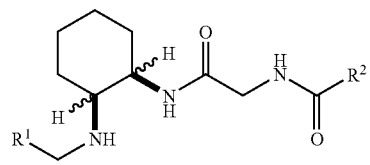
Ex 15-24, 144-146
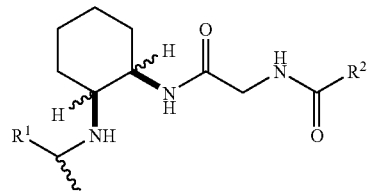
Ex 25
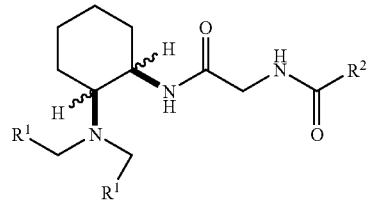
Ex 26
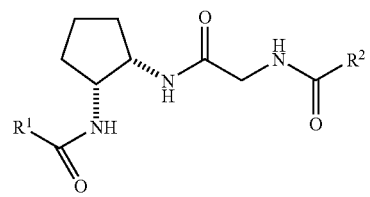
Ex 27-31
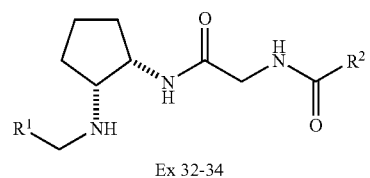
Ex 32-34
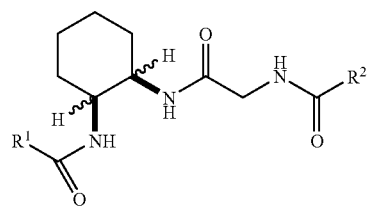
Ex 35-57; 61-125
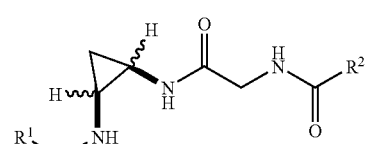
Ex 58-60
TABLE 1-continued
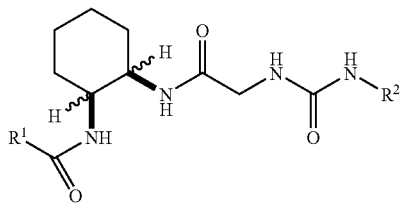
Ex 67
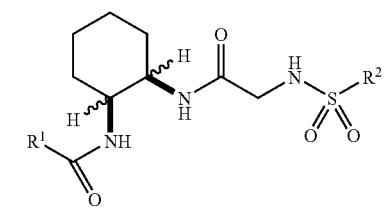
Ex 68
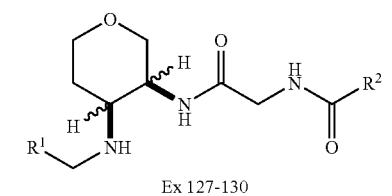
Ex 127-130
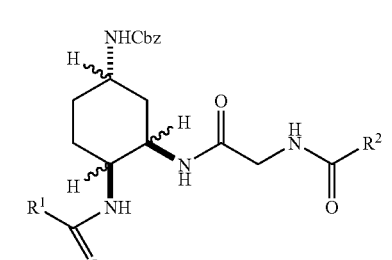
Ex 131g, 132a, 133a
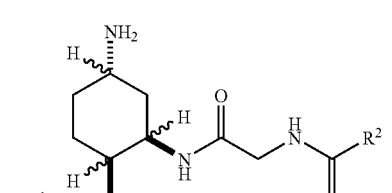
Ex 131-133
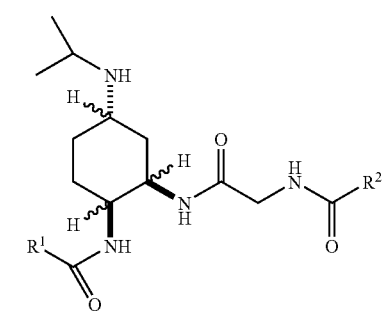
Ex 134

TABLE 1-continued
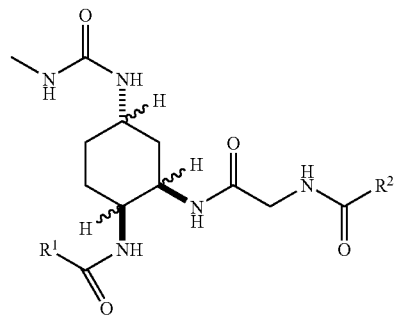
Ex 135
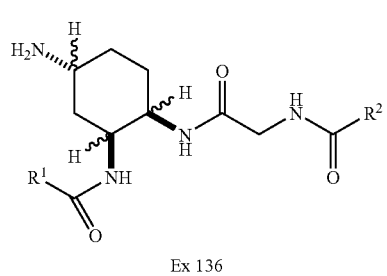
Ex 136
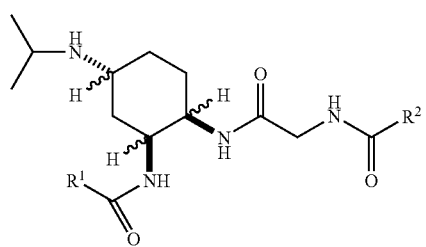
Ex 137
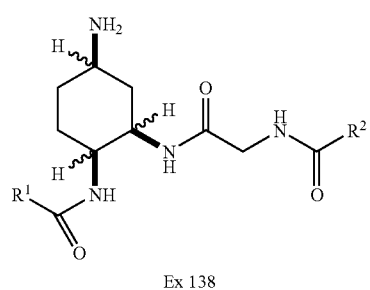
Ex 138
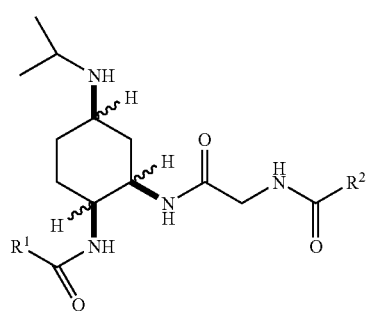
Ex 140
TABLE 1-continued
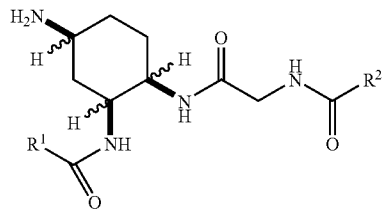
Ex 141
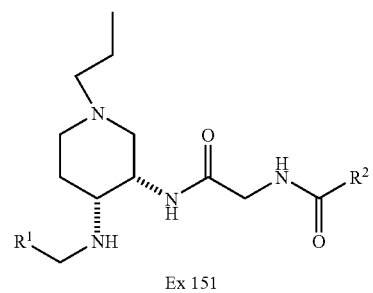
Ex 151
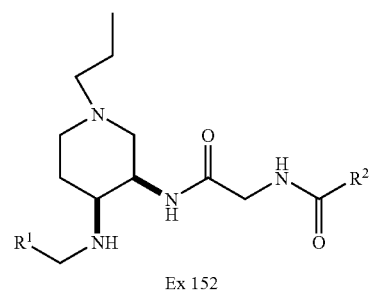
Ex 152
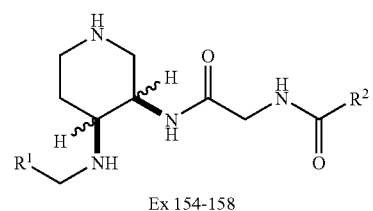
Ex 154-158
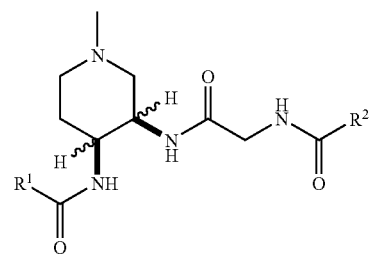
Ex 153, 172
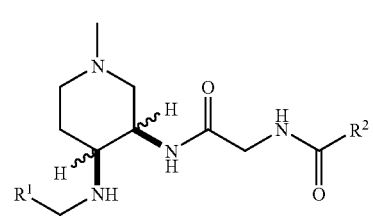
Ex 159, 161

TABLE 1-continued

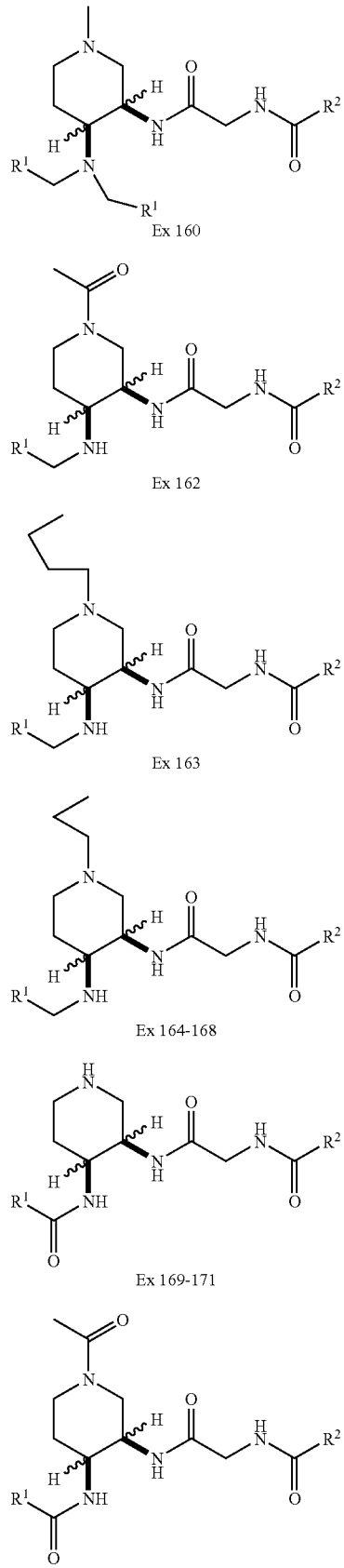

Ex 160

Ex 162

Ex 163

Ex 164-168

Ex 169-171

TABLE 1-continued

Ex 173

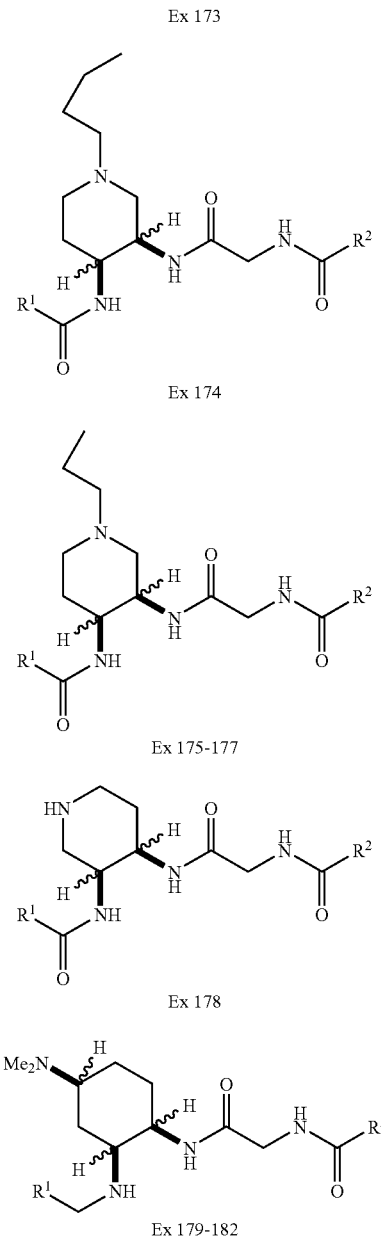

Ex 174

Ex 175-177

Ex 178

Ex 179-182

| Ex | R¹ | R² | MS [M + H] |
|---|---|---|---|
| 1 | 4-chlorophenyl | 3-trifluoromethylphenyl | 468.2 |
| 2 | 2,4-dimethylphenyl | 3-trifluoromethylphenyl | 462.3 |
| 3 | 2,4,6-trimethylphenyl | 3-trifluoromethylphenyl | 476.4 |
| 4 | 4-benzyloxyphenyl | 3-trifluoromethylphenyl | 540.4 |
| 5 | 2,4-difluorophenyl | 3-trifluoromethylphenyl | 470.3 |
| 6 | 2-chloro-4-fluorophenyl | 3-trifluoromethylphenyl | 486.2 |
| 7 | 4-fluoro-2-trifluoromethylphenyl | 3-trifluoromethylphenyl | 520.2 |
| 8 | 2,4-dichlorophenyl | 3-trifluoromethylphenyl | 502.1 |

TABLE 1-continued

| | | | |
|---|---|---|---|
| 9 | 2-fluoro-6-trifluoromethylphenyl | 3-trifluoromethylphenyl | 520.2 |
| 10 | 2-chloro-5-trifluoromethylphenyl | 3-trifluoromethylphenyl | 536.2 |
| 11 | 1-naphthyl | 3-trifluoromethylphenyl | 484.3 |
| 12 | 3-furyl | 3-trifluoromethylphenyl | 504.3 |
| 13 | 2,4-dimethylphenyl | 3-trifluoromethylphenyl | 476.3 |
| 14 | 4-chlorophenyl | 3-trifluoromethylphenyl | 482.3 |
| 15 | 2,4-dimethylphenyl | 3-trifluoromethylphenyl | 462.4 |
| 16 | 4-chlorophenyl | 3-trifluoromethylphenyl | 468.3 |
| 17 | 4-nitrophenyl | 3-trifluoromethylphenyl | 479.3 |
| 18 | 4-isopropylphenyl | 3-trifluoromethylphenyl | 476.3 |
| 19 | 4-trifluoromethylphenyl | 3-trifluoromethylphenyl | 502.3 |
| 20 | 4-trifluoromethoxy-phenyl | 3-trifluoromethylphenyl | 518.2 |
| 21 | 4-phenoxyphenyl | 3-trifluoromethylphenyl | 526.2 |
| 22 | 1-naphthyl | 3-trifluoromethylphenyl | 484.3 |
| 23 | 2-naphthyl | 3-trifluoromethylphenyl | 484.3 |
| 24 | 3-indolyl | 3-trifluoromethylphenyl | 473.3 |
| 25 | 4-chlorophenyl | 3-trifluoromethylphenyl | 482.2 |
| 26 | 3-furyl | 3-trifluoromethylphenyl | 504.3 |
| 27 | 4-chlorophenyl | 3-trifluoromethylphenyl | 468.2 |
| 28 | 4-methylthiophenyl | 3-trifluoromethylphenyl | 480.2 |
| 29 | 4-methylsulfonylphenyl | 3-trifluoromethylphenyl | 512.1 |
| 30 | 4-iodophenyl | 3-trifluoromethylphenyl | 431.0 |
| 31 | 4-aminosulfonylphenyl | 3-trifluoromethylphenyl | 535.1 M + Na |
| 32 | 4-chlorophenyl | 3-trifluoromethylphenyl | 454.1 |
| 33 | 2,4-dimethylphenyl | 3-trifluoromethylphenyl | 448.2 |
| 34 | 4-methylphenyl | 3-trifluoromethylphenyl | 434.1 |
| 35 | 4-chlorophenyl | 3-trifluoromethylphenyl | 482.2 |
| 36 | 4-methylphenyl | 3-trifluoromethylphenyl | 484.2 M + Na |
| 37 | 4-fluorophenyl | 3-trifluoromethylphenyl | 466.2 |
| 38 | phenyl | 3-trifluoromethylphenyl | 448.2 |
| 39 | 4-bromophenyl | 3-trifluoromethylphenyl | 528.1 |
| 40 | 4-phenoxyphenyl | 3-trifluoromethylphenyl | 540.2 |
| 41 | 4-trifluoromethylphenyl | 3-trifluoromethylphenyl | 516.2 |
| 42 | 5-benzotriazolyl | 3-trifluoromethylphenyl | 489.2 |
| 43 | 4-iodophenyl | 3-trifluoromethylphenyl | 574.2 |
| 44 | 4-cyanophenyl | 3-trifluoromethylphenyl | 473.3 |
| 45 | 4-trifluoromethoxyphenyl | 3-trifluoromethylphenyl | 532.2 |
| 46 | 4-formylphenyl | 3-trifluoromethylphenyl | 476.3 |
| 47 | 4-carbomethoxyphenyl | 3-trifluoromethylphenyl | 506.2 |
| 48 | 4-nitrophenyl | 3-trifluoromethylphenyl | 493.2 |
| 49 | 4-aminophenyl | 3-trifluoromethylphenyl | 463.2 |
| 50 | 4-methoxyphenyl | 3-trifluoromethylphenyl | 478.3 |
| 51 | 4-methylthiophenyl | 3-trifluoromethylphenyl | 494.2 |
| 52 | 4-methylsulfonylphenyl | 3-trifluoromethylphenyl | 526.2 |
| 53 | 4-aminosulfonylphenyl | 3-trifluoromethylphenyl | 527.2 |
| 54 | 4-isopropylphenyl | 3-trifluoromethylphenyl | 490.3 |
| 55 | 4-phenylthiophenyl | 3-trifluoromethylphenyl | 556.2 |
| 56 | N,N-diethylsulfamoylphenyl | 3-trifluoromethylphenyl | 583.3 |
| 57 | 4-trifluoromethylthiophenyl | 3-trifluoromethylphenyl | 548.2 |
| 58 | 4-chlorophenyl | 3-trifluoromethylphenyl | 550.1 |
| 59 | 3,4-dimethylphenyl | 3-trifluoromethylphenyl | 420.1 |
| 60 | 4-methylphenyl | 3-trifluoromethylphenyl | 406.1 |
| 61 | 4-aminosulfonylphenyl | 2-amino-5-iodophenyl | 622.2 M + Na |
| 62 | 4-aminosulfonylphenyl | 2-amino-5-chlorophenyl | 530.3 M + Na |
| 63 | 4-aminosulfonylphenyl | 3-chlorophenyl | 515.2 |
| 64 | 4-aminosulfonylphenyl | 3-trifluoromethoxyphenyl | 543.1 |
| 65 | 4-aminosulfonylphenyl | 2-(t-butoxycarbonyl)amino-5-trifluoromethylphenyl | 664.3 M + Na |
| 66 | 4-aminosulfonylphenyl | 2-amino-5-trifluoromethylphenyl | 564.2 M + Na |
| 67 | 4-aminosulfonylphenyl | 2-trifluoromethylphenyl | 564.3 M + Na |
| 68 | 4-aminosulfonylphenyl | 3-chlorophenyl | 530.1 |
| 69 | 4-aminosulfonylphenyl | 2-(ethylcarbonyl)amino-5-iodophenyl | 670.9 M − H |
| 70 | 4-aminosulfonylphenyl | 2-(methylcarbonyl)amino-5-iodophenyl | 656.9 M − H |
| 71 | 4-aminosulfonylphenyl | N-methyl-2-(t-butoxycarbonyl)amino-5-trifluoromethylphenyl | 678.2 M + Na |
| 72 | 4-aminosulfonylphenyl | 2-(ethylcarbonyl)amino-5-trifluoromethylphenyl | 636.1 |
| 73 | 4-aminosulfonylphenyl | 2-(benzylamino)-5-trifluoromethylphenyl | 654.2 M + Na |
| 74 | 4-aminosulfonylphenyl | 2-(ethylamino)-5-trifluoromethylphenyl | 592.1 M + Na |
| 75 | 4-aminosulfonylphenyl | 2-(methylamino)-5-trifluoromethylphenyl | 578.2 M + Na |
| 76 | 4-aminosulfonylphenyl | 2-amino-5-bromophenyl | 554.1 M + H |
| 77 | 4-aminosulfonylphenyl | 2-(t-butoxycarbonyl)amino-5-trifluoromethoxyphenyl | 680.2 M + Na |
| 78 | 4-aminosulfonylphenyl | 2-amino-5-trifluoromethoxyphenyl | 580.1 M + Na |
| 79 | 4-aminosulfonylphenyl | 2-(allylamino)-5-trifluoromethylphenyl | 604.1 M + Na |
| 80 | 4-aminosulfonylphenyl | 2-((2-methyl-2-propenyl)amino)-5-trifluoromethylphenyl | 618.1 M + Na |
| 81 | 4-aminosulfonylphenyl | 2-(cyclopropylmethylene)amino-5-trifluoromethylphenyl | 618.2 M + Na |
| 82 | 4-aminosulfonylphenyl | 2-(butylamino)-5-trifluoromethylphenyl | 620.1 M + Na |
| 83 | 4-aminosulfonylphenyl | 2-(propylamino)-5-trifluoromethylphenyl | 606.2 M + Na |
| 84 | 4-aminosulfonylphenyl | 2-((2-methyl-2-propyl)amino)-5-trifluoromethylphenyl | 620.2 M + Na |
| 85 | 4-aminosulfonylphenyl | 2-(aminocarbonyl)amino-5-iodophenyl | 665.1 M + Na |
| 86 | 4-aminosulfonylphenyl | 2-acetylamino-5-iodophenyl | 642.1 M + H |
| 87 | 4-aminosulfonylphenyl | 2-(methylamino)-5-iodophenyl | 614.1 M + H |
| 88 | 4-aminosulfonylphenyl | 2-(ethylamino)-5-iodophenyl | 628.1 M + H |
| 89 | 4-aminosulfonylphenyl | 2-trifluoroacetylamino-5-iodophenyl | 696.1 M + H |
| 90 | 4-aminosulfonylphenyl | 2-amino-5-nitrophenyl | 519.1 M + H |
| 91 | 4-aminosulfonylphenyl | 2-(iso-propoxycarbonyl)amino-5-iodophenyl | 708.1 M + Na |
| 92 | 4-aminosulfonylphenyl | 2-(tert-butoxycarbonyl)amino-5-iodophenyl | 722.1 M + Na |
| 93 | 4-aminosulfonylphenyl | 2-amino-3,5-dinitrophenyl | 632.0 M + H |
| 94 | 4-aminosulfonylphenyl | 2-(isopropylaminocarbonyl)amino-5-trifluoromethylphenyl | 649.2 M + Na |

TABLE 1-continued

| # | col1 | col2 | mass |
|---|---|---|---|
| 95 | 4-aminosulfonyl phenyl | 2-(cyclohexylcarbonyl)amino-5-trifluoromethylphenyl | 652.2 M + H |
| 96 | 4-aminosulfonyl phenyl | 2-(cyclopentylmethylene-carbonyl)amino-5-trifluoromethylphenyl | 652.2 M + H |
| 97 | 4-methylsulfonyl phenyl | 2-(cyclohexylcarbonyl)amino-5-trifluoromethylphenyl | 651.2 M + H |
| 98 | 4-(methylthio) phenyl | 2-(cyclohexylcarbonyl)amino-5-trifluoromethylphenyl | 619.3 M + H |
| 99 | 4-(methylthio) phenyl | 2-(isopropylaminocarbonyl)amino-5-trifluoromethylphenyl | 594.3 M + H |
| 100 | 4-(methylsulfonyl) phenyl | 2-(isopropylaminocarbonyl)amino-5-trifluoromethylphenyl | 626.2 M + H |
| 101 | 4-aminosulfonyl phenyl | 2-(methylsulfonyl)amino-5-trifluoromethylphenyl | 620.1 M + H |
| 102 | 4-aminosulfonyl phenyl | 2-(aminocarbonyl)amino-5-trifluoromethylphenyl | 585.2 M + H |
| 104 | 4-(methylsulfonyl) phenyl | 2-(allyl)amino-5-trifluoromethylphenyl | 581.3 M + H |
| 105 | 4-(methylthio) phenyl | 2-(allyl)amino-5-trifluoromethylphenyl | 549.3 M + H |
| 106 | 4-(methylsulfonyl) phenyl | 2-(2-methyl-2-propenyl)amino-5-trifluoromethylphenyl | 595.2 M + H |
| 107 | 4-(methylthio) phenyl | 2-(2-methyl-2-propenyl)amino-5-trifluoromethylphenyl | 563.3 M + H |
| 108 | 4-(methylsulfonyl) phenyl | 2-(propyl)amino-5-trifluoromethylphenyl | 583.3 M + H |
| 109 | 4-(methylthio) phenyl | 2-(propyl)amino-5-trifluoromethylphenyl | 551.3 M + H |
| 110 | 4-(methylsulfonyl) phenyl | 2-(2-methylpropyl)amino-5-trifluoromethylphenyl | 597.3 M + H |
| 111 | 4-(methylthio) phenyl | 2-(2-methylpropyl)amino-5-trifluoromethylphenyl | 565.3 M + H |
| 112 | 4-(methylsulfonyl) phenyl | 2-(butyl)amino-5-trifluoromethylphenyl | 597.2 M + H |
| 113 | 4-(methylthio) phenyl | 2-(butyl)amino-5-trifluoromethylphenyl | 565.3 M + H |
| 114 | 4-(methylthio) phenyl | 2-(ethylaminocarbonyl)amino-5-trifluoromethylphenyl | 602.4 M + Na |
| 115 | 4-(methylthio) phenyl | 2-(allylaminocarbonyl)amino-5-trifluoromethylphenyl | 592.3 M + H |
| 117 | 4-(methylthio) phenyl | 2-(iso-butylaminocarbonyl)amino-5-trifluoromethylphenyl | 608.3 M + H |
| 118 | 4-(methylthio) phenyl | 2-(cyclopentylaminocarbonyl)amino-5-trifluoromethylphenyl | 620.3 M + H |
| 119 | 4-(methylthio) phenyl | 2-(tert-butoxycarbonyl)amino-5-trifluoromethylphenyl | 609.3 M + H |
| 120 | 4-(methylthio) phenyl | 2-(iso-propoxycarbonyl)amino-5-trifluoromethylphenyl | 595.3 M + H |
| 121 | 4-(methylthio) phenyl | 2-(Ethoxycarbonyl)amino-5-trifluoromethylphenyl | 581.3 M + H |
| 123 | 4-(methylthio) phenyl | 2-(pyrrolidinylcarbonyl)amino-5-trifluoromethylphenyl | 606.5 M + H |
| 124 | 4-(methylthio) phenyl | 2-(morpholinylcarbonyl)amino-5-trifluoromethylphenyl | 644.6 M + Na |
| 125 | 4-(methylthio) phenyl | 2-(azetidinylcarbonyl)amino-5-trifluoromethylphenyl | 592.5 M + H |
| 127 | 4-(methylthio) phenyl | 2-(pyrrolidinylcarbonyl)amino-5-trifluoromethylphenyl | 594.5 M + H |
| 129 | 4-(methylthio) phenyl | 2-(azetidinylcarbonyl)amino-5-trifluoromethylphenyl | 580.5 M + H |
| 130 | 4-(methoxy)phenyl | 2-(azetidinylcarbonyl)amino-5-trifluoromethylphenyl | 564.4 M + H |
| 131 | 4-(methylthio) phenyl | 2-amino-5-trifluoromethylphenyl | 524.3 M + H |
| 131g | 4-(methylthio) phenyl | 2-(t-butoxycarbonyl)amino-5-trifluoromethylphenyl | 758.1 M + H |
| 132 | 4-(methylthio) phenyl | 3-trifluoromethylphenyl | 509.2 M + H |
| 132a | 4-(methylthio) phenyl | 3-trifluoromethylphenyl | 643.2 M + H |
| 133 | 4-(methylsulfonyl) phenyl | 3-trifluoromethylphenyl | 541.2 M + H |
| 133a | 4-(methylsulfonyl) phenyl | 3-trifluoromethylphenyl | 675.2 M + H |
| 134 | 4-(methylthio) phenyl | 2-amino-5-trifluoromethylphenyl | 566.1 M + H |
| 135 | 4-(methylthio) phenyl | 2-amino-5-trifluoromethylphenyl | 581.0 M + H |
| 136 | 4-(methylthio) phenyl | 3-trifluoromethylphenyl | 509.2 M + H |
| 137 | 4-(methylthio) phenyl | 3-trifluoromethylphenyl | 551.0 M + H |
| 138 | 4-(methylthio) phenyl | 2-amino-5-trifluoromethylphenyl | 524.3 M + H |
| 140 | 4-(methylthio) phenyl | 3-trifluoromethylphenyl | 551.2 M + H |
| 141 | 4-(methylthio) phenyl | 3-trifluoromethylphenyl | 509.1 M + H |
| 144 | 4-(methylthio) phenyl | 2-(iso-propyl)amino-5-trifluoromethylphenyl | 537.2 M + H |
| 145 | 4-(methylthio) phenyl | 2-(i-propylaminocarbonyl)amino-5-trifluoromethylphenyl | 580.1 M + H |
| 146 | 4-(methylthio) phenyl | 2-(morpholinylcarbonyl)amino-5-trifluoromethylphenyl | 608 M + H |
| 151 | 4-(methylthio) phenyl | 2-amino-5-trifluoromethylphenyl | 538.5 M + H |
| 152 | 4-(methylthio) phenyl | 2-amino-5-trifluoromethylphenyl | 538.5 M + H |
| 153 | 4-(methylthio) phenyl | 2-amino-5-trifluoromethylphenyl | 524.4 M + H |
| 154 | 4-chlorophenyl | 3-trifluoromethylphenyl | 469.3 M + H |
| 155 | 4-(methylthio) phenyl | 3-trifluoromethylphenyl | 481.2 M + H |
| 156 | 4-chlorophenyl | 2-amino-5-trifluoromethylphenyl | 484.4 M + H |
| 157 | 4-(methylthio) phenyl | 2-amino-5-trifluoromethylphenyl | 496.5 M + H |
| 158 | 4-(ethylthio)phenyl | 2-amino-5-trifluoromethylphenyl | 510.5 M + H |
| 159 | 4-(methylthio) phenyl | 3-trifluoromethylphenyl | 493.3 M + H |
| 160 | 4-(methylthio) phenyl | 3-trifluoromethylphenyl | 631.3 M + H |
| 161 | 4-(methylthio) phenyl | 2-amino-5-trifluoromethylphenyl | 510.3 M + H |
| 162 | 4-(methylthio) phenyl | 3-trifluoromethylphenyl | 551.4 M + H |
| 163 | 4-(methylthio) phenyl | 2-amino-5-trifluoromethylphenyl | 552.5 M + H |
| 164 | 4-(methylthio) phenyl | 2-(cyclohexyl)amino-5-trifluoromethylphenyl | 620.6 M + H |
| 165 | 4-(methylthio) phenyl | 2-(iso-propyl)amino-5-trifluoromethylphenyl | 580.5 M + H |

TABLE 1-continued

| | | | |
|---|---|---|---|
| 166 | 4-(methylthio)phenyl | 2-(pyrrolidinylcarbonyl)amino-5-trifluoromethylphenyl | 635.6 M + H |
| 167 | 4-(methylthio)phenyl | 2-(methylaminocarbonyl)amino-5-trifluoromethylphenyl | 595.6 M + H |
| 168 | 4-(methylthio)phenyl | 3-amino-5-trifluoromethylphenyl | 538.5 M + H |
| 169 | 4-aminosulfonylphenyl | 3-trifluoromethylphenyl | 528.3 M + H |
| 170 | 4-methylsulfonylphenyl | 3-trifluoromethylphenyl | 527.0 M + H |
| 171 | 4-(methylthio)phenyl | 2-amino-5-trifluoromethylphenyl | 510.3 M + H |
| 172 | 4-(methylthio)phenyl | 3-trifluoromethylphenyl | 509.3 M + H |
| 173 | 4-(methylthio)phenyl | 3-trifluoromethylphenyl | 559.3 M + H |
| 174 | 4-(methylthio)phenyl | 2-amino-5-trifluoromethylphenyl | 566.5 M + H |
| 175 | 4-(methylthio)phenyl | 2-(cyclohexyl)amino-5-trifluoromethylphenyl | 634.6 M + H |
| 176 | 4-(methylthio)phenyl | 2-(iso-propyl)amino-5-trifluoromethylphenyl | 594.4 M + H |
| 177 | 4-(methylthio)phenyl | 3-amino-5-trifluoromethylphenyl | 552.4 M + H |
| 178 | 4-aminosulfonylphenyl | 3-trifluoromethylphenyl | 528.1 M + H |
| 179 | 4-(methylthio)phenyl | 3-trifluoromethylphenyl | 523.4 M + H |
| 180 | 4-(chloro)phenyl | 3-trifluoromethylphenyl | 511.3 M + H |
| 181 | 4-(methoxy)phenyl | 3-trifluoromethylphenyl | 507.4 M + H |
| 182 | 4-(methyl)phenyl | 3-trifluoromethylphenyl | 491.4 M + H |

Table 2 contains additional examples of the present invention. Each of the following structural formulas (A to GG) are to be matched with each $R^1$ and each $R^2$ independently.

TABLE 2

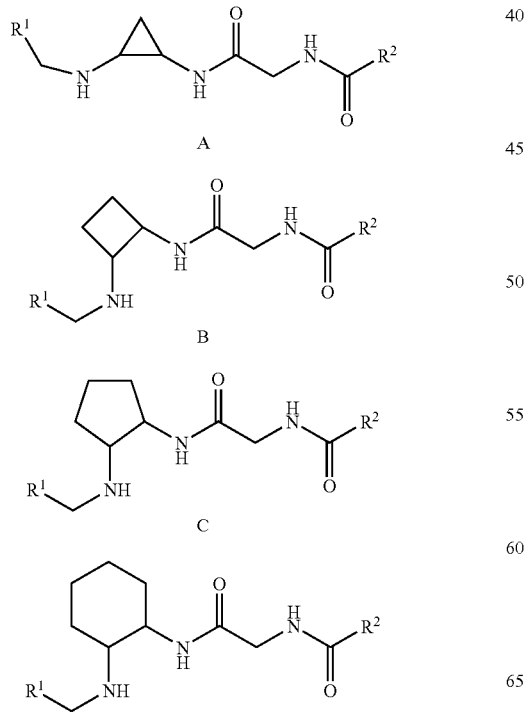

A

B

C

TABLE 2-continued

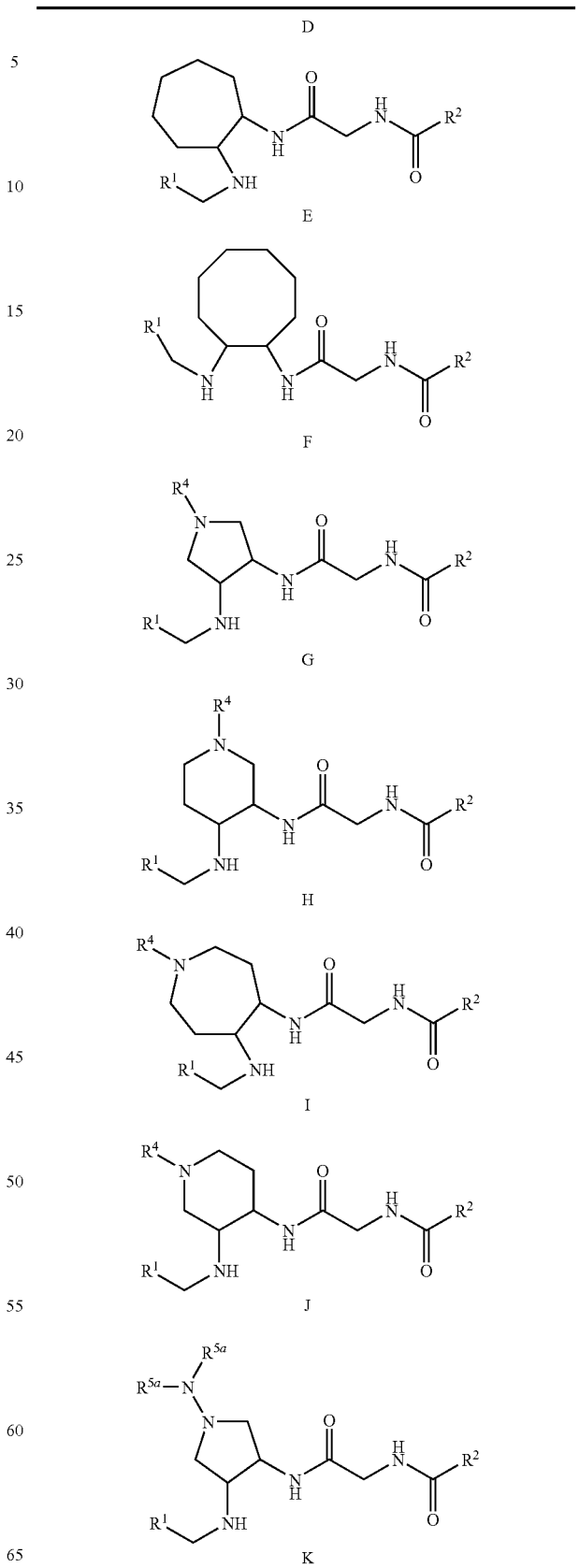

D

E

F

G

H

I

J

K

TABLE 2-continued
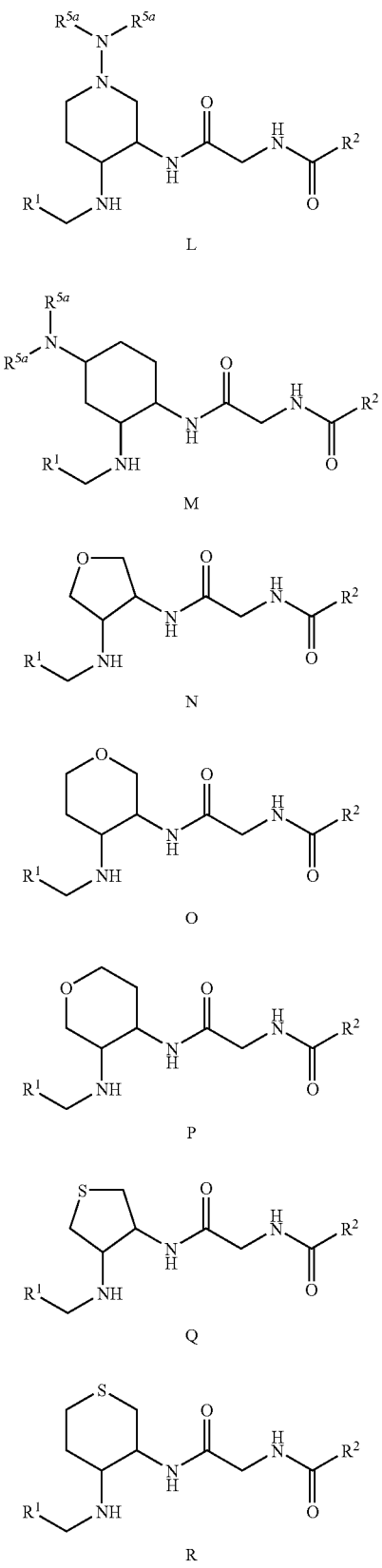
TABLE 2-continued
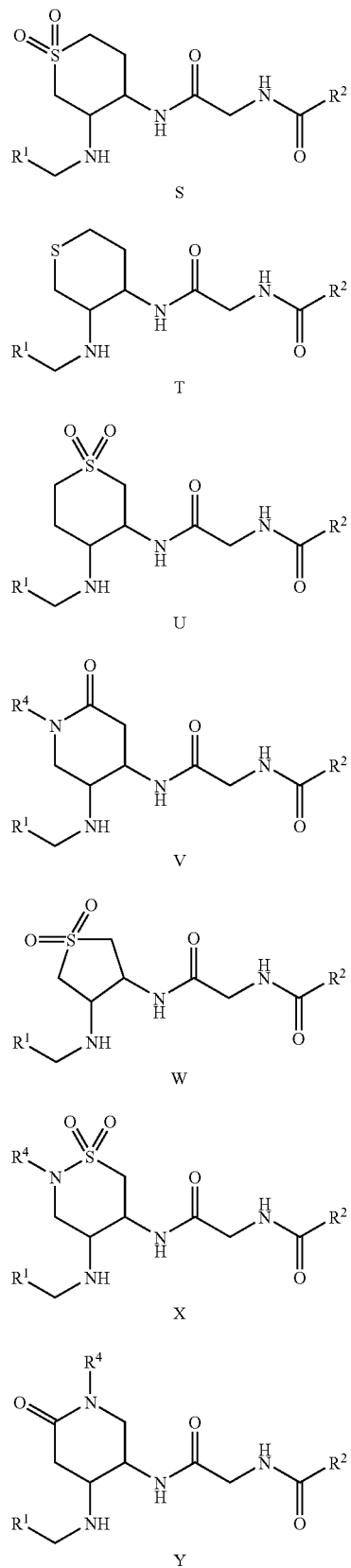

TABLE 2-continued

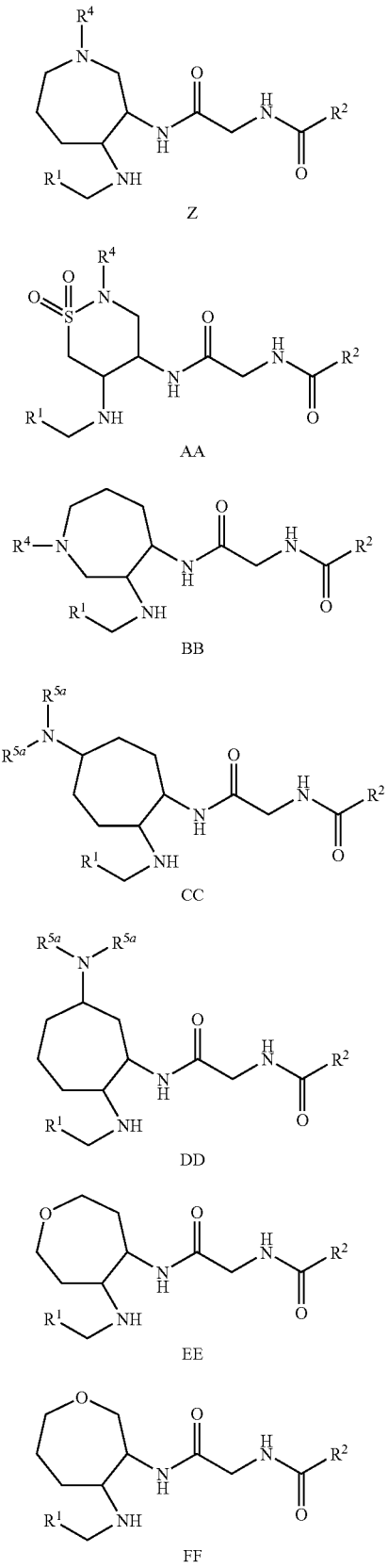

| | R¹ | |
|---|---|---|
| | 1 | 4-chlorophenyl |
| | 2 | 4-bromophenyl |
| | 3 | 4-iodophenyl |
| | 4 | 4-ethenylphenyl |
| | 5 | 4-ethylphenyl |
| | 6 | 4-ethynylphenyl |
| | 7 | 4-isopropylphenyl |
| | 8 | 4-phenoxyphenyl |
| | 9 | 4-trifluoromethylphenyl |
| | 10 | 4-cyanophenyl |
| | 11 | 4-nitrophenyl |
| | 12 | 4-methylphenyl |
| | 13 | 4-methylthiophenyl |
| | 14 | 4-methylsulfonylphenyl |
| | 15 | 4-methoxyphenyl |
| | 16 | 2,4-dimethylphenyl |
| | 17 | 2,4,6-trimethylphenyl |
| | 18 | 3,4-dimethylphenyl |
| | 19 | 4-fluorophenyl |
| | 20 | 1-naphthyl |
| | 21 | 2-naphthyl |
| | 22 | 4-chloro-3-methylphenyl |
| | 23 | 2,4-dichlorophenyl |
| | 24 | 2,5-dimethylphenyl |
| | 25 | 2-chloro-5-trifluoromethylphenyl |
| | 26 | 4-chloro-2-methylphenyl |
| | 27 | 4-chloro-2-fluorophenyl |
| | 28 | 2,4-difluorophenyl |
| | 29 | 2-chloro-4-trifluoromethylphenyl |
| | 30 | 2-fluoro-6-trifluoromethylphenyl |
| | 31 | 2-chloro-5-trifluoromethylphenyl |
| | 32 | 4-fluoro-2-trifluoromethylphenyl |
| | 33 | 4-hydroxyphenyl |
| | 34 | 3-indolyl |
| | 35 | 3,5-dimethyl-4-isoxazole |
| | 36 | 3,5-dimethyl-1-phenyl-4-pyrazolyl |
| | 37 | 3-amino-4-methylphenyl |
| | 38 | 3-amino-4-chlorophenyl |
| | 39 | 3-amino-4-methoxyphenyl |

| | R² | |
|---|---|---|
| | 1 | 3-trifluoromethylphenyl |
| | 2 | 3-bromophenyl |
| | 3 | 3,5-dibromophenyl |
| | 4 | 3-chlorophenyl |
| | 5 | 3-trifluoromethoxyphenyl |
| | 6 | 3-trifluorothiophenyl |
| | 7 | 3-cyanophenyl |
| | 8 | 3-iodophenyl |
| | 9 | 3-formylphenyl |
| | 10 | 3-nitrophenyl |
| | 11 | 5-tert-butyl-2-furanyl |
| | 12 | 3-methylsulfonylphenyl |
| | 13 | 2-amino-5-chlorophenyl |
| | 14 | 2-amino-5-bromophenyl |
| | 15 | 2-amino-5-iodophenyl |
| | 16 | 2-amino-5-trifluoromethylphenyl |
| | 17 | 2-amino-5-fluorophenyl |
| | 18 | 2-amino-5-trifluoromethoxyphenyl |

TABLE 2-continued

| | |
|---|---|
| 19 | 2-amino-5-cyanophenyl |
| 20 | 2-amino-5-formylphenyl |
| 21 | 2-(methylamino)-5-chlorophenyl |
| 22 | 2-(methylamino)-5-bromophenyl |
| 23 | 2-(methylamino)-5-iodophenyl |
| 24 | 2-(methylamino)-5-fluorophenyl |
| 25 | 2-(methylamino)-5-trifluoromethylphenyl |
| 26 | 2-(methylamino)-5-trifluoromethoxyphenyl |
| 27 | 2-(methylamino)-5-cyanophenyl |
| 28 | 2-(ethylamino)-5-chlorophenyl |
| 29 | 2-(ethylamino)-5-bromophenyl |
| 30 | 2-(ethylamino)-5-iodophenyl |
| 31 | 2-(methylamino)-5-fluorophenyl |
| 32 | 2-(ethylamino)-5-trifluoromethylphenyl |
| 33 | 2-(methylamino)-5-trifluoromethoxyphenyl |
| 34 | 2-(ethylamino)-5-cyanophenyl |
| 35 | 2-(aminocarbonyl)amino-5-chlorophenyl |
| 36 | 2-(aminocarbonyl)amino-5-bromophenyl |
| 37 | 2-(aminocarbonyl)amino-5-iodophenyl |
| 38 | 2-(aminocarbonyl)amino-5-fluorophenyl |
| 39 | 2-(aminocarbonyl)amino-5-trifluoromethylphenyl |
| 40 | 2-(aminocarbonyl)amino-5-trifluoromethyloxyphenyl |
| 41 | 2-(aminocarbonyl)amino-5-cyanophenyl |
| 42 | 2-[(methylamino)carbonyl)]amino-5-chlorophenyl |
| 43 | 2-[(methylamino)carbonyl)]amino-5-bromophenyl |
| 44 | 2-[(methylamino)carbonyl)]amino-5-iodophenyl |
| 45 | 2-[(methylamino)carbonyl)]amino-5-fluorophenyl |
| 46 | 2-[(methylamino)carbonyl)]amino-5-trifluoromethylphenyl |
| 47 | 2-[(methylamino)carbonyl)]amino-5-trifluoromethoxyphenyl |
| 48 | 2-[(methylamino)carbonyl)]amino-5-cyanophenyl |

| $R^4$ | |
|---|---|
| 1 | H |
| 2 | methyl |
| 3 | ethyl |
| 4 | propyl |
| 5 | i-propyl |
| 6 | Butyl |
| 7 | i-butyl |
| 8 | t-butyl |
| 9 | Pentyl |
| 10 | Hexyl |
| 11 | C(O)methyl |
| 12 | C(O)H |
| 13 | C(O)methyl |
| 14 | C(O)ethyl |
| 15 | C(O)propyl |
| 16 | C(O)i-propyl |
| 17 | C(O)butyl |
| 18 | C(O)i-butyl |
| 19 | C(O)t-butyl |
| 20 | C(O)pentyl |
| 21 | C(O)cyclopropyl |

| $R^{5a}$ | |
|---|---|
| 1 | H |
| 2 | methyl |
| 3 | ethyl |
| 4 | propyl |
| 5 | i-propyl |
| 6 | Butyl |
| 7 | i-butyl |
| 8 | Pentyl |
| 9 | Hexyl |
| 10 | cyclopropyl |
| 11 | cyclobutyl |

Table 3 contains additional examples of the present invention. Each of the following structural formulas (A to W) are to be matched with each $R^1$ and each $R^2$ independently.

TABLE 3

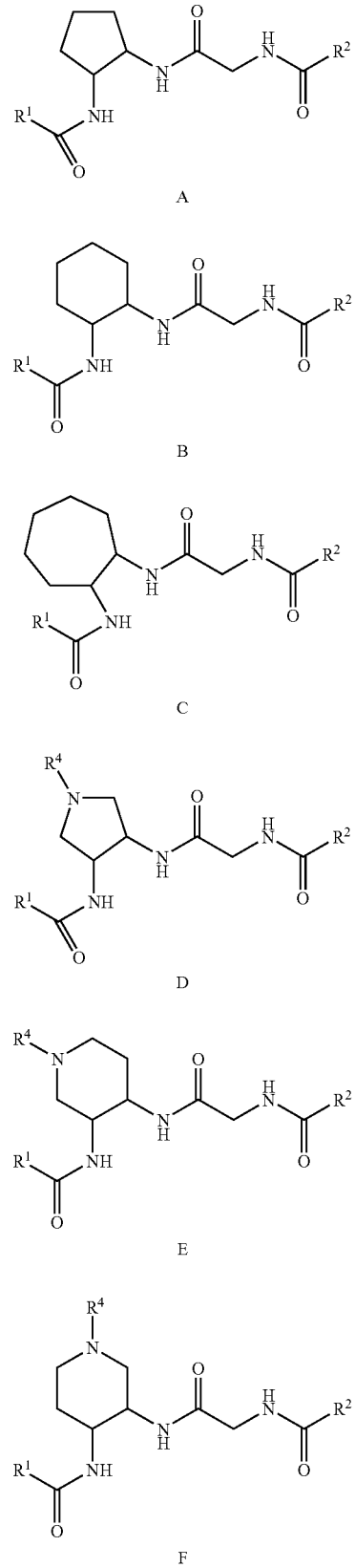

TABLE 3-continued
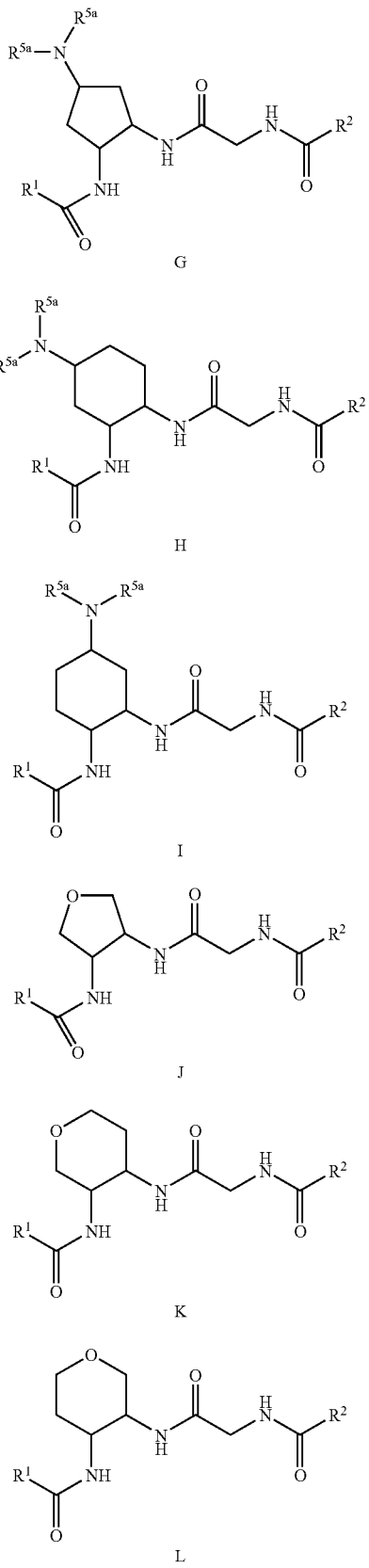
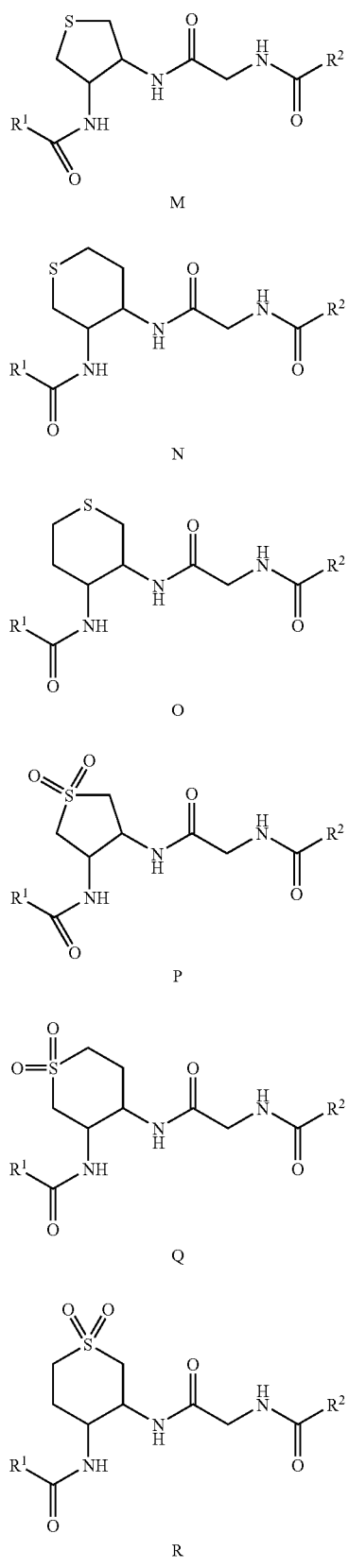

TABLE 3-continued

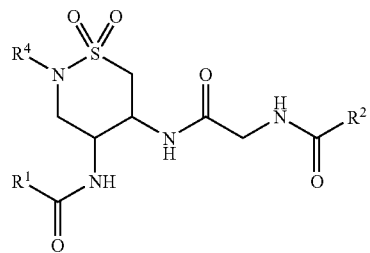

S

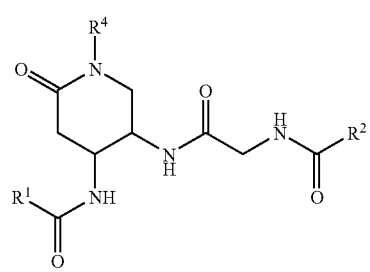

T

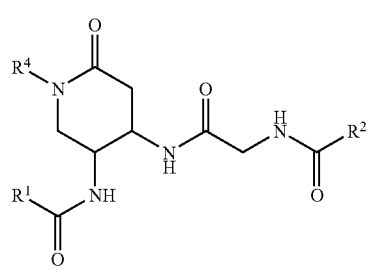

U

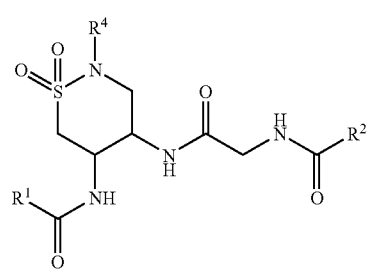

V

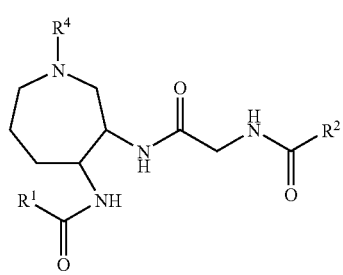

W

TABLE 3-continued

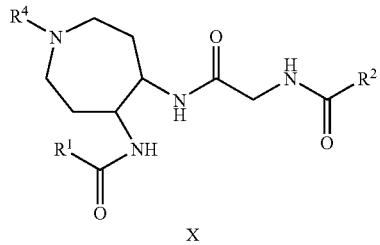

X

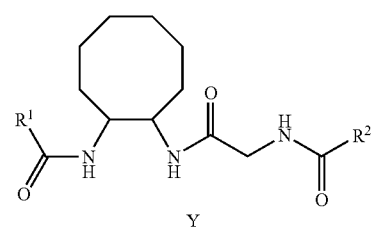

Y

| | R¹ |
|---|---|
| 1 | 4-chlorophenyl |
| 2 | 4-bromophenyl |
| 3 | 4-iodophenyl |
| 4 | 4-ethenylphenyl |
| 5 | 4-ethylphenyl |
| 6 | 4-ethynylphenyl |
| 7 | 4-isopropylphenyl |
| 8 | 4-phenoxyphenyl |
| 9 | 4-trifluoromethylphenyl |
| 10 | 4-cyanophenyl |
| 11 | 4-nitrophenyl |
| 12 | 4-methylphenyl |
| 13 | 4-methylthiophenyl |
| 14 | 4-methylsulfonylphenyl |
| 15 | 4-amninosulfonylphenyl |
| 16 | 4-(methylamino)sulfonylphenyl |
| 17 | 4-(dimethylamino)sulfonylphenyl |
| 18 | 4-formylphenyl |
| 19 | 4-(methoxycarbonyl)phenyl |
| 20 | 4-trifluoromethoxyphenyl |
| 21 | 4-aminophenyl |
| 22 | 4-methylthiophenyl |
| 23 | 4-(aminocarbonyl)phenyl |
| 24 | 4-aminophenyl |
| 25 | phenyl |
| 26 | 4-propylphenyl |
| 27 | 4-difluoromethylphenyl |
| 28 | 4-(phenylthio)phenyl |
| 29 | 4-ethylthiophenyl |
| 30 | 4-ethylsulfonylphenyl |

| | R² |
|---|---|
| 1 | 3-trifluoromethylphenyl |
| 2 | 3-bromophenyl |
| 3 | 3,5-dibromophenyl |
| 4 | 3-chlorophenyl |
| 5 | 3-trifluoromethoxyphenyl |
| 6 | 3-trifluoromethylthiophenyl |
| 7 | 3-cyanophenyl |
| 8 | 3-iodophenyl |
| 9 | 3-formylphenyl |
| 10 | 3-nitrophenyl |
| 11 | 5-tert-butyl-2-furanyl |
| 12 | 3-methylsulfonylphenyl |
| 13 | 2-amino-5-chlorophenyl |
| 14 | 2-amino-5-bromophenyl |
| 15 | 2-amino-5-iodophenyl |
| 16 | 2-amino-5-trifluoromethylphenyl |
| 17 | 2-amino-5-fluorophenyl |
| 18 | 2-amino-5-trifluoromethoxyphenyl |
| 19 | 2-amino-5-cyanophenyl |

TABLE 3-continued

| | |
|---|---|
| 20 | 2-amino-5-formylphenyl |
| 21 | 2-(methylamino)-5-chlorophenyl |
| 22 | 2-(methylamino)-5-bromophenyl |
| 23 | 2-(methylamino)-5-iodophenyl |
| 24 | 2-(methylamino)-5-fluorophenyl |
| 25 | 2-(methylamino)-5-trifluoromethylphenyl |
| 26 | 2-(methylamino)-5-trifluoromethoxyphenyl |
| 27 | 2-(methylamino)-5-cyanophenyl |
| 28 | 2-(ethylamino)-5-chlorophenyl |
| 29 | 2-(ethylamino)-5-bromophenyl |
| 30 | 2-(ethylamino)-5-iodophenyl |
| 31 | 2-(methylamino)-5-fluorophenyl |
| 32 | 2-(ethylamino)-5-trifluoromethylphenyl |
| 33 | 2-(methylamino)-5-trifluoromethoxyphenyl |
| 34 | 2-(ethylamino)-5-cyanophenyl |
| 35 | 2-(aminocarbonyl)amino-5-chlorophenyl |
| 36 | 2-(aminocarbonyl)amino-5-bromophenyl |
| 37 | 2-(aminocarbonyl)amino-5-iodophenyl |
| 38 | 2-(aminocarbonyl)amino-5-fluorophenyl |
| 39 | 2-(aminocarbonyl)amino-5-trifluoromethylphenyl |
| 40 | 2-(aminocarbonyl)amino-5-trifluoromethyloxyphenyl |
| 41 | 2-(aminocarbonyl)amino-5-cyanophenyl |
| 42 | 2-[(methylamino)carbonyl)]amino-5-chlorophenyl |
| 43 | 2-[(methylamino)carbonyl)]amino-5-bromophenyl |
| 44 | 2-[(methylamino)carbonyl)]amino-5-iodophenyl |
| 45 | 2-[(methylamino)carbonyl)]amino-5-fluorophenyl |
| 46 | 2-[(methylamino)carbonyl)]amino-5-trifluoromethylphenyl |
| 47 | 2-[(methylamino)carbonyl)]amino-5-trifluoromethoxyphenyl |
| 48 | 2-[(methylamino)carbonyl)]amino-5-cyanophenyl |

| $R^4$ | |
|---|---|
| 1 | H |
| 2 | methyl |
| 3 | ethyl |
| 4 | propyl |
| 5 | i-propyl |
| 6 | Butyl |
| 7 | i-butyl |
| 8 | t-butyl |
| 9 | Pentyl |
| 10 | Hexyl |
| 11 | C(O)methyl |
| 12 | C(O)H |
| 13 | C(O)methyl |
| 14 | C(O)ethyl |
| 15 | C(O)propyl |
| 16 | C(O)i-propyl |
| 17 | C(O)butyl |
| 18 | C(O)i-butyl |
| 19 | C(O)t-butyl |
| 20 | C(O)pentyl |
| 21 | C(O)cyclopropyl |

Utility

Compounds of formula I are shown to be modulators of chemokine receptor activity using assays know by those skilled in the art. In this section, we describe these assays and give their literature reference. By displaying activity in these assays of MCP-1 antagonism, compounds of formula I are expected to be useful in the treatment of human diseases associated with chemokines and their cognate receptors. The definition of activity in these assays is a compound demonstrating an $IC_{50}$ of 20 μM or lower in concentration when measured in a particular assay.

Antagonism of MCP-1 Binding to Human PBMC (Yoshimura et al., *J. Immunol.* 1990, 145, 292)

Compounds of the present invention have activity in the antagonism of MCP-1 binding to human PBMC (human peripheral blood mononuclear cells) described here.

Millipore filter plates (#MABVN1250) are treated with 100 μl of binding buffer (0.5% bovine serum albumin, 20 mM HEPES buffer and 5 mM magnesium chloride in RPMI 1640 media) for thirty minutes at room temperature. To measure binding, 50 μl of binding buffer, with or without a known concentration compound, is combined with 50 μl of $^{125}$-I labeled human MCP-1 (to give a final concentration of 150 pM radioligand) and 50 μl of binding buffer containing 5×10$^5$ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-Induced Calcium Influx (Sullivan, et al. Methods Mol. Biol., 114, 125-133 (1999)

Compounds of the present invention have activity in the antagonism of MCP-1-induced calcium influx assay described here.

Calcium mobilization is measured using the fluorescent $Ca^{2+}$ indicator dye, Fluo-3. Cells are incubated at 8×10$^5$ cells/ml in phosphate-buffered saline containing 0.1% bovine serum albumin, 20 mM HEPES buffer, 5 mM glucose, 1% fetal bovine serum, 4 μM Fluo-3 AM and 2.5 mM probenecid for 60 minutes at 37° C. Cells used for such calcium assays can include human monocytes isolated as described by Weiner et al., J. Immunol. Methods, 36, 89-97 (1980) or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of 2-4×10$^6$ cells/ml. Cells are plated into 96-well, black-wall microplates (100 μl/well) and the plates centrifuged at 200×g for 5 minutes. Various concentrations of compound are added to the wells (50 μl/well) and after 5 minutes, 50 μl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-induced Human PBMC Chemotaxis (Bacon et al., *Brit. J. Pharmacol.* 1988, 95, 966)

Compounds of the present invention have activity in the antagonism of MCP-1-induced human PBMC chemotaxis assay described here.

Neuroprobe MBA96-96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at $1\times10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 µl to each well and there should be a positive meniscus after dispensing. The 8 micron filter is placed gently on top of the 96 well plate, a rubber gasket is attached to the bottom of the upper chamber, and the chamber is assembled. A 200 µl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy. Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes)

(Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Preferably, the compounds of the present invention are used to treat or prevent disorders selected from rheumatoid arthritis, osteoarthritis, septic shock, atherosclerosis, aneurism, fever, cardiovascular effects, haemodynamic shock, sepsis syndrom, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes melitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

More preferably, the compounds are used to treat or prevent inflammatory disorders selected from from rheumatoid arthritis, osteoarthritis, atherosclerosis, aneurism, fever, cardiovascular effects, Crohn's disease, inflammatory bowel diseases, psoriasis, congestive heart failure, multiple sclerosis, autoimmune diseases, skin inflammatory diseases.

Even more preferably, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a nonsteroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY- 1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels. Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field. Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin. Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit. Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the

The invention claimed is:
1. A compound of Formula (I)

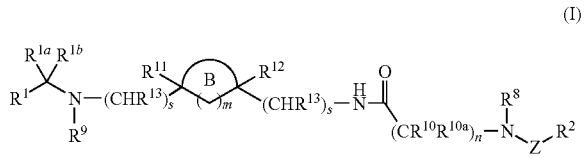

or a stereoisomer or a pharmaceutically acceptable salt thereof, wherein:

ring B is piperidinyl substituted with 0-2 $R^5$ and N-substituted by $R^4$;

Z is selected from a bond, —C(O)—, —C(O)NH—, —C(S)NH—, —SO$_2$—, and —SO$_2$NH—;

$R^{1a}$ and $R^{1b}$ are independently selected from H, $C_{1-4}$ alkyl, $C_{1-4}$ cycloalkyl, $CF_3$, or alternatively, $R^{1a}$ and $R^{1b}$ are taken together to from =O;

$R^1$ is selected from a $C_{6-10}$ aryl group substituted with 0-5 $R^6$ and a 5-10 membered heteroaryl system containing 1-4 heteroatoms selected from N, O, and S, substituted with 0-3 $R^6$;

$R^2$ is selected from a $C_{6-10}$ aryl group substituted with 0-5 $R^7$ and a 5-10 membered heteroaryl system containing 1-4 heteroatoms selected from N, O, and S, substituted with 0-3 $R^7$;

$R^4$ is selected from H, $C_{1-6}$ alkyl, and $(CRR)_rC(O)R^{4b}$;

$R^{4b}$, at each occurrence, is selected from H, $C_{1-6}$ alkyl substituted with 0-3 $R^{4e}$, $C_{3-8}$ alkenyl substituted with 0-3 $R^{4e}$, $C_{3-8}$ alkynyl substituted with 0-3 $R^{4e}$, a $(CH_2)_r$—$C_{3-6}$ carbocyclic residue substituted with 0-2 $R^{4e}$, and a $(CHR)_r$-4-10 membered heterocyclic system containing 1-4 heteroatoms selected from N, O, and S, substituted with 0-2 $R^{4e}$;

$R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, NO$_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, —C(O)$R^{4i}$, —C(O)OR$^{4j}$, —C(O)NR$^{4h}R^{4h}$, —OC(O)NR$^{4h}R^{4h}$, —NR$^{4h}$C(O)NR$^{4h}R^{4h}$, —NR$^{4h}$C(O)OR$^{4j}$, and $(CH_2)_r$phenyl;

$R^{4f}$, at each occurrence, is selected from $C_{1-6}$ alkyl, $C_{3-6}$ cycloalkyl, and phenyl;

$R^{4h}$, at each occurrence, is independently selected from H, $C_{1-6}$ alkyl, $C_{3-8}$ alkenyl, $C_{3-8}$ alkynyl, and a $(CH_2)_r$—$C_{3-10}$ carbocyclic;

$R^{4i}$, at each occurrence, is selected from H, $C_{1-6}$ alkyl, $C_{3-8}$ alkenyl, $C_{3-8}$ alkynyl, and a $(CH_2)_r$—$C_{3-6}$ carbocyclic residue;

$R^{4j}$, at each occurrence, is selected from $CF_3$, $C_{1-6}$ alkyl, $C_{3-8}$ alkenyl, $C_{3-8}$ alkynyl, and a $C_{3-10}$ carbocyclic residue;

$R^5$, at each occurrence, is independently selected from H, $C_{1-6}$ alkyl, $C_{2-8}$ alkenyl, $C_{2-8}$ alkynyl, $(CRR)_rOH$, $(CRR)_rSH$, $(CRR)_rOR^{5d}$, $(CRR)_rSR^{5d}$, $(CRR)_rNR^{5a}R^{5a}$, $(CRR)_rC(O)OH$, $(CRR)_rC(O)R^{5b}$, $(CRR)_rC(O)NR^{5a}R^{5a}$, $(CRR)_rNR^{5a}C(O)R^{5b}$, $(CRR)_rOC(O)NR^{5a}R^{5a}$, $(CRR)_rNR^{5a}C(O)OR^{5d}$, $(CRR)_rNR^{5a}C(O)NR^{5a}R^{5a}$, $(CRR)_rNR^{5a}C(O)H$, $(CRR)_rC(O)OR^{5b}$, $(CRR)_rOC(O)R^{5b}$, $(CRR)_rS(O)_pR^{5b}$, $(CRR)_rS(O)_2$NR^{5a}R^{5a}$, $(CRR)_rNR^{5a}S(O)_2R^{5b}$, $(CRR)_rNR^{5a}S(O)_2NR^{5a}R^{5a}$, $C_{1-6}$ haloalkyl, a $(CRR)_r$—$C_{3-10}$ carbocyclic residue substituted with 0-3 $R^{5c}$, and a $(CRR)_r$-5-10 membered heterocyclic system containing 1-4 heteroatoms selected from N, O, and S, substituted with 0-2 $R^{5c}$;

$R^{5a}$, at each occurrence, is independently selected from H, methyl substituted with 0-1 $R^{5g}$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^{5e}$, a $(CH_2)_r$—$C_{3-10}$ carbocyclic residue substituted with 0-5 $R^{5e}$, and a $(CH_2)_r$-5-10 membered heterocyclic system containing 1-4 heteroatoms selected from N, O, and S, substituted with 0-3 $R^{5e}$;

$R^{5b}$, at each occurrence, is selected from $C_{1-6}$ alkyl substituted with 0-3 $R^{5e}$, $C_{3-8}$ alkenyl substituted with 0-2 $R^{5e}$, $C_{3-8}$ alkynyl substituted with 0-2 $R^{5e}$, a $(CH_2)_r$—$C_{3-6}$ carbocyclic residue substituted with 0-2 $R^{5e}$, and a $(CH_2)_r$-5-6 membered heterocyclic system containing 1-4 heteroatoms selected from N, O, and S, substituted with 0-3 $R^{5e}$;

$R^{5c}$, at each occurrence, is selected from $C_{-1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{5f}R^{5f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{5b}$, $(CH_2)_rC(O)NR^{5f}R^{5f}$, $(CH_2)_rNR^{5f}C(O)R^{5b}$, $(CH_2)_rC(O)OC_{1-4}$ alkyl, $(CH_2)_rOC(O)R^{5b}$, $(CH_2)_rC(=NR^{5f})NR^{5f}R^{5f}$, $(CH_2)_rS(O)_pR^{5b}$, $(CH_2)_rNHC(=NR^{5f})NR^{5f}R^{5f}$, $(CH_2)_rS(O)_2NR^{5f}R^{5f}$, $(CH_2)_rNR^{5f}S(O)_2R^{5b}$, and $(CH_2)_r$phenyl substituted with 0-3 $R^{5e}$;

$R^{5d}$, at each occurrence, is selected from methyl, $CF_3$, $C_{2-6}$ alkyl substituted with 0-2 $R^{5e}$, $C_{3-8}$ alkenyl substituted with 0-2 $R^{5e}$, $C_{3-8}$ alkynyl substituted with 0-2 $R^e$, and a $C_{3-10}$ carbocyclic residue substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkcyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, and $(CH_2)_r$phenyl;

$R^{5f}$, at each occurrence, is selected from H, $C_{1-6}$ alkyl, and $C_{3-6}$ cycloalkyl;

$R^{5g}$ is independently selected from —C(O)$R^{5b}$, —C(O)OR$^{5d}$, —C(O)NR$^{5f}R^{5f}$ and $(CH_2)_r$phenyl;

R, at each occurrence, is selected from H, $C_{1-6}$ alkyl substituted with $R^{5e}$, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, at each occurrence, is selected from $C_{1-8}$ alkyl, $C_{2-8}$ alkenyl, $(CH_2)_rC_{3-6}$ cycloalkyl, Cl, Br, I, F, $NO_2$, CN, (CR'R')$_rNR^{6a}R^{6a}$, (CR'R')$_rOH$, (CR'R')$_rO$(CR'R')$_rR^{6d}$, (CR'R')$_rSH$, (CR'R')$_rC(O)H$, (CR'R')$_rS$(CR'R')$_rR^{6d}$, (CR'R')$_rSC(O)(CR'R')$_rR^{6b}$, (CR'R')$_rC(O)OH$, (CR'R')$_rC(O)(CR'R')$_rR^{6b}$, (CR'R')$_rNR^{6a}R^{6a}$, (CR'R')$_rC(O)NR^{6a}R^{6a}$, (CR'R')$_rNR^{6f}C(O)(CR'R')$_rR^{6b}$, (CR'R')$_rC(O)O(CR'R')$_rR^{6d}$, (CR'R')$_rOC(O)(CR'R')$_rR^{6b}$, (CR'R')$_rOC(O)NR^{6a}(CR'R')$_rR^{6d}$, (CR'R')$_rNR^{6a}C(O)NR^{6a}(CR'R')$_rR^{6d}$, (CR'R')$_rNR^{6a}C(S)NR^{6a}(CR'R')$_rR^{6d}$, (CR'R')$_rNR^{6f}C(O)O(CR'R')$_rR^{6b}$, (CR'R')$_rC(=NR^{6f})NR^{6a}R^{6a}$, (CR'R')$_rNHC(=NR^{6f})NR^{6f}R^{6f}$, (CR'R')$_rS(O)_p(CR'R')$_rR^{6b}$, (CR'R')$_rS(O)_2NR^{6a}R^{6a}$, (CR'R')$_rNR^{6f}S(O)_2NR^{6a}R^{6a}$, (CR'R')$_rNR^{6f}S(O)_2(CR'R')$_rR^{6b}$, $C_{1-6}$ haloalkyl, $C_{2-8}$ alkenyl substituted with 0-3 R', $C_{2-8}$ alkynyl substituted with 0-3 R', and (CR'R')$_r$phenyl substituted with 0-3 $R^{6e}$;

alternatively, two $R^6$ on adjacent atoms on $R^1$ may join to form a cyclic acetal;

$R^{6a}$, at each occurrence, is selected from H, methyl substituted with 0-1 $R^{6g}$, $C_{2-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CH_2)_r$—$C_{3-10}$ carbocyclic residue substituted with 0-5 $R^{6e}$, and a $(CH_2)_r$-5-10 membered heterocyclic system containing 1-4 heteroatoms selected from N, O, and S, substituted with 0-2 $R^{6e}$;

R$^{6b}$, at each occurrence, is selected from H, C$_{1-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CH$_2$)$_r$—C$_{3-6}$ carbocyclic residue substituted with 0-3 R$^{6e}$, and a (CH$_2$)$_r$-5-6 membered heterocyclic system containing 1-4 heteroatoms selected from N, O, and S, substituted with 0-2 R$^{6e}$;

R$^{6d}$, at each occurrence, is selected from C$_{3-8}$ alkenyl substituted with 0-2 R$^{6e}$, C$_{3-8}$ alkynyl substituted with 0-2 R$^{6e}$, methyl, CF$_3$, C$_{2-6}$ alkyl substituted with 0-3 R$^{6e}$, a (CH$_2$)$_r$—C$_{3-10}$ carbocyclic residue substituted with 0-3 R$^{6e}$, and a (CH$_2$)$_r$-5-6 membered heterocyclic system containing 1-4 heteroatoms selected from N, O, and S, substituted with 0-3 R$^{6e}$;

R$^{6e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is selected from H, C$_{1-5}$ alkyl, and C$_{3-6}$ cycloalkyl, and phenyl;

R$^{6g}$ is independently selected from —C(O)R$^{6b}$, —C(O)OR$^{6d}$, —C(O)NR$^{6f}$R$^{6f}$, and (CH$_2$)$_r$phenyl;

R$^7$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O(CR'R')$_r$R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O)(CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$C(O)O(CR'R')$_r$R$^{7d}$, (CR'R')$_r$OC(O)(CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7b}$, (CR'R')$_r$C(=NR$^{7f}$)NR$^{7a}$R$^{7a}$, (CR'R')$_r$NHC(=NR$^{7f}$)NR$^{7f}$R$^{7f}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$R$^{7b}$, C$_{1-6}$ haloalkyl, C$_{2-8}$ alkenyl substituted with 0-3 R', C$_{2-8}$ alkynyl substituted with 0-3 R', and (CR'R')$_r$phenyl substituted with 0-3 R$^{7e}$;

alternatively, two R$^7$ on adjacent atoms on R$^2$ may join to form a cyclic acetal;

R$^{7a}$, at each occurrence, is independently selected from H, methyl substituted with 0-1 R$^{7g}$, C$_{2-6}$ alkyl substituted with 0-2 R$^{7e}$, C$_{3-8}$ alkenyl substituted with 0-2 R$^{7e}$, C$_{3-8}$ alkynyl substituted with 0-2 R$^{7e}$, a (CH$_2$)$_r$—C$_{3-10}$ carbocyclic residue substituted with 0-5 R$^{7e}$, and a (CH$_2$)$_r$-5-10 membered heterocyclic system containing 1-4 heteroatoms selected from N, O, and S, substituted with 0-2 R$^{7e}$;

R$^{7b}$, at each occurrence, is selected from C$_{1-6}$ alkyl substituted with 0-2 R$^{7e}$, C$_{3-8}$ alkenyl substituted with 0-2 R$^{7e}$, C$_{3-8}$ alkynyl substituted with 0-2 R$^{7e}$, a (CH$_2$)$_r$C$_{3-6}$ carbocyclic residue substituted with 0-3 R$^{7e}$, and a (CH$_2$)$_r$-5-6 membered heterocyclic system containing 1-4 heteroatoms selected from N, O, and S, substituted with 0-2 R$^{7e}$;

R$^{7d}$, at each occurrence, is selected from C$_{3-8}$ alkenyl substituted with 0-2 R$^{7e}$, C$_{3-8}$ alkynyl substituted with 0-2 R$^{7e}$, methyl, CF$_3$, C$_{2-6}$ alkyl substituted with 0-3 R$^{7e}$, a (CH$_2$)$_r$—C$_{3-10}$ carbocyclic residue substituted with 0-3 R$^{7e}$, and a (CH$_2$)$_r$-5-6 membered heterocyclic system containing 1-4 heteroatoms selected from N, O, and S, substituted with 0-3 R$^{7e}$;

R$^{7e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, C$_{1-5}$ alkyl, and C$_{3-6}$ cycloalkyl, and phenyl;

R$^{7g}$ is independently selected from —C(O)R$^{7b}$, —C(O)OR$^{7d}$, —C(O)NR$^{7f}$R$^{7f}$, and (CH$_2$)$_r$phenyl;

R', at each occurrence, is selected from H, C$_{1-6}$ alkyl substituted with R$^{6e}$, C$_{2-8}$ alkenyl, C$_{2-8}$ alkynyl, (CH$_2$)$_r$C$_{3-6}$ cycloalkyl, and (CH$_2$)$_r$phenyl substituted with R$^{6e}$;

R$^8$ is selected from H, C$_{1-4}$ alkyl, and C$_{3-4}$ cycloalkyl;

R$^9$ is selected from, H, C$_{1-4}$ alkyl, C$_{3-4}$ cycloalkyl, and (CH$_2$)—R$^1$;

R$^{10}$ and R$^{10a}$ are each H,

R$^{11}$ is H,

R$^{12}$ is H, n is 1;

m is 0;

p, at each occurrence, is independently selected from 0, 1, and 2;

q, at each occurrence, is independently selected from 1, 2, 3, and 4;

r, at each occurrence, is independently selected from 0, 1, 2, 3, and 4;

s, at each occurrence, is 0; and t, at each occurrence, is independently selected from 2, 3, and 4.

2. The compound of claim 1, wherein:
ring B is selected from

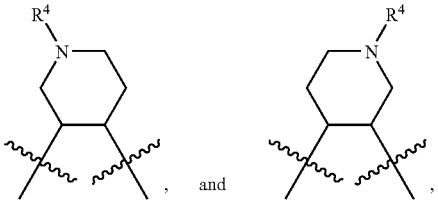

ring B being optionally substituted with 0-1 R$^5$.

3. The compound of claim 2, wherein:
R$^5$, at each occurrence, is independently selected from H, C$_{1-6}$ alkyl, C$_{2-8}$ alkenyl, C$_{2-8}$ alkynyl, (CRR)$_r$OH, (CRR)$_r$SH, (CRR)$_r$OR$^{5d}$, (CRR)$_r$SR$^{5d}$, (CRR)$_r$NR$^{5a}$R$^{5a}$, (CRR)$_r$C(O)OH, (CRR)$_r$C(O)R$^{5b}$, (CRR)$_r$C(O)NR$^{5a}$R$^{5a}$, (CRR)$_r$NR$^{5a}$C(O)R$^{5b}$, (CRR)$_r$NR$^{5a}$C(O)OR$^{5d}$, (CRR)$_r$OC(O)NR$^{5a}$R$^{5a}$, (CHR)$_r$NR$^{5a}$C(O)NR$^{5a}$R$^{5a}$, CRR(CRR)$_r$NR$^{5a}$C(O)H, (CRR)$_r$C(O)OR$^{5b}$, (CRR)$_r$OC(O)R$^{5b}$, (CRR)$_r$S(O)$_p$R$^{5b}$, (CRR)$_r$S(O)$_2$NR$^{5a}$R$^{5a}$, (CRR)$_r$NR$^{5a}$S(O)$_2$R$^{5b}$, and C$_{1-6}$ haloalkyl;

R$^{5a}$, at each occurrence, is independently selected from H, methyl, C$_{1-6}$ alkyl substituted with 0-2 R$^{5e}$ wherein the alkyl is selected from ethyl, propyl, i-propyl, butyl, i-butyl, pentyl, hexyl, C$_3$ alkenyl substituted with 0-1 R$^{5e}$, wherein the alkenyl is selected from allyl, C$_3$ alkynyl substituted with 0-1 R$^{5e}$ wherein the alkynyl is selected from propynyl, and a (CH$_2$)$_r$—C$_{3-4}$ carbocyclic residue substituted with 0-5 R$^{5e}$, wherein the carbocyclic residue is selected from cyclopropyl, and cyclobutyl;

R$^{5b}$, at each occurrence, is selected from C$_{1-6}$ alkyl substituted with 0-2 R$^{5e}$, wherein the alkyl is selected from methyl, ethyl, propyl, i-propyl, butyl, i-butyl, pentyl, and hexyl, a (CH$_2$)$_r$—C$_{3-4}$ carbocyclic residue substituted with 0-2 R$^{5e}$, wherein the carbocyclic residue is selected from cyclopropyl, and cyclobutyl; and R$^{5d}$, at each occurrence, is selected from methyl, CF$_3$, C$_{2-6}$ alkyl substituted with 0-2 R$^{5e}$, wherein the alkyl is selected from methyl, ethyl, propyl, i-propyl, butyl, i-butyl, pentyl, and hexyl, $C_{3-8}$ alkenyl, $C_{3-8}$ alkynyl, and a $C_{3-10}$ carbocyclic residue substituted with 0-3 $R^{5e}$.

4. The compound of claim 3, wherein:

R, at each occurrence, is independently selected from H, methyl, ethyl, propyl, allyl, propynyl, $(CH_2)_rC_{3-6}$ cycloalkyl, and $(CH_2)_r$phenyl substituted with $R^{6e}$;

$R^5$, at each occurrence, is independently selected from H, methyl, ethyl, propyl, i-propyl, butyl, i-butyl, allyl, propynyl, $(CH_2)_r$OH, $(CH_2)_r$OR$^{5d}$, $(CH_2)_r$NR$^{5a}$R$^{5a}$, $(CH_2)_r$C(O)OH, $(CH_2)_r$C(O)R$^{5b}$, $(CH_2)_r$C(O)NR$^{5a}$R$^{5a}$, $(CH_2)_r$NR$^{5a}$C(O)R$^{5b}$, $(CH_2)_r$OC(O)NR$^{5a}$R$^{5a}$, $(CH_2)_r$NR$^{5a}$C(O)OR$^{5d}$, $(CH_2)_r$NR$^{5a}$C(O)R$^{5b}$, $(CH_2)_r$C(O)OR$^{5b}$, $(CH_2)_r$OC(O)R$^{5b}$, $(CH_2)_r$NR$^{5a}$S(O)$_2$R$^{5b}$, and $C_{1-6}$ haloalkyl;

$R^{5a}$, at each occurrence, is independently selected from H, methyl, ethyl, propyl, i-propyl, butyl, i-butyl, pentyl, hexyl, cyclopropyl, and cyclobutyl; and r, at each occurrence, is selected from 0, 1, and 2.

5. The compound of claim 4, wherein:

$R^1$ is selected from phenyl substituted with 0-2 $R^6$, naphthyl substituted with 0-2$R^6$, and a 5-10 membered heteroaryl system containing 1-4 heteroatoms selected from N, O, and S, substituted with 0-3 $R^6$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

$R^2$ is selected from phenyl substituted with 0-2 $R^7$, and a 5-10 membered heteroaryl system containing 1-4 heteroatoms selected from N, O, and S, substituted with 0-3 $R^7$ wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl;

$R^4$ is selected from H, methyl, ethyl, propyl, i-propyl, butyl, i-butyl, $(CRR)_rOR^{4d}$;

$R^{4a}$, at each occurrence, is independently selected from H, methyl substituted with 0-1 $R^{4c}$, $C_{2-6}$ alkyl substituted with 0-3 $R^{4e}$ wherein $C_{2-6}$ is selected from ethyl, propyl, i-propyl, butyl, i-butyl, t-butyl, pentyl and hexyl, and a $(CH_2)_r$—$C_{3-6}$ carbocyclic residue substituted with 0-4 $R^{4e}$ wherein the carbocyclic residue is selected from cyclopropyl, cyclohexyl, and phenyl;

$R^{4d}$ is selected from methyl, ethyl, propyl, i-propyl, butyl, i-butyl, t-butyl, pentyl, and cyclopropyl;

$R^8$ is selected from H, methyl, ethyl, propyl, i-propyl, and cyclopropyl; and $R^9$ is selected from H, methyl, ethyl, propyl, i-propyl, and cyclopropyl, and $CH_2$—$R^1$.

6. The compound of claim 5, wherein:

$R^6$, at each occurrence, is selected from $C_{1-8}$ alkyl, $C_{2-8}$ alkenyl, $C_{2-8}$ alkynyl, $(CRR)_rC_{3-6}$ cycloalkyl, Cl, Br, I, F, NO$_2$, CN, $(CRR)_rNR^{6a}R^{6a}$, $(CRR)_rOH, (CRR)_rO(CRR)_rR^{6d}$, $(CRR)_rSH, (CRR)_rC(O)H, (CRR)_rS(CRR)_rR^{6d}, (CRR)_rC(O)OH, (CRR)_rC(O)(CRR)_rR^{6b}, (CRR)_rC(O)NR^{6a}R^{6a}, (CRR)_rNR^{6f}C(O)(CRR)_rR^{6b}, (CRR)_rNR^{6a}C(O)NR^{6a}R^{6a}, (CRR_(rC(O)O(CRR)_rR^{6d}, (CRR)_rNR^{6a}C(O)NR^{6a}R^{6a}, (CRR)_rNR^{6a}C(S)NR^{6a}R^{6a}, (CRR)_rOC(O)(CRR)_rR^{6b}, (CRR)_r S(O)_p(CRR)_rR^{6b}, (CRR)_rS(O)_2NR^{6a}R^{6a}, (CRR)_r NR^{6f}S(O)_2(CRR)_rR^{6b}, (CRR)_rNR^{6f}S(O)_2 NR^{6a}R^{6a}, C_{1-6}$ haloalkyl, and $(CRR)_r$phenyl substituted with 0-3 $R^{6e}$;

$R^{6a}$, at each occurrence, is independently selected from H, methyl, ethyl, propyl, i-propyl, butyl, i-butyl, t-butyl, pentyl, hexyl, cyclopropyl and phenyl;

$R^{6b}$, at each occurrence, is selected from methyl, ethyl, propyl, i-propyl, butyl, i-butyl, t-butyl, pentyl, hexyl, cyclopropyl, and phenyl;

$R^{6d}$, at each occurrence, is selected from methyl, CF$_3$, ethyl, propyl, i-propyl, butyl, i-butyl, t-butyl, pentyl, hexyl, cyclopropyl, and phenyl;

$R^{6e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, NO$_2$, $(CF_2)_rCF_3$, $(CH_2)_rOC_{1-5}$ alkyl, OH, SH, $(CH_2)_rSC_{1-5}$ alkyl, $(CH_2)_rNR^{6f}R^{6f}$, and $(CH_2)_r$phenyl;

$R^{6f}$, at each occurrence is selected from H, methyl, ethyl, propyl, i-propyl, butyl, i-butyl, t-butyl, pentyl, hexyl, cyclopropyl, and phenyl;

$R^7$ is selected from methyl, ethyl, propyl, i-propyl, butyl, i-butyl, s- butyl, t-butyl, pentyl, hexyl, $(CRR)_rC_{3-6}$ cycloalkyl, Cl, Br, I, F, NO$_2$, CN, $(CRR)_rNR^{7a}R^{7a}$, $(CRR)_rOH, (CRR)_rO(CH)_rR^{7d}, (CRR)_rSH, (CRR)_rC(O)H, (CRR)_rS(CRR)_rR^{7d}, (CRR)_rC(O)OH, (CRR)_rC(O)(CRR)_rR^{7b}, (CRR)_rC(O)NR^{7a}R^{7a}, (CRR)_rNR^{7f}C(O)(CRR)_rR^{7b}, (CRR)_rC(O)O(CRR)_rR^{7d}, (CRR)_rOC(O)(CRR)_rR^{7b}, (CRR)_rNR^{7a}C(O)NR^{7a}R^{7a}, (CRR)_r NR^{7a}C(O)O(CRR)_rR^{7d}, (CRR)_rS(O)_p(CRR)_rR^{7b}, (CRR)_rS(O)_2NR^{7a}R^{7a}, (CRR)_rNR^{7f}S(O)_2(CRR)_rR^{7b}, C_{1-6}$ haloalkyl, and $(CRR)_r$phenyl substituted with 0-3 $R^{7e}$;

$R^{7a}$, at each occurrence, is selected from H, methyl, ethyl, propyl, i-propyl, butyl, i-butyl, t-butyl, pentyl, hexyl,, prop-2-enyl, 2-methyl-2-propenyl, cyclopropyl, cyclobutyl, cyclopentyl, cyclohexyl, CH$_2$cyclopropyl, and benzyl;

$R^{7b}$, at each occurrence, is selected from methyl, ethyl, propyl, i-propyl, butyl, i-butyl, t-butyl, pentyl, hexyl, cyclopropyl, cyclopentyl, CH$_2$-cyclopentyl, cyclohexyl, CH$_2$-cyclohexyl, CF$_3$, pyrrolidinyl, morpholinyl, and azetidinyl;

$R^{7d}$, at each occurrence, is selected from methyl, CF$_3$, ethyl, propyl, i-propyl, butyl, i-butyl, t-butyl, pentyl, hexyl, and cyclopropyl;

$R^{7e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, NO$_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is selected from H, methyl, ethyl, propyl, i-propyl, butyl, i-butyl, t-butyl, pentyl, hexyl, cyclopropyl, and phenyl; and r is 0 or 1.

7. The compound of claim 6, wherein $R^7$ is selected from methyl, ethyl, propyl, i-propyl, butyl, i-butyl, s-butyl, pentyl, hexyl, Cl, Br, I, F, NO$_2$, NR$^{7a}$R$^{7a}$, NHC(O)NHR$^{7a}$, NR$^{7a}$C(O)R$^{7b}$, NR$^{7a}$C(O)OR$^{7d}$, CF$_3$, OCF$_3$, C(O)R$^{7b}$, NR$^{7f}$C(O)NR$^{7a}$R$^{7a}$, NHS(O)$_2$R$^{7b}$,

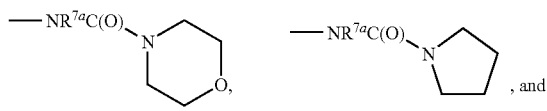

-continued

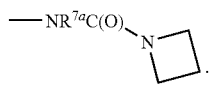

8. The compound of claim 7, wherein in text ring B is selected from

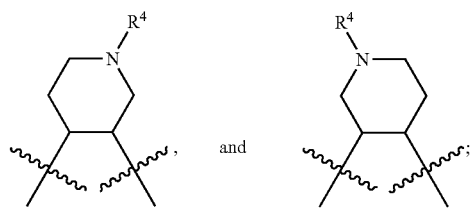

Z is —C(O)—;
$R^{1a}$ and $R^{1b}$ are selected from H and methyl, or alternatively, $R^{1a}$ and $R^{1b}$ are taken together to form =O;
$R^1$ is selected from a $C_{6-10}$ aryl group substituted with 0-3 $R^6$ wherein the aryl group is selected from phenyl and naphthyl, and a 5-10 membered heteroaryl system containing 1-4 heteroatoms selected from N and O, substituted with 0-3 $R^6$ wherein the heteroaryl system is selected from furyl, indolyl, and benzotriazolyl;
$R^2$ is phenyl substituted with 0-1 $R^7$;
$R^4$ is selected from H, methyl, ethyl, propyl, i-propyl, butyl, I-butyl, t-butyl, pentyl, hexyl, and $(CH_2)_rC(O)R^{4b}$;
$R^6$ is selected from methyl, ethyl, propyl, i-propyl, butyl, F, Cl, Br, I, $NO_2$, CN, O $(CH_2)_rR^{6d}$, C(O)H, $SR^{6d}$, $NR^{6a}R^{6a}$, $OC(O)R^{6b}$, $S(O)_pR^{6b}$, $(CHR')_rS(O)_2NR^{6a}R^{6a}$, $CF_3$;
$R^{6a}$ is H methyl, or ethyl;
$R^{6b}$ is H or methyl;
$R^{6d}$ is methyl, phenyl, $CF_3$, and $(CH_2)$-phenyl;
$R^9$ is selected from H, methyl, and $(CH_2)$—$R^1$; and
r is 0 or 1.

9. The compound of claim 1, wherein the compound is selected from:
2-amino-N-{2-[((3S,4R)-{[4-(methylthio)benzyl]amino}-1-propyl-3-piperidinyl)aminol]-2-oxoethyl}-5-(trifluoromethyl)benzamide;
2-Amino-N-{2-[((3R,4S)-4-{[4-(methylthio)benzyl]amino}-1-propyl-3-piperidinyl)amino]-2-oxoethyl}-5-(trifluoromethyl)benzamide;
2-amino-N-{2-[((cis)-4-{[4-(methylthio)benzoyl]amino}-1-methyl-3-piperidinyl)amino]-2-oxoethyl}-5-(trifluoromethyl)benzamide;
N-{2-[((cis)-4-{[4-chlorobenzyl]amino}-3-piperidinyl)amino]-2-oxoethy}-3-(trifluoromethyl)benzamide;
N-{2-[((cis)-4-{[4-(methythio)benzyl]amino}-3-piperidinyl)amino]-2-oxoethyl}-3-(trifluoromethyl)benzamide;
2-Amino-N-{2-[((cis)-4-{[4-chlorobenzyl]amino}-3-piperidinyl)amino]-2-oxoethyl}-5-(trifluoromethyl)benzamide;
2-Amino-N-{2-[((cis)-4-{[4-methylthiobenzyl]amino}-3-piperidinyl)amino]-2-oxoethyl}-5-(trifluoromethyl)benzamide;
2-Amino-N-{2-[((cis)-4-{[4-ethylthiobenzyl]amino}-3-piperidinyl)amino]-2-oxoethyl}-5-(trifluoromethyl)benzamide;
N-{2-[((cis)-4-{[4-methylthiobenzyl]amino}-1-methyl-3-piperidinyl)amino]-2-oxoethyl}-3-(trifluoromethyl)benzamide;
N-{2-[((cis)-4-{bis[4-methylthiobenzyl]amino}-1-methyl-3-piperidinyl)amino]-2-oxoethyl}-3-(trifluoromethyl)benzamide;
2-Amino-N-{2-[((cis)-4-{[4-methylthiobenzyl]amino}-1-methyl-3-piperidinyl)amino]-2-oxoethyl}-5-(trifluoromethyl)benzamide;
N-{2-[((cis)-4-{[4-methylthiobenzyl]amino}-1-acetyl-3-piperidinyl)amino]-2-oxoethyl}-3-(trifluoromethyl)benzamide;
2-Amino-N-{2-[((cis)-4-{[4-methylthiobenzyl]amino}-1-butyl-3-piperidinyl)amino]-2-oxoethyl}-5-(trifluoromethyl)benzamide;
2-Cyclohexylamino-N-{2-[((cis)-4-{[4-methylthiobenzyl]amino}-1-propyl-3 -piperidinyl)amino]-2-oxoethyl}-5-(trifluoromethyl)benzamide;
2-Iso-propylamino-N-{2-[((cis)-4-{[4-methylthiobenzyl]amino}-1-propyl-3-piperidinyl)amino]-2-oxoethyl}-5-(trifluoromethyl)benzamide;
2-(Pyrrolidinylcarbonyl)amino-N-{2-[((cis)-4-{[4-methylthiobenzyl]amino}-1-propyl-3-piperidinyl)amino]-2-oxoethyl}-5-(trifluoromethyl)benzamide;
2-(Methylaminocarbonyl)amino-N-{2[((cis)-4-{[4-methylthiobenzyl]amino}-1-propyl-3-piperidinyl)amino]-2-oxoethyl}-5-(trifluoromethyl)benzamide;
3-Amino-N-{2-[((cis)-4-{[4-methylthiobenzyl]amino}-1-propyl-3-piperidinyl)amino]-2-oxoethyl}-5-(trifluoromethyl)benzamide;
N-{2-[((cis)-4-{[4-aminosulfonylbenzoyl]amino}-3-piperidinyl)amino]-2-oxoethyl}-3-(trifluoromethyl)benzamide;
N-{2-[((cis)-4-{[4-methylsulfonylbenzoyl]amino}-3-piperidinyl)amino]-2-oxoethyl}-3-(trifluoromethyl)benzamide;
2-Amino-N-{2-[((cis)-4-{[4-(methylthio)benzoyl]amino}-3-piperidinyl)amino]-2-oxoethyl}-5-(trifluoromethyl)benzamide;
N-{2-[((cis)-4-{[4-methylthiobenzoyl]amino }-1-methyl-3-piperidinyl)amino]-2-oxoethyl}-3-(trifluoromethyl)benzamide;
N-{2-[((cis)-4-{[4-methylthiobenzoyl]amino}-1-acetyl-3-piperidinyl)amino]-2-oxoethy}-3-(trifluoromethyl)benzamide;
2-Amino-N-{2-[((cis)-4-{[4-methylthiobenzoyl]amino}-1-butyl-3-piperidinyl)amino]-2-oxoethyl}-3-(trifluoromethyl)benzamide;
2-Cyclohexylamino-N-{2-[((cis)-4-{[4-methylthiobenzoyl]amino}-1-propyl-3-piperidinyl)amino]-2-oxoethyl}-5-(trifluoromethyl)benzamide;
2-Iso-propylamino-N-{2-[((cis)-4-{[4-methylthiobenzoyl]amino}-1-propyl-3-piperidinyl)amino]-2-oxoethyl}-5-(trifluoromethyl)benzamide;
3-Amino-N-{2-[((cis)-4-{[4-methylthiobenzoyl]amino}-1-propyl-3 -piperidinyl)amino]-2-oxoethyl}-5-(trifluoromethyl)benzamide; and
N-{2-[((cis)-3-{[4-(aminosulfonyl)benzoyl]amino}-4-piperidinyl)amino]-2-oxoethyl}-3-(trifluoromethyl)benzamide.

10. A pharmaceutical composition, comprising a pharmaceutically acceptable carrier and a therapeutically effective amount of a compound of claim 1.

11. A method for treating disorders, comprising administering to a patient in need thereof a therapeutically effective amount of a compound of claim 1, said disorders being selected from multiple sclerosis, artherosclerosis, and rheumatoid arthritis.

12. A method for treating rheumatoid arthritis, comprising administering to a patient in need thereof a therapeutically effective amount of a compound of claim 1.

13. A method for treating multiple sclerosis, comprising administering to a patient in need thereof a therapeutically effective amount of a compound of claim 1.

14. A method for treating atherosclerosis, comprising administering to a patient in need thereof a therapeutically effective amount of a compound of claim 1.

* * * * *

UNITED STATES PATENT AND TRADEMARK OFFICE
CERTIFICATE OF CORRECTION

PATENT NO. : 7,572,813 B2
APPLICATION NO. : 11/315385
DATED : August 11, 2009
INVENTOR(S) : Robert Cherney It is certified that error appears in the above-identified patent and that said Letters Patent is hereby corrected as shown below:

Title Page, Column 2, (Foreign Patent Documents)
Line 17, "11/1999" should read -- 11/1997 --.

Title Page, Column 2, (Other Publications)
Line 2, "Hihgly" should read -- Highly --;
Line 3, "6598-5703" should read -- 5698-5703 --.

Title Page, Column 2, (Attorney, Agent or Firm)
Line 1, "Terrence" should read -- Terence --.

Column 124
Line 18, "$C_{-1-6}$" should read -- $C_{1-6}$ --;
Line 29, "0-2 $R^e$," should read -- 0-2 $R^{5e}$, --;
Line 32, "$C_{3-6}$ cycloalkcyl," should read -- $C_{3-6}$ cycloalkyl, --;
Line 38, "—C(O)NR$^{5f}$R$^{5f}$" should read -- —C(O)NR$^{5f}$R$^{5f}$, --.

Column 126
Line 12, "H," should read -- H; --;
Line 13, "H," should read -- H; --.

Column 127
Line 21, "0-2$R^6$," should read -- 0-2 $R^6$, --;
Line 28, after "isoquinolinyl" insert -- , --;
Lines 40-41, "isoquinolinyl" should read -- isoquinolinyl, --;
Line 67, "(CRR)$_r$C(O)O(CRR)$_r$R$^{6d}$," should read -- (CRR)$_r$C(O)O(CRR)$_r$R$^{6d}$, --.

Column 128
Line 19, "occurrence" should read -- occurrence, --;
Line 23, "s- butyl," should read -- s-butyl, --;
Line 35, "hexyl,," should read -- hexyl, --;
Line 37, "CH$_2$cyclopropyl," should read -- CH$_2$-cyclopropyl, --.

Signed and Sealed this

Sixteenth Day of November, 2010

David J. Kappos
*Director of the United States Patent and Trademark Office*

Column 129

Line 9, after "wherein" delete -- in text --;
Line 33, "I-butyl," should read -- i-butyl, --;
Line 37, "O (CH$_2$)$_r$R$^{6d}$," should read -- O(CH$_2$)$_r$R$^{6d}$, --;
Line 40, "H" should read -- H, --;
Line 47, "4R)-{[4-" should read -- 4R)-4-{[4- --;
Line 48, "aminol]" should read -- amino] --;
Line 58, "amino]-2-oxoethy}" should read -- amino]-2-oxoethyl} --;
Line 59, "(methythio)" should read -- (methylthio) --.

Column 130

Line 1, "{[4-ethylthiobenzyl]" should read -- {[4-methylthiobenzyl] --;
Line 20, "l-propyl-3 -piperidinyl)" should read -- l-propyl-3-piperidinyl) --;
Line 29, "{2[((cis)-4-" should read -- {2-[((cis)-4- --;
Line 44, "amino }-1" should read -- amino}-1 --;
Line 48, "2-oxoethy}" should read -- 2-oxoethyl} --;
Line 60, "1-propyl-3 -piperidinyl)" should read -- 1-propyl-3-piperidinyl) --.

Column 131

Line 4, "artherosclerosis," should read -- atherosclerosis, --.